(12) United States Patent
Velculescu et al.

(10) Patent No.: US 11,959,142 B2
(45) Date of Patent: Apr. 16, 2024

(54) DETECTION OF CANCER

(71) Applicant: The Johns Hopkins University, Baltimore, MD (US)

(72) Inventors: Victor Velculescu, Dayton, MD (US); Jillian A. Phallen, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 100 days.

(21) Appl. No.: 16/610,772

(22) PCT Filed: May 3, 2018

(86) PCT No.: PCT/US2018/030905
§ 371 (c)(1),
(2) Date: Nov. 4, 2019

(87) PCT Pub. No.: WO2018/204657
PCT Pub. Date: Nov. 8, 2018

(65) Prior Publication Data
US 2020/0157636 A1 May 21, 2020

Related U.S. Application Data

(60) Provisional application No. 62/516,009, filed on Jun. 6, 2017, provisional application No. 62/501,686, filed on May 4, 2017.

(51) Int. Cl.
| | | |
|---|---|---|
| *C12Q 1/6886* | (2018.01) | |
| *C12Q 1/6806* | (2018.01) | |
| *G16B 20/20* | (2019.01) | |
| *G16B 25/10* | (2019.01) | |
| *G16B 30/10* | (2019.01) | |

(52) U.S. Cl.
CPC ......... *C12Q 1/6886* (2013.01); *C12Q 1/6806* (2013.01); *G16B 20/20* (2019.02); *G16B 25/10* (2019.02); *G16B 30/10* (2019.02); *C12Q 2600/112* (2013.01); *C12Q 2600/156* (2013.01)

(58) Field of Classification Search
CPC ............ C12Q 1/6886; C12Q 1/6806; C12Q 2600/112; C12Q 2600/156; G16B 20/20; G16B 25/10; G16B 30/10
See application file for complete search history.

(56) References Cited

U.S. PATENT DOCUMENTS

| | | | |
|---|---|---|---|
| 2014/0227705 A1 | 8/2014 | Vogelstein et al. | |
| 2015/0252415 A1 | 9/2015 | Vogelstein et al. | |
| 2015/0361492 A1 | 12/2015 | Vogelstein et al. | |
| 2016/0215333 A1 | 7/2016 | Vogelstein et al. | |
| 2016/0251704 A1 | 9/2016 | Talasaz et al. | |
| 2018/0002747 A1* | 1/2018 | Druley | C12Q 1/6858 |

FOREIGN PATENT DOCUMENTS

| | | |
|---|---|---|
| WO | 2012/142213 A2 | 10/2012 |
| WO | 2016134136 A3 | 11/2016 |

OTHER PUBLICATIONS

Han et al., Genomic Proteomics Bioinformatics, 15, 59-72, Apr. 7, (Year: 2017).*
Bettegowda et. al., Sci Transl Med. 6(224): 224ra24, pp. 1-12, Feb. (Year: 2014).*
Fernandez-Cuesta et al (EBioMedicine 10, 117-123, June (Year: 2016).*
Newman et al (Nature Biotechnology, vol. 34 (5), 547-555, March (Year: 2016).*
Marengo et al. (World J. Gastroenterol, vol. 20, No. 37, pp. 13325-13342, Oct. 7, (Year: 2014).*
Ghosh et al. (Ind J. Clin Biochem, vol. 28, No. 1, pp. 24-29, (Year: 2013).*
Bettegowda et al. Detection of circulating tumor DNA in early- and late-stage human malignancies, Sci Trensl Med. Feb. 19, 2014 (Feb. 19, 2014), vol. 6. Iss. 224. pp. 1-25.
Haber et al "Blood-based analyses of cancer: circulating tumor cells and circulating tumor DNA," Cancer Discov, May 6, 2014 (May 6, 2014), vol. 4, pp. 650-661.
Leary et al. Detection of chromosomal alterations in the circulation of cancer patients with whole-genome sequencing, Sci Tranel Med, Nov. 28, 2012 (Nov. 28, 2012), vol. 4, Ms 162, pp. 1-21.
"Nextera XT DNA Sample Preparation Guide," Illumina, Oct. 1, 2012 (Oct. 1, 2012), Part # 15031942, Rev. C, pp. 1-46. Retrieved from the Internet. < http://cmore.soest.hawaii edu/summercourse/2015/documents/Metagenomics_06-22/nextre_xt_sample_preparation_guide_15031042_c.pdf> on Sep. 19, 2010 (Sep. 19, 2010).
International Search Report and Written Opinion of International Application No. PCT/US2018/030905, dated Oct. 2, 2018 (23 pages).
Kinde et al., "Detection and quantification of rare mutations with massively parallel sequencing," Proc. Natl. Acad. Sci. U.S.A., 108(23):pp. 9530-9535 (2011).

* cited by examiner

*Primary Examiner* — Cynthia B Wilder
(74) *Attorney, Agent, or Firm* — Fox Rothschild LLP

(57) ABSTRACT

Provided herein are methods of detecting circulating tumor DNA, cancer cell mutations, and/or cancer cells harboring one or more cancer cell mutations. In some embodiments, methods provided herein include detecting one or more genetic alterations in cell-free DNA. In some embodiments, methods provided herein for detecting one or more genetic alterations in cell-free DNA can be performed when the subject is not known to harbor a cancer cell and/or a cancer cell mutation (e.g., when the subject is not known to harbor a cancer cell having the cancer cell mutation).

8 Claims, 36 Drawing Sheets

Specification includes a Sequence Listing.

Table S1. Genes analyzed by TEC-Seq

| Gene | Region Analyzed | Gene Category* |
|---|---|---|
| ABL1 | Specific Exons | Cancer Driver Gene |
| AKT1 | Specific Exons | Cancer Driver Gene |
| ALK | Full Coding Region | Cancer Driver Gene |
| APC | Specific Exons | Cancer Driver Gene |
| AR | Full Coding Region | Cancer Driver Gene |
| ATM | Specific Exons | Cancer Driver and Clonal Hematopoiesis Gene |
| BRAF | Full Coding Region | Cancer Driver Gene |
| CDH1 | Specific Exons | Cancer Driver Gene |
| CDK4 | Full Coding Region | Cancer Driver Gene |
| CDK6 | Full Coding Region | Cancer Driver Gene |
| CDKN2A | Specific Exons | Cancer Driver Gene |
| CSF1R | Specific Exons | Cancer Driver Gene |
| CTNNB1 | Specific Exons | Cancer Driver Gene |
| DNMT3A | Specific Exons | Cancer Driver and Clonal Hematopoiesis Gene |
| EGFR | Full Coding Region | Cancer Driver Gene |
| ERBB2 | Specific Exons | Cancer Driver Gene |
| ERBB4 | Full Coding Region | Cancer Driver Gene |
| ESR1 | Full Coding Region | Cancer Driver Gene |
| EZH2 | Specific Exons | Cancer Driver Gene |
| FBXW7 | Specific Exons | Cancer Driver Gene |
| FGFR1 | Specific Exons | Cancer Driver Gene |
| FGFR2 | Specific Exons | Cancer Driver Gene |
| FGFR3 | Specific Exons | Cancer Driver Gene |
| FLT3 | Specific Exons | Cancer Driver Gene |
| GNA11 | Specific Exons | Cancer Driver Gene |
| GNAQ | Specific Exons | Cancer Driver Gene |
| GNAS | Specific Exons | Cancer Driver and Clonal Hematopoiesis Gene |
| HNF1A | Specific Exons | Cancer Driver Gene |
| HRAS | Full Coding Region | Cancer Driver Gene |
| IDH1 | Specific Exons | Cancer Driver and Clonal Hematopoiesis Gene |
| IDH2 | Specific Exons | Cancer Driver and Clonal Hematopoiesis Gene |
| JAK2 | Full Coding Region | Cancer Driver and Clonal Hematopoiesis Gene |
| JAK3 | Specific Exons | Cancer Driver Gene |
| KDR | Specific Exons | Cancer Driver Gene |
| KIT | Full Coding Region | Cancer Driver Gene |
| KRAS | Full Coding Region | Cancer Driver Gene |
| MAP2K1 | Specific Exons | Cancer Driver Gene |
| MET | Specific Exons | Cancer Driver Gene |
| MLH1 | Specific Exons | Cancer Driver Gene |
| MPL | Specific Exons | Cancer Driver Gene |
| MYC | Specific Exons | Cancer Driver Gene |
| NPM1 | Specific Exons | Cancer Driver Gene |
| NRAS | Full Coding Region | Cancer Driver Gene |
| PDGFRA | Full Coding Region | Cancer Driver Gene |
| PIK3CA | Full Coding Region | Cancer Driver Gene |
| PIK3R1 | Specific Exons | Cancer Driver Gene |
| PTEN | Full Coding Region | Cancer Driver Gene |
| PTPN11 | Specific Exons | Cancer Driver Gene |
| RB1 | Specific Exons | Cancer Driver Gene |
| RET | Specific Exons | Cancer Driver Gene |
| SMAD4 | Specific Exons | Cancer Driver Gene |
| SMARCB1 | Specific Exons | Cancer Driver Gene |
| SMO | Specific Exons | Cancer Driver Gene |
| SRC | Specific Exons | Cancer Driver Gene |
| STK11 | Full Coding Region | Cancer Driver Gene |
| TERT | Specific Exons | Cancer Driver Gene |
| TP53 | Full Coding Region | Cancer Driver Gene |
| VHL | Specific Exons | Cancer Driver Gene |

* Analyzed genes included those that have been commonly implicated in cancer(22). Specific genes (DNMT3A, IDH1, and IDH2) or certain alterations with genes (ATM amino acid residue 3008, GNAS amino acid residue 202 and JAK2 amino acid residue 617) were considered related to blood cell proliferation (24-26).

Table S4. Summary of genomic analyses

| Patient | Patient Type | Sample Type | Analysis Type | Read Length | Bases in Target Region | Bases Mapped to Genome | Bases Mapped to Target Regions | Percent Mapped to Target Regions | Total Coverage | Distinct Coverage | Tumor Normal Match (%) |
|---|---|---|---|---|---|---|---|---|---|---|---|
| CGPLBR100 | Breast Cancer | cfDNA | TEC-Seq | 100 | 80930 | 7299864400 | 3750272051 | 51% | 44784 | 3249 | NA |
| CGPLBR101 | Breast Cancer | cfDNA | TEC-Seq | 100 | 80930 | 7420822600 | 3810365416 | 51% | 45565 | 9784 | NA |
| CGPLBR102 | Breast Cancer | cfDNA | TEC-Seq | 100 | 80930 | 6679304900 | 3269688319 | 49% | 38679 | 7613 | NA |
| CGPLBR103 | Breast Cancer | cfDNA | TEC-Seq | 100 | 80930 | 7040304400 | 3495542488 | 50% | 41786 | 6748 | NA |
| CGPLBR104 | Breast Cancer | cfDNA | TEC-Seq | 100 | 80930 | 7188326200 | 3716096781 | 52% | 44316 | 9448 | NA |
| CGPLBR38 | Breast Cancer | cfDNA | TEC-Seq | 100 | 80930 | 7810253900 | 4057576306 | 52% | 48098 | 9868 | NA |
| CGPLBR39 | Breast Cancer | cfDNA | TEC-Seq | 100 | 80930 | 7745701500 | 3805623239 | 49% | 45084 | 11065 | NA |
| CGPLBR40 | Breast Cancer | cfDNA | TEC-Seq | 100 | 80930 | 7558990500 | 3852442341 | 48% | 43333 | 12948 | NA |
| CGPLBR41 | Breast Cancer | cfDNA | TEC-Seq | 100 | 80930 | 7900994600 | 3836600101 | 49% | 45535 | 10847 | NA |
| CGPLBR42 | Breast Cancer | cfDNA | TEC-Seq | 100 | 80930 | 7756986400 | 3456255655 | 45% | 40980 | 7211 | NA |
| CGPLBR43 | Breast Cancer | cfDNA | TEC-Seq | 100 | 80930 | 7561881700 | 3880346064 | 51% | 46098 | 8588 | NA |
| CGPLBR44 | Breast Cancer | cfDNA | TEC-Seq | 100 | 80930 | 7017744200 | 3269210569 | 47% | 38672 | 8344 | NA |
| CGPLBR48 | Breast Cancer | cfDNA | TEC-Seq | 100 | 80930 | 5629044200 | 2611554623 | 46% | 30860 | 8652 | NA |
| CGPLBR49 | Breast Cancer | cfDNA | TEC-Seq | 100 | 80930 | 5784711500 | 2673453893 | 46% | 31274 | 10429 | NA |
| CGPLBR53 | Breast Cancer | cfDNA | TEC-Seq | 100 | 80930 | 7223682000 | 3635203812 | 50% | 43212 | 4722 | NA |
| CGPLBR55 | Breast Cancer | cfDNA | TEC-Seq | 100 | 80930 | 8309154900 | 4306956281 | 52% | 51143 | 8328 | NA |
| CGPLBR57 | Breast Cancer | cfDNA | TEC-Seq | 100 | 80930 | 8636181000 | 4391501608 | 51% | 52108 | 5857 | NA |
| CGPLBR59 | Breast Cancer | cfDNA | TEC-Seq | 100 | 80930 | 8759457700 | 4152328555 | 47% | 49281 | 5855 | NA |
| CGPLBR61 | Breast Cancer | cfDNA | TEC-Seq | 100 | 80930 | 8163706700 | 3952810628 | 48% | 46755 | 3522 | NA |
| CGPLBR63 | Breast Cancer | cfDNA | TEC-Seq | 100 | 80930 | 7020533100 | 3542463704 | 50% | 41956 | 4773 | NA |
| CGPLBR64 | Breast Cancer | cfDNA | TEC-Seq | 100 | 80930 | 7300630900 | 3292529227 | 45% | 38909 | 5202 | NA |
| CGPLBR66 | Breast Cancer | cfDNA | TEC-Seq | 100 | 80930 | 6963339500 | 3554735108 | 51% | 42011 | 6399 | NA |
| CGPLBR67 | Breast Cancer | cfDNA | TEC-Seq | 100 | 80930 | 8264353900 | 3686093696 | 45% | 43516 | 7752 | NA |
| CGPLBR68 | Breast Cancer | cfDNA | TEC-Seq | 100 | 80930 | 7629312300 | 4078969547 | 53% | 48389 | 7402 | NA |
| CGPLBR69 | Breast Cancer | cfDNA | TEC-Seq | 100 | 80930 | 7571501500 | 3857354512 | 51% | 45322 | 7047 | NA |
| CGPLBR70 | Breast Cancer | cfDNA | TEC-Seq | 100 | 80930 | 7251760700 | 3641333708 | 50% | 43203 | 8864 | NA |
| CGPLBR71 | Breast Cancer | cfDNA | TEC-Seq | 100 | 80930 | 8515402600 | 4496696391 | 53% | 53340 | 6305 | NA |
| CGPLBR72 | Breast Cancer | cfDNA | TEC-Seq | 100 | 80930 | 8556946900 | 4389761697 | 51% | 52081 | 5632 | NA |
| CGPLBR73 | Breast Cancer | cfDNA | TEC-Seq | 100 | 80930 | 7958392300 | 4006933338 | 50% | 47555 | 8791 | NA |
| CGPLBR74 | Breast Cancer | cfDNA | TEC-Seq | 100 | 80930 | 8524536400 | 4063900599 | 48% | 48252 | 7013 | NA |
| CGPLBR75 | Breast Cancer | cfDNA | TEC-Seq | 100 | 80930 | 8260379100 | 3960599285 | 48% | 46955 | 6319 | NA |
| CGPLBR76 | Breast Cancer | cfDNA | TEC-Seq | 100 | 80930 | 7774235200 | 3893622420 | 50% | 46182 | 9628 | NA |
| CGPLBR77 | Breast Cancer | cfDNA | TEC-Seq | 100 | 80930 | 7572797600 | 3259863429 | 43% | 38568 | 8263 | NA |
| CGPLBR79 | Breast Cancer | cfDNA | TEC-Seq | 100 | 80930 | 7986015700 | 4100997532 | 51% | 48675 | 3254 | NA |
| CGPLBR80 | Breast Cancer | cfDNA | TEC-Seq | 100 | 80930 | 6845325800 | 3147476693 | 46% | 37709 | 5595 | NA |
| CGPLBR82 | Breast Cancer | cfDNA | TEC-Seq | 100 | 80930 | 8236705200 | 4170485005 | 51% | 49361 | 12319 | NA |
| CGPLBR83 | Breast Cancer | cfDNA | TEC-Seq | 100 | 80930 | 7434568100 | 3676285019 | 49% | 43628 | 5458 | NA |
| CGPLBR86 | Breast Cancer | cfDNA | TEC-Seq | 100 | 80930 | 7616282500 | 3644791327 | 48% | 43490 | 7048 | NA |
| CGPLBR87 | Breast Cancer | cfDNA | TEC-Seq | 100 | 80930 | 6194021300 | 3004882010 | 49% | 35765 | 5306 | NA |
| CGPLBR88 | Breast Cancer | cfDNA | TEC-Seq | 100 | 80930 | 6071567200 | 2847826237 | 47% | 33945 | 10319 | NA |
| CGPLBR91 | Breast Cancer | cfDNA | TEC-Seq | 100 | 80930 | 7192457700 | 3480203404 | 48% | 41570 | 9912 | NA |
| CGPLBR92 | Breast Cancer | cfDNA | TEC-Seq | 100 | 80930 | 7678981800 | 3600279233 | 47% | 42975 | 13580 | NA |
| CGPLBR93 | Breast Cancer | cfDNA | TEC-Seq | 100 | 80930 | 7605717800 | 3998713397 | 53% | 47866 | 10329 | NA |
| CGPLBR96 | Breast Cancer | cfDNA | TEC-Seq | 100 | 80930 | 6297446700 | 2463064737 | 39% | 29341 | 7937 | NA |
| CGPLBR97 | Breast Cancer | cfDNA | TEC-Seq | 100 | 80930 | 7114921600 | 3557069027 | 50% | 42488 | 10712 | NA |
| CGPLBR99 | Breast Cancer | cfDNA | TEC-Seq | 100 | 80930 | 6946513800 | 3223603304 | 46% | 38391 | 5412 | NA |
| CGCRC291 | Colorectal Cancer | cfDNA | TEC-Seq | 100 | 80930 | 7501485800 | 3771359756 | 50% | 44349 | 10359 | NA |
| CGCRC292 | Colorectal Cancer | cfDNA | TEC-Seq | 100 | 80930 | 6736035200 | 3098886973 | 46% | 36448 | 8603 | NA |
| CGCRC293 | Colorectal Cancer | cfDNA | TEC-Seq | 100 | 80930 | 6300244000 | 2818734206 | 45% | 33117 | 5953 | NA |
| CGCRC294 | Colorectal Cancer | cfDNA | TEC-Seq | 100 | 80930 | 7726872600 | 3911796709 | 50% | 46016 | 12071 | NA |
| CGCRC295 | Colorectal Cancer | cfDNA | TEC-Seq | 100 | 80930 | 8240860200 | 3478059753 | 42% | 40787 | 5826 | NA |
| CGCRC296 | Colorectal Cancer | cfDNA | TEC-Seq | 100 | 80930 | 5718556500 | 2898549356 | 51% | 33912 | 10180 | NA |
| CGCRC297 | Colorectal Cancer | cfDNA | TEC-Seq | 100 | 80930 | 7550826100 | 3717222432 | 49% | 43545 | 5870 | NA |
| CGCRC298 | Colorectal Cancer | cfDNA | TEC-Seq | 100 | 80930 | 12501036400 | 6096393754 | 49% | 71196 | 9617 | NA |
| CGCRC299 | Colorectal Cancer | cfDNA | TEC-Seq | 100 | 80930 | 7812602900 | 4121569690 | 53% | 48098 | 10338 | NA |
| CGCRC300 | Colorectal Cancer | cfDNA | TEC-Seq | 100 | 80930 | 8648090300 | 3962285136 | 46% | 46364 | 5756 | NA |
| CGCRC301 | Colorectal Cancer | cfDNA | TEC-Seq | 100 | 80930 | 7538758100 | 3695480348 | 49% | 43024 | 6618 | NA |
| CGCRC302 | Colorectal Cancer | cfDNA | TEC-Seq | 100 | 80930 | 8573658300 | 4349420574 | 51% | 51006 | 13799 | NA |
| CGCRC303 | Colorectal Cancer | cfDNA | TEC-Seq | 100 | 80930 | 5224046800 | 2505714343 | 48% | 29365 | 3372 | NA |
| CGCRC304 | Colorectal Cancer | cfDNA | TEC-Seq | 100 | 80930 | 5762112600 | 2942170530 | 51% | 34462 | 10208 | NA |
| CGCRC305 | Colorectal Cancer | cfDNA | TEC-Seq | 100 | 80930 | 7213384100 | 3726953480 | 52% | 43516 | 8589 | NA |
| CGCRC306 | Colorectal Cancer | cfDNA | TEC-Seq | 100 | 80930 | 7075579700 | 3552441899 | 50% | 41507 | 7372 | NA |
| CGCRC307 | Colorectal Cancer | cfDNA | TEC-Seq | 100 | 80930 | 7572627700 | 3492191519 | 46% | 40793 | 9680 | NA |
| CGCRC308 | Colorectal Cancer | cfDNA | TEC-Seq | 100 | 80930 | 7945738000 | 3895908986 | 49% | 45224 | 11809 | NA |
| CGCRC309 | Colorectal Cancer | cfDNA | TEC-Seq | 100 | 80930 | 8487455800 | 3921079811 | 46% | 45736 | 10739 | NA |
| CGCRC310 | Colorectal Cancer | cfDNA | TEC-Seq | 100 | 80930 | 9003580500 | 4678812441 | 52% | 54713 | 11139 | NA |
| CGCRC311 | Colorectal Cancer | cfDNA | TEC-Seq | 100 | 80930 | 6528162700 | 3276653864 | 50% | 38324 | 6044 | NA |
| CGCRC312 | Colorectal Cancer | cfDNA | TEC-Seq | 100 | 80930 | 7683294300 | 3316719187 | 43% | 38652 | 4622 | NA |
| CGCRC313 | Colorectal Cancer | cfDNA | TEC-Seq | 100 | 80930 | 5874099200 | 2896148722 | 49% | 33821 | 6506 | NA |
| CGCRC314 | Colorectal Cancer | cfDNA | TEC-Seq | 100 | 80930 | 6883148500 | 3382767492 | 49% | 39414 | 6664 | NA |
| CGCRC315 | Colorectal Cancer | cfDNA | TEC-Seq | 100 | 80930 | 7497252500 | 3775556051 | 50% | 44034 | 8686 | NA |
| CGCRC316 | Colorectal Cancer | cfDNA | TEC-Seq | 100 | 80930 | 10684720400 | 5553857153 | 52% | 64693 | 14289 | NA |
| CGCRC317 | Colorectal Cancer | cfDNA | TEC-Seq | 100 | 80930 | 7085877600 | 3669434216 | 52% | 43558 | 10944 | NA |
| CGCRC318 | Colorectal Cancer | cfDNA | TEC-Seq | 100 | 80930 | 6880041100 | 3326357413 | 48% | 39077 | 11571 | NA |
| CGCRC319 | Colorectal Cancer | cfDNA | TEC-Seq | 100 | 80930 | 7485342900 | 3982877483 | 53% | 47327 | 10502 | NA |
| CGCRC320 | Colorectal Cancer | cfDNA | TEC-Seq | 100 | 80930 | 7058703200 | 3450648135 | 49% | 40888 | 10198 | NA |
| CGCRC321 | Colorectal Cancer | cfDNA | TEC-Seq | 100 | 80930 | 7203625900 | 3633396892 | 50% | 43065 | 6499 | NA |
| CGCRC332 | Colorectal Cancer | cfDNA | TEC-Seq | 100 | 80930 | 7202969100 | 3758323705 | 52% | 44580 | 3243 | NA |
| CGCRC333 | Colorectal Cancer | cfDNA | TEC-Seq | 100 | 80930 | 8767144700 | 4199126827 | 48% | 49721 | 8336 | NA |
| CGCRC334 | Colorectal Cancer | cfDNA | TEC-Seq | 100 | 80930 | 7771869100 | 3944558280 | 51% | 46518 | 5014 | NA |
| CGCRC335 | Colorectal Cancer | cfDNA | TEC-Seq | 100 | 80930 | 7972524600 | 4064901201 | 51% | 48308 | 6151 | NA |
| CGCRC336 | Colorectal Cancer | cfDNA | TEC-Seq | 100 | 80930 | 8597346400 | 4333410573 | 50% | 51390 | 7551 | NA |
| CGCRC337 | Colorectal Cancer | cfDNA | TEC-Seq | 100 | 80930 | 7389611700 | 3800666199 | 51% | 45083 | 8092 | NA |

Figure 18A

| | | | | | | | | | | |
|---|---|---|---|---|---|---|---|---|---|---|
| CGCRC338 | Colorectal Cancer | cfDNA | TEC-Seq | 100 | 80930 | 8029493700 | 4179383804 | 52% | 49380 | 5831 | NA |
| CGCRC339 | Colorectal Cancer | cfDNA | TEC-Seq | 100 | 80930 | 7938963600 | 4095555110 | 52% | 48397 | 3808 | NA |
| CGCRC340 | Colorectal Cancer | cfDNA | TEC-Seq | 100 | 80930 | 7214829500 | 3706643088 | 51% | 43805 | 3014 | NA |
| CGCRC341 | Colorectal Cancer | cfDNA | TEC-Seq | 100 | 80930 | 6803159200 | 3668208527 | 42% | 43106 | 11957 | NA |
| CGCRC342 | Colorectal Cancer | cfDNA | TEC-Seq | 100 | 80930 | 8478311500 | 3425540889 | 40% | 40328 | 9592 | NA |
| CGPLH35 | Healthy | cfDNA | TEC-Seq | 100 | 80930 | 6919126300 | 2312758764 | 33% | 25570 | 1989 | NA |
| CGPLH36 | Healthy | cfDNA | TEC-Seq | 100 | 80930 | 6089923400 | 2038548115 | 33% | 22719 | 1478 | NA |
| CGPLH37 | Healthy | cfDNA | TEC-Seq | 100 | 80930 | 5557270200 | 1935301929 | 35% | 21673 | 2312 | NA |
| CGPLH38 | Healthy | cfDNA | TEC-Seq | 100 | 80930 | 5771193800 | 1963294894 | 34% | 21816 | 784 | NA |
| CGPLH39 | Healthy | cfDNA | TEC-Seq | 100 | 80930 | 6002281900 | 2209984880 | 37% | 24788 | 563 | NA |
| CGPLH40 | Healthy | cfDNA | TEC-Seq | 100 | 80930 | 6773660700 | 2713539772 | 40% | 30611 | 409 | NA |
| CGPLH41 | Healthy | cfDNA | TEC-Seq | 100 | 80930 | 5660677000 | 1997748737 | 35% | 23006 | 583 | NA |
| CGPLH42 | Healthy | cfDNA | TEC-Seq | 100 | 80930 | 5792045400 | 2388036949 | 41% | 27197 | 2523 | NA |
| CGPLH43 | Healthy | cfDNA | TEC-Seq | 100 | 80930 | 5568321700 | 2017813329 | 36% | 23228 | 1650 | NA |
| CGPLH44 | Healthy | cfDNA | TEC-Seq | 100 | 80930 | 6636969300 | 2424276812 | 37% | 27040 | 1023 | NA |
| CGPLH45 | Healthy | cfDNA | TEC-Seq | 100 | 80930 | 8485593200 | 2770176078 | 33% | 32829 | 3114 | NA |
| CGPLH46 | Healthy | cfDNA | TEC-Seq | 100 | 80930 | 5083171100 | 1899395790 | 37% | 21821 | 1678 | NA |
| CGPLH47 | Healthy | cfDNA | TEC-Seq | 100 | 80930 | 6016382500 | 2062392156 | 34% | 23459 | 1431 | NA |
| CGPLH48 | Healthy | cfDNA | TEC-Seq | 100 | 80930 | 4958945900 | 1809825992 | 36% | 20702 | 1898 | NA |
| CGPLH49 | Healthy | cfDNA | TEC-Seq | 100 | 80930 | 7953812200 | 2511365904 | 32% | 27006 | 1440 | NA |
| CGPLH50 | Healthy | cfDNA | TEC-Seq | 100 | 80930 | 6989407600 | 2561288100 | 37% | 29177 | 2591 | NA |
| CGPLH51 | Healthy | cfDNA | TEC-Seq | 100 | 80930 | 7862073200 | 2525091396 | 32% | 29999 | 1293 | NA |
| CGPLH52 | Healthy | cfDNA | TEC-Seq | 100 | 80930 | 6939636800 | 2397922699 | 35% | 27029 | 2501 | NA |
| CGPLH53 | Healthy | cfDNA | TEC-Seq | 100 | 80930 | 7563547300 | 2316943911 | 31% | 24210 | 1109 | NA |
| CGPLH54 | Healthy | cfDNA | TEC-Seq | 100 | 80930 | 10611934700 | 2280823134 | 22% | 27175 | 3306 | NA |
| CGPLH55 | Healthy | cfDNA | TEC-Seq | 100 | 80930 | 9912659200 | 2521962244 | 25% | 27082 | 3191 | NA |
| CGPLH56 | Healthy | cfDNA | TEC-Seq | 100 | 80930 | 5777591900 | 2023874863 | 35% | 22916 | 1391 | NA |
| CGPLH57 | Healthy | cfDNA | TEC-Seq | 100 | 80930 | 9234904800 | 1493926244 | 16% | 15843 | 1655 | NA |
| CGPLH58 | Healthy | cfDNA | TEC-Seq | 100 | 80930 | 7571923100 | 2169535037 | 29% | 22576 | 1174 | NA |
| CGPLH59 | Healthy | cfDNA | TEC-Seq | 100 | 80930 | 9726052100 | 2987875484 | 31% | 35427 | 2143 | NA |
| CGPLH60 | Healthy | cfDNA | TEC-Seq | 100 | 80930 | 6812180400 | 2141533749 | 31% | 23217 | 493 | NA |
| CGPLH61 | Healthy | cfDNA | TEC-Seq | 100 | 80930 | 7703716900 | 2225623104 | 29% | 23858 | 724 | NA |
| CGPLH62 | Healthy | cfDNA | TEC-Seq | 100 | 80930 | 7565636200 | 2042450491 | 27% | 22021 | 453 | NA |
| CGPLH63 | Healthy | cfDNA | TEC-Seq | 100 | 80930 | 8696405000 | 2521574759 | 29% | 26689 | 1851 | NA |
| CGPLH64 | Healthy | cfDNA | TEC-Seq | 100 | 80930 | 5438852600 | 996198502 | 18% | 11477 | 1443 | NA |
| CGPLH75 | Healthy | cfDNA | TEC-Seq | 100 | 80930 | 3446444000 | 1505718480 | 44% | 17808 | 3016 | NA |
| CGPLH76 | Healthy | cfDNA | TEC-Seq | 100 | 80930 | 7499116400 | 3685762725 | 49% | 43682 | 4643 | NA |
| CGPLH77 | Healthy | cfDNA | TEC-Seq | 100 | 80930 | 6512408400 | 2537359345 | 39% | 30280 | 3131 | NA |
| CGPLH78 | Healthy | cfDNA | TEC-Seq | 100 | 80930 | 7642949300 | 3946069680 | 52% | 46316 | 5358 | NA |
| CGPLH79 | Healthy | cfDNA | TEC-Seq | 100 | 80930 | 7785475700 | 3910639227 | 50% | 45280 | 6714 | NA |
| CGPLH80 | Healthy | cfDNA | TEC-Seq | 100 | 80930 | 7918361500 | 3558236955 | 45% | 42171 | 5062 | NA |
| CGPLH81 | Healthy | cfDNA | TEC-Seq | 100 | 80930 | 6646268900 | 3112369850 | 47% | 37119 | 3678 | NA |
| CGPLH82 | Healthy | cfDNA | TEC-Seq | 100 | 80930 | 7744065000 | 3941700596 | 51% | 46820 | 5723 | NA |
| CGPLH83 | Healthy | cfDNA | TEC-Seq | 100 | 80930 | 6957686000 | 1447603106 | 21% | 17289 | 2875 | NA |
| CGPLH84 | Healthy | cfDNA | TEC-Seq | 100 | 80930 | 8326493200 | 3989908122 | 48% | 47464 | 3647 | NA |
| CGPLH85 | Healthy | cfDNA | TEC-Seq | 100 | 80930 | 8713042600 | 4461252636 | 51% | 53246 | 3721 | NA |
| CGPLH86 | Healthy | cfDNA | TEC-Seq | 100 | 80930 | 8664194700 | 4470145091 | 52% | 53398 | 5094 | NA |
| CGPLH90 | Healthy | cfDNA | TEC-Seq | 100 | 80930 | 7516078800 | 3841504088 | 51% | 45907 | 4414 | NA |
| CGPLH91 | Healthy | cfDNA | TEC-Seq | 100 | 80930 | 7356314100 | 3796192344 | 52% | 45369 | 3333 | NA |
| CGPLLU1 | Lung Cancer | cfDNA | TEC-Seq | 100 | 80930 | 6239458800 | 2329606202 | 37% | 26443 | 5581 | NA |
| CGPLLU115 | Lung Cancer | cfDNA | TEC-Seq | 100 | 80930 | 10979564000 | 3536107395 | 32% | 38888 | 5994 | NA |
| CGPLLU116 | Lung Cancer | cfDNA | TEC-Seq | 100 | 80930 | 8427732900 | 2666386431 | 32% | 31382 | 7168 | NA |
| CGPLLU117 | Lung Cancer | cfDNA | TEC-Seq | 100 | 80930 | 7722272300 | 2377605802 | 31% | 27869 | 2500 | NA |
| CGPLLU118 | Lung Cancer | cfDNA | TEC-Seq | 100 | 80930 | 8821329900 | 3017869157 | 34% | 35234 | 2876 | NA |
| CGPLLU119 | Lung Cancer | cfDNA | TEC-Seq | 100 | 80930 | 8224786400 | 2826168731 | 34% | 32615 | 6973 | NA |
| CGPLLU135 | Lung Cancer | cfDNA | TEC-Seq | 100 | 80930 | 7479506200 | 2465400664 | 33% | 29106 | 4986 | NA |
| CGPLLU136 | Lung Cancer | cfDNA | TEC-Seq | 100 | 80930 | 9255976600 | 3044006428 | 33% | 35637 | 5742 | NA |
| CGPLLU137 | Lung Cancer | cfDNA | TEC-Seq | 100 | 80930 | 9182200700 | 2707533740 | 29% | 32066 | 5436 | NA |
| CGPLLU138 | Lung Cancer | cfDNA | TEC-Seq | 100 | 80930 | 8659694500 | 2845274314 | 33% | 33349 | 1669 | NA |
| CGPLLU139 | Lung Cancer | cfDNA | TEC-Seq | 100 | 80930 | 8269594200 | 2779580391 | 34% | 32503 | 5050 | NA |
| CGPLLU14 | Lung Cancer | cfDNA, serial blood draw 1 | TEC-Seq | 100 | 80930 | 7398028800 | 1699011387 | 23% | 20075 | 778 | NA |
| CGPLLU14 | Lung Cancer | cfDNA, serial blood draw 2 | TEC-Seq | 100 | 80930 | 5656145300 | 2098827088 | 37% | 23699 | 985 | NA |
| CGPLLU144 | Lung Cancer | cfDNA | TEC-Seq | 100 | 80930 | 8716827400 | 4218676624 | 48% | 49370 | 10771 | NA |
| CGPLLU145 | Lung Cancer | cfDNA | TEC-Seq | 100 | 80930 | 8925580700 | 4416873069 | 49% | 51680 | 6262 | NA |
| CGPLLU146 | Lung Cancer | cfDNA | TEC-Seq | 100 | 80930 | 8506844200 | 4195033049 | 49% | 49084 | 6968 | NA |
| CGPLLU147 | Lung Cancer | cfDNA | TEC-Seq | 100 | 80930 | 7416300600 | 3530746046 | 48% | 41302 | 4691 | NA |
| CGPLLU161 | Lung Cancer | cfDNA | TEC-Seq | 100 | 80930 | 7789148700 | 3280139772 | 42% | 38568 | 12229 | NA |
| CGPLLU162 | Lung Cancer | cfDNA | TEC-Seq | 100 | 80930 | 7625462000 | 3470147667 | 46% | 40918 | 10099 | NA |
| CGPLLU163 | Lung Cancer | cfDNA | TEC-Seq | 100 | 80930 | 8019293200 | 3946533993 | 49% | 46473 | 12108 | NA |
| CGPLLU164 | Lung Cancer | cfDNA | TEC-Seq | 100 | 80930 | 8110030900 | 3592748235 | 44% | 42161 | 6947 | NA |
| CGPLLU165 | Lung Cancer | cfDNA | TEC-Seq | 100 | 80930 | 8389514600 | 4147501817 | 49% | 48779 | 8996 | NA |
| CGPLLU166 | Lung Cancer | cfDNA | TEC-Seq | 100 | 80930 | 8040278000 | 3908624400 | 49% | 45999 | 11030 | NA |
| CGPLLU168 | Lung Cancer | cfDNA | TEC-Seq | 100 | 80930 | 7690630000 | 3868237773 | 50% | 45625 | 9711 | NA |
| CGPLLU169 | Lung Cancer | cfDNA | TEC-Seq | 100 | 80930 | 9378353000 | 4800407624 | 51% | 56547 | 10261 | NA |
| CGPLLU170 | Lung Cancer | cfDNA | TEC-Seq | 100 | 80930 | 7276494400 | 3543816325 | 49% | 41280 | 8803 | NA |
| CGPLLU173 | Lung Cancer | cfDNA | TEC-Seq | 100 | 80930 | 7592835800 | 2879843635 | 38% | 34033 | 6924 | NA |
| CGPLLU174 | Lung Cancer | cfDNA | TEC-Seq | 100 | 80930 | 7481844600 | 3067532518 | 41% | 36321 | 6137 | NA |
| CGPLLU175 | Lung Cancer | cfDNA | TEC-Seq | 100 | 80930 | 8533324200 | 4002541569 | 47% | 47084 | 7862 | NA |
| CGPLLU176 | Lung Cancer | cfDNA | TEC-Seq | 100 | 80930 | 8143905900 | 4054098929 | 50% | 47708 | 5588 | NA |
| CGPLLU177 | Lung Cancer | cfDNA | TEC-Seq | 100 | 80930 | 8421611300 | 4197108809 | 50% | 49476 | 8780 | NA |
| CGPLLU178 | Lung Cancer | cfDNA | TEC-Seq | 100 | 80930 | 8483124700 | 4169577489 | 49% | 48580 | 6445 | NA |
| CGPLLU179 | Lung Cancer | cfDNA | TEC-Seq | 100 | 80930 | 7774358700 | 3304915738 | 43% | 38768 | 6862 | NA |
| CGPLLU180 | Lung Cancer | cfDNA | TEC-Seq | 100 | 80930 | 8192813800 | 3937552475 | 48% | 46498 | 6568 | NA |
| CGPLLU19 | Lung Cancer | cfDNA | TEC-Seq | 100 | 80930 | 7263539200 | 2547333392 | 35% | 28493 | 3441 | NA |
| CGPLLU197 | Lung Cancer | cfDNA | TEC-Seq | 100 | 80930 | 7996779200 | 3082397881 | 39% | 36381 | 5388 | NA |
| CGPLLU198 | Lung Cancer | cfDNA | TEC-Seq | 100 | 80930 | 7175247200 | 3545719100 | 49% | 42008 | 6817 | NA |
| CGPLLU2 | Lung Cancer | cfDNA | TEC-Seq | 100 | 80930 | 9495304600 | 3389293546 | 36% | 40802 | 4853 | NA |

Figure 18B

| | | | | | | | | | | |
|---|---|---|---|---|---|---|---|---|---|---|
| CGPLLU20 | Lung Cancer | cfDNA | TEC-Seq | 100 | 80930 | 12481073200 | 994477545 | 8% | 10329 | 4129 | NA |
| CGPLLU202 | Lung Cancer | cfDNA | TEC-Seq | 100 | 80930 | 6840112800 | 3427820669 | 50% | 40670 | 7951 | NA |
| CGPLLU203 | Lung Cancer | cfDNA | TEC-Seq | 100 | 80930 | 7468749900 | 3762226574 | 50% | 44500 | 9917 | NA |
| CGPLLU204 | Lung Cancer | cfDNA | TEC-Seq | 100 | 80930 | 7445626400 | 3703545153 | 50% | 44317 | 6856 | NA |
| CGPLLU205 | Lung Cancer | cfDNA | TEC-Seq | 100 | 80930 | 9205429100 | 4350573991 | 47% | 51627 | 9810 | NA |
| CGPLLU206 | Lung Cancer | cfDNA | TEC-Seq | 100 | 80930 | 7397914600 | 3635210205 | 49% | 43016 | 7124 | NA |
| CGPLLU207 | Lung Cancer | cfDNA | TEC-Seq | 100 | 80930 | 7133043900 | 3736258011 | 52% | 44291 | 8499 | NA |
| CGPLLU208 | Lung Cancer | cfDNA | TEC-Seq | 100 | 80930 | 7346974800 | 3855814032 | 52% | 45782 | 8940 | NA |
| CGPLLU209 | Lung Cancer | cfDNA | TEC-Seq | 100 | 80930 | 6723337800 | 3362944595 | 50% | 39531 | 11946 | NA |
| CGPLLU21 | Lung Cancer | cfDNA | TEC-Seq | 100 | 80930 | 7869941100 | 1317965426 | 17% | 14215 | 3501 | NA |
| CGPLLU22 | Lung Cancer | cfDNA | TEC-Seq | 100 | 80930 | 7574547100 | 2108841152 | 28% | 21572 | 6544 | NA |
| CGPLLU23 | Lung Cancer | cfDNA | TEC-Seq | 100 | 80930 | 7019961300 | 2276529333 | 32% | 24728 | 3670 | NA |
| CGPLLU26 | Lung Cancer | cfDNA | TEC-Seq | 100 | 80930 | 8423085100 | 2399668113 | 28% | 25687 | 861 | NA |
| CGPLLU28 | Lung Cancer | cfDNA | TEC-Seq | 100 | 80930 | 8381515900 | 2342788295 | 28% | 24633 | 7424 | NA |
| CGPLLU29 | Lung Cancer | cfDNA | TEC-Seq | 100 | 80930 | 7475284900 | 2387903088 | 32% | 25788 | 3573 | NA |
| CGPLLU3 | Lung Cancer | cfDNA | TEC-Seq | 100 | 80930 | 5628696000 | 2034607883 | 36% | 22350 | 5122 | NA |
| CGPLLU30 | Lung Cancer | cfDNA | TEC-Seq | 100 | 80930 | 8699392200 | 2448312466 | 28% | 28625 | 7523 | NA |
| CGPLLU31 | Lung Cancer | cfDNA | TEC-Seq | 100 | 80930 | 4407055300 | 1196657814 | 27% | 13701 | 1573 | NA |
| CGPLLU4 | Lung Cancer | cfDNA | TEC-Seq | 100 | 80930 | 8456184600 | 3386153208 | 40% | 39896 | 3346 | NA |
| CGPLLU44 | Lung Cancer | cfDNA, serial blood draw 1 | TEC-Seq | 100 | 80930 | 9744751800 | 2002428243 | 21% | 21635 | 6924 | NA |
| CGPLLU44 | Lung Cancer | cfDNA, serial blood draw 2 | TEC-Seq | 100 | 80930 | 9622990500 | 3284300067 | 34% | 39152 | 7788 | NA |
| CGPLLU47 | Lung Cancer | cfDNA, serial blood draw 1 | TEC-Seq | 100 | 80930 | 8463284700 | 2682429672 | 32% | 28887 | 6048 | NA |
| CGPLLU47 | Lung Cancer | cfDNA, serial blood draw 2 | TEC-Seq | 100 | 80930 | 7710341500 | 3072111376 | 40% | 36516 | 6875 | NA |
| CGPLLU5 | Lung Cancer | cfDNA | TEC-Seq | 100 | 80930 | 6598676600 | 2581497896 | 39% | 29200 | 4018 | NA |
| CGPLLU54 | Lung Cancer | cfDNA | TEC-Seq | 100 | 80930 | 8486375600 | 2682295256 | 32% | 31317 | 3453 | NA |
| CGPLLU57 | Lung Cancer | cfDNA, serial blood draw 1 | TEC-Seq | 100 | 80930 | 9291392600 | 3154714157 | 34% | 37406 | 1902 | NA |
| CGPLLU57 | Lung Cancer | cfDNA, serial blood draw 2 | TEC-Seq | 100 | 80930 | 8244793600 | 2507050777 | 30% | 29132 | 2655 | NA |
| CGPLLU59 | Lung Cancer | cfDNA, serial blood draw 1 | TEC-Seq | 100 | 80930 | 10938574300 | 692400779 | 6% | 8033 | 1026 | NA |
| CGPLLU59 | Lung Cancer | cfDNA, serial blood draw 2 | TEC-Seq | 100 | 80930 | 5079072900 | 2009883319 | 40% | 23141 | 2173 | NA |
| CGPLLU6 | Lung Cancer | cfDNA | TEC-Seq | 100 | 80930 | 7056975000 | 2654750988 | 38% | 30203 | 5250 | NA |
| CGPLLU63 | Lung Cancer | cfDNA | TEC-Seq | 100 | 80930 | 7669552500 | 1044408279 | 14% | 12325 | 5802 | NA |
| CGPLLU64 | Lung Cancer | cfDNA | TEC-Seq | 100 | 80930 | 8088897900 | 3083234873 | 38% | 36108 | 5320 | NA |
| CGPLLU65 | Lung Cancer | cfDNA | TEC-Seq | 100 | 80930 | 8699641600 | 2679059287 | 31% | 30935 | 4831 | NA |
| CGPLLU66 | Lung Cancer | cfDNA | TEC-Seq | 100 | 80930 | 10396598700 | 3774873437 | 36% | 43806 | 1603 | NA |
| CGPLLU67 | Lung Cancer | cfDNA | TEC-Seq | 100 | 80930 | 7967355500 | 2652881488 | 33% | 30996 | 9590 | NA |
| CGPLLU68 | Lung Cancer | cfDNA | TEC-Seq | 100 | 80930 | 7414515500 | 2339316921 | 32% | 27348 | 7876 | NA |
| CGPLLU9 | Lung Cancer | cfDNA, serial blood draw 1 | TEC-Seq | 100 | 80930 | 7865706600 | 2818183586 | 36% | 32789 | 7118 | NA |
| CGPLLU9 | Lung Cancer | cfDNA, serial blood draw 2 | TEC-Seq | 100 | 80930 | 7632488500 | 2833849772 | 37% | 33369 | 3718 | NA |
| CGPLOV1 | Ovarian Cancer | cfDNA | TEC-Seq | 100 | 80930 | 6674383100 | 2571045006 | 39% | 30944 | 4752 | NA |
| CGPLOV10 | Ovarian Cancer | cfDNA | TEC-Seq | 100 | 80930 | 7073534200 | 3402308123 | 48% | 39820 | 4059 | NA |
| CGPLOV11 | Ovarian Cancer | cfDNA | TEC-Seq | 100 | 80930 | 6924062200 | 3324593050 | 48% | 38796 | 7185 | NA |
| CGPLOV12 | Ovarian Cancer | cfDNA | TEC-Seq | 100 | 80930 | 6552080100 | 3181854993 | 49% | 37340 | 6114 | NA |
| CGPLOV13 | Ovarian Cancer | cfDNA | TEC-Seq | 100 | 80930 | 6796755500 | 3264897084 | 48% | 38348 | 7931 | NA |
| CGPLOV14 | Ovarian Cancer | cfDNA | TEC-Seq | 100 | 80930 | 7856573900 | 3408425065 | 43% | 39997 | 7712 | NA |
| CGPLOV15 | Ovarian Cancer | cfDNA | TEC-Seq | 100 | 80930 | 7239201500 | 3322285607 | 46% | 38953 | 6644 | NA |
| CGPLOV16 | Ovarian Cancer | cfDNA | TEC-Seq | 100 | 80930 | 8570759900 | 4344288233 | 51% | 51009 | 11947 | NA |
| CGPLOV17 | Ovarian Cancer | cfDNA | TEC-Seq | 100 | 80930 | 6910310400 | 2805243492 | 41% | 32228 | 4307 | NA |
| CGPLOV18 | Ovarian Cancer | cfDNA | TEC-Seq | 100 | 80930 | 8173037600 | 4064432407 | 50% | 47714 | 5162 | NA |
| CGPLOV19 | Ovarian Cancer | cfDNA | TEC-Seq | 100 | 80930 | 7732198900 | 3672564399 | 47% | 43020 | 11127 | NA |
| CGPLOV2 | Ovarian Cancer | cfDNA | TEC-Seq | 100 | 80930 | 9365390900 | 3706407220 | 40% | 43375 | 5495 | NA |
| CGPLOV20 | Ovarian Cancer | cfDNA | TEC-Seq | 100 | 80930 | 7559602000 | 3678700179 | 49% | 43230 | 4872 | NA |
| CGPLOV21 | Ovarian Cancer | cfDNA | TEC-Seq | 100 | 80930 | 8948032900 | 4616255499 | 52% | 54012 | 12777 | NA |
| CGPLOV22 | Ovarian Cancer | cfDNA | TEC-Seq | 100 | 80930 | 8680136500 | 4049934586 | 47% | 46912 | 9715 | NA |
| CGPLOV23 | Ovarian Cancer | cfDNA | TEC-Seq | 100 | 80930 | 6660696600 | 3422631774 | 51% | 40810 | 9460 | NA |
| CGPLOV24 | Ovarian Cancer | cfDNA | TEC-Seq | 100 | 80930 | 8634287200 | 4272258165 | 49% | 50736 | 8689 | NA |
| CGPLOV25 | Ovarian Cancer | cfDNA | TEC-Seq | 100 | 80930 | 6979295000 | 3390206388 | 49% | 40188 | 5856 | NA |
| CGPLOV26 | Ovarian Cancer | cfDNA | TEC-Seq | 100 | 80930 | 7041093800 | 3728879661 | 53% | 44341 | 8950 | NA |
| CGPLOV27 | Ovarian Cancer | cfDNA | TEC-Seq | 100 | 80930 | 7036348000 | 3126621860 | 44% | 36944 | 8226 | NA |
| CGPLOV3 | Ovarian Cancer | cfDNA | TEC-Seq | 100 | 80930 | 5666658900 | 1644257965 | 29% | 18549 | 2703 | NA |
| CGPLOV4 | Ovarian Cancer | cfDNA | TEC-Seq | 100 | 80930 | 7652138800 | 2958089057 | 39% | 34791 | 3453 | NA |
| CGPLOV5 | Ovarian Cancer | cfDNA | TEC-Seq | 100 | 80930 | 6846268800 | 2569276432 | 38% | 30795 | 5514 | NA |
| CGPLOV6 | Ovarian Cancer | cfDNA | TEC-Seq | 100 | 80930 | 5802806700 | 2285641930 | 39% | 25954 | 4766 | NA |
| CGPLOV7 | Ovarian Cancer | cfDNA | TEC-Seq | 100 | 80930 | 5104003900 | 1911759262 | 37% | 22053 | 2832 | NA |
| CGPLOV8 | Ovarian Cancer | cfDNA | TEC-Seq | 100 | 80930 | 6247060500 | 2119191732 | 34% | 23377 | 3541 | NA |
| CGPLOV9 | Ovarian Cancer | cfDNA | TEC-Seq | 100 | 80930 | 4440232900 | 1135063183 | 26% | 12542 | 1159 | NA |
| CGPLOV28 | Ovarian Cancer | cfDNA | TEC-Seq | 100 | 80930 | 7429230900 | 3753051715 | 51% | 45430 | 4155 | NA |
| CGPLOV31 | Ovarian Cancer | cfDNA | TEC-Seq | 100 | 80930 | 8981384000 | 4621838729 | 51% | 55429 | 5458 | NA |
| CGPLOV32 | Ovarian Cancer | cfDNA | TEC-Seq | 100 | 80930 | 9344536800 | 4737698323 | 51% | 57234 | 6165 | NA |
| CGPLOV37 | Ovarian Cancer | cfDNA | TEC-Seq | 100 | 80930 | 8158083200 | 4184432898 | 51% | 50648 | 6934 | NA |
| CGPLOV38 | Ovarian Cancer | cfDNA | TEC-Seq | 100 | 80930 | 8654435400 | 4492987085 | 52% | 53789 | 6124 | NA |
| CGPLOV40 | Ovarian Cancer | cfDNA | TEC-Seq | 100 | 80930 | 9868640700 | 4934400809 | 50% | 59049 | 7721 | NA |
| CGPLOV41 | Ovarian Cancer | cfDNA | TEC-Seq | 100 | 80930 | 7689013600 | 3861448829 | 50% | 46292 | 4469 | NA |
| CGPLOV42 | Ovarian Cancer | cfDNA | TEC-Seq | 100 | 80930 | 9836516900 | 4264154366 | 49% | 58302 | 7632 | NA |
| CGPLOV43 | Ovarian Cancer | cfDNA | TEC-Seq | 100 | 80930 | 8756507100 | 4515479918 | 52% | 54661 | 4310 | NA |
| CGPLOV44 | Ovarian Cancer | cfDNA | TEC-Seq | 100 | 80930 | 7576310800 | 4120933922 | 54% | 49903 | 4969 | NA |
| CGPLOV46 | Ovarian Cancer | cfDNA | TEC-Seq | 100 | 80930 | 9346036300 | 5037820346 | 54% | 61204 | 3927 | NA |
| CGPLOV47 | Ovarian Cancer | cfDNA | TEC-Seq | 100 | 80930 | 10880620200 | 5491357828 | 50% | 66363 | 6895 | NA |
| CGPLOV48 | Ovarian Cancer | cfDNA | TEC-Seq | 100 | 80930 | 7658707800 | 3335991337 | 44% | 40332 | 4066 | NA |
| CGPLOV49 | Ovarian Cancer | cfDNA | TEC-Seq | 100 | 80930 | 10076208000 | 5519656698 | 55% | 67117 | 5097 | NA |
| CGPLOV50 | Ovarian Cancer | cfDNA | TEC-Seq | 100 | 80930 | 8239290400 | 4472380278 | 54% | 54150 | 3836 | NA |
| CGPLBR100 | Breast Cancer | Tumor DNA | Targeted NGS | 150 | 639291 | 989328900 | 456255327 | 46% | 702 | 259 | 100% |
| CGPLBR38 | Breast Cancer | Tumor DNA | Targeted NGS | 150 | 639291 | 1300314150 | 653992005 | 50% | 998 | 529 | 100% |
| CGPLBR39 | Breast Cancer | Tumor DNA | Targeted NGS | 150 | 639291 | 1462893000 | 727470248 | 50% | 1104 | 560 | 100% |
| CGPLBR40 | Breast Cancer | Tumor DNA | Targeted NGS | 150 | 639291 | 1265950500 | 761635668 | 60% | 1154 | 457 | 100% |
| CGPLBR44 | Breast Cancer | Tumor DNA | Targeted NGS | 150 | 639291 | 759286350 | 357135705 | 47% | 542 | 112 | 100% |
| CGPLBR48 | Breast Cancer | Tumor DNA | Targeted NGS | 150 | 639291 | 1096215750 | 558883146 | 51% | 857 | 289 | 100% |
| CGPLBR49 | Breast Cancer | Tumor DNA | Targeted NGS | 150 | 639291 | 1273922850 | 773715963 | 61% | 1174 | 396 | 100% |

Figure 18C

| | | | | | | | | | | |
|---|---|---|---|---|---|---|---|---|---|---|
| CGPLBR53 | Breast Cancer | Tumor DNA | Targeted NGS | 150 | 639291 | 1543663050 | 928939469 | 60% | 1408 | 651 | 100% |
| CGPLBR55 | Breast Cancer | Tumor DNA | Targeted NGS | 150 | 639291 | 1281568800 | 786549957 | 61% | 1179 | 544 | 100% |
| CGPLBR57 | Breast Cancer | Tumor DNA | Targeted NGS | 150 | 639291 | 1014856550 | 514492195 | 51% | 787 | 218 | 100% |
| CGPLBR59 | Breast Cancer | Tumor DNA | Targeted NGS | 150 | 639291 | 1502988750 | 722936771 | 48% | 1075 | 206 | 100% |
| CGPLBR63 | Breast Cancer | Tumor DNA | Targeted NGS | 150 | 639291 | 1265950500 | 761635668 | 60% | 1354 | 457 | 100% |
| CGPLBR64 | Breast Cancer | Tumor DNA | Targeted NGS | 150 | 639291 | 1511564550 | 760271556 | 50% | 1137 | 119 | 100% |
| CGPLBR66 | Breast Cancer | Tumor DNA | Targeted NGS | 150 | 639291 | 1263813900 | 736742733 | 58% | 1119 | 626 | 100% |
| CGPLBR67 | Breast Cancer | Tumor DNA | Targeted NGS | 150 | 639291 | 1218949500 | 732812428 | 60% | 1112 | 326 | 100% |
| CGPLBR68 | Breast Cancer | Tumor DNA | Targeted NGS | 150 | 639291 | 1,320,628,050 | 797,283,712 | 60% | 1215 | 649 | 100% |
| CGPLBR69 | Breast Cancer | Tumor DNA | Targeted NGS | 150 | 639291 | 1254192750 | 670305026 | 53% | 1016 | 331 | 100% |
| CGPLBR70 | Breast Cancer | Tumor DNA | Targeted NGS | 150 | 639291 | 985165050 | 518233636 | 53% | 789 | 284 | 100% |
| CGPLBR71 | Breast Cancer | Tumor DNA | Targeted NGS | 150 | 639291 | 1408808850 | 841106831 | 60% | 1273 | 525 | 100% |
| CGPLBR72 | Breast Cancer | Tumor DNA | Targeted NGS | 150 | 639291 | 1980049200 | 1206509350 | 61% | 1829 | 494 | 100% |
| CGPLBR73 | Breast Cancer | Tumor DNA | Targeted NGS | 150 | 639291 | 511075500 | 289986972 | 57% | 446 | 316 | 100% |
| CGPLBR74 | Breast Cancer | Tumor DNA | Targeted NGS | 150 | 639291 | 1444542150 | 831504089 | 58% | 1266 | 520 | 100% |
| CGPLBR75 | Breast Cancer | Tumor DNA | Targeted NGS | 150 | 639291 | 1209742200 | 615931952 | 51% | 926 | 418 | 100% |
| CGPLBR76 | Breast Cancer | Tumor DNA | Targeted NGS | 150 | 639291 | 1404856200 | 808020500 | 58% | 1222 | 300 | 100% |
| CGPLBR77 | Breast Cancer | Tumor DNA | Targeted NGS | 150 | 639291 | 1297056000 | 507301668 | 39% | 770 | 356 | 100% |
| CGPLBR80 | Breast Cancer | Tumor DNA | Targeted NGS | 150 | 639291 | 1744826850 | 861765758 | 49% | 1264 | 384 | 100% |
| CGPLBR82 | Breast Cancer | Tumor DNA | Targeted NGS | 150 | 639291 | 1162764150 | 528197785 | 45% | 795 | 347 | 100% |
| CGPLBR83 | Breast Cancer | Tumor DNA | Targeted NGS | 150 | 639291 | NA | NA | NA | NA | NA | NA |
| CGPLBR86 | Breast Cancer | Tumor DNA | Targeted NGS | 150 | 639291 | 1374528450 | 752315631 | 55% | 1136 | 226 | 100% |
| CGPLBR87 | Breast Cancer | Tumor DNA | Targeted NGS | 150 | 639291 | 918553500 | 175004835 | 19% | 265 | 157 | 100% |
| CGPLBR88 | Breast Cancer | Tumor DNA | Targeted NGS | 150 | 639291 | 1068209550 | 551606147 | 52% | 846 | 394 | 100% |
| CGPLBR91 | Breast Cancer | Tumor DNA | Targeted NGS | 150 | 639291 | 1115092650 | 563337213 | 51% | 865 | 391 | 100% |
| CGPLBR92 | Breast Cancer | Tumor DNA | Targeted NGS | 150 | 639291 | 1231916700 | 741434698 | 60% | 1136 | 478 | 100% |
| CGPLBR96 | Breast Cancer | Tumor DNA | Targeted NGS | 150 | 639291 | 1012740950 | 545472202 | 54% | 834 | 327 | 100% |
| CGPLBR97 | Breast Cancer | Tumor DNA | Targeted NGS | 150 | 639291 | 1081210050 | 602942749 | 56% | 916 | 373 | 100% |
| CGPLBR99 | Breast Cancer | Tumor DNA | Targeted NGS | 150 | 639291 | 601828650 | 322598549 | 54% | 496 | 312 | 100% |
| CGCRC291 | Colorectal Cancer | Tumor DNA | Targeted NGS | 150 | 639291 | 1012582500 | 454866080 | 45% | 696 | 448 | 100% |
| CGCRC292 | Colorectal Cancer | Tumor DNA | Targeted NGS | 150 | 639291 | 1053966700 | 467350094 | 44% | 711 | 456 | 100% |
| CGCRC293 | Colorectal Cancer | Tumor DNA | Targeted NGS | 150 | 639291 | 962764950 | 424030808 | 44% | 647 | 422 | 100% |
| CGCRC294 | Colorectal Cancer | Tumor DNA | Targeted NGS | 150 | 639291 | 1028456550 | 439156889 | 43% | 669 | 450 | 100% |
| CGCRC295 | Colorectal Cancer | Tumor DNA | Targeted NGS | 150 | 639291 | 928288500 | 421984627 | 45% | 644 | 423 | 100% |
| CGCRC296 | Colorectal Cancer | Tumor DNA | Targeted NGS | 150 | 639291 | 796948200 | 343513710 | 43% | 524 | 344 | 100% |
| CGCRC297 | Colorectal Cancer | Tumor DNA | Targeted NGS | 150 | 639291 | 816835050 | 294168635 | 36% | 448 | 299 | 100% |
| CGCRC298 | Colorectal Cancer | Tumor DNA | Targeted NGS | 150 | 639291 | 864069900 | 404835020 | 47% | 621 | 396 | 100% |
| CGCRC299 | Colorectal Cancer | Tumor DNA | Targeted NGS | 150 | 639291 | 1020461700 | 424930722 | 42% | 643 | 439 | 100% |
| CGCRC300 | Colorectal Cancer | Tumor DNA | Targeted NGS | 150 | 639291 | 831117750 | 368422619 | 44% | 564 | 376 | 100% |
| CGCRC301 | Colorectal Cancer | Tumor DNA | Targeted NGS | 150 | 639291 | 973842300 | 423804347 | 44% | 650 | 404 | 100% |
| CGCRC302 | Colorectal Cancer | Tumor DNA | Targeted NGS | 150 | 639291 | 1115477250 | 483033596 | 43% | 739 | 466 | 100% |
| CGCRC303 | Colorectal Cancer | Tumor DNA | Targeted NGS | 150 | 639291 | 1176646650 | 493560885 | 42% | 756 | 490 | 100% |
| CGCRC304 | Colorectal Cancer | Tumor DNA | Targeted NGS | 150 | 639291 | 1057360350 | 445316428 | 42% | 881 | 441 | 100% |
| CGCRC305 | Colorectal Cancer | Tumor DNA | Targeted NGS | 150 | 639291 | 986335800 | 418119189 | 42% | 634 | 406 | 100% |
| CGCRC306 | Colorectal Cancer | Tumor DNA | Targeted NGS | 150 | 639291 | 895480950 | 384530177 | 43% | 589 | 373 | 100% |
| CGCRC307 | Colorectal Cancer | Tumor DNA | Targeted NGS | 150 | 639291 | 939545250 | 417034584 | 44% | 637 | 419 | 100% |
| CGCRC308 | Colorectal Cancer | Tumor DNA | Targeted NGS | 150 | 639291 | 1074720000 | 457076684 | 43% | 699 | 421 | 100% |
| CGCRC309 | Colorectal Cancer | Tumor DNA | Targeted NGS | 150 | 639291 | 1077028800 | 468056542 | 43% | 712 | 456 | 100% |
| CGCRC310 | Colorectal Cancer | Tumor DNA | Targeted NGS | 150 | 639291 | 1456285350 | 624050285 | 43% | 953 | 602 | 100% |
| CGCRC311 | Colorectal Cancer | Tumor DNA | Targeted NGS | 150 | 639291 | 1046356050 | 469927791 | 45% | 719 | 461 | 100% |
| CGCRC312 | Colorectal Cancer | Tumor DNA | Targeted NGS | 150 | 639291 | 1045012450 | 452684790 | 43% | 693 | 445 | 100% |
| CGCRC313 | Colorectal Cancer | Tumor DNA | Targeted NGS | 150 | 639291 | 1357397850 | 594057235 | 44% | 894 | 571 | 100% |
| CGCRC314 | Colorectal Cancer | Tumor DNA | Targeted NGS | 150 | 639291 | 1059318450 | 470533351 | 44% | 720 | 451 | 100% |
| CGCRC315 | Colorectal Cancer | Tumor DNA | Targeted NGS | 150 | 639291 | 1329922500 | 668919352 | 50% | 1022 | 633 | 100% |
| CGCRC316 | Colorectal Cancer | Tumor DNA | Targeted NGS | 150 | 639291 | 1008207750 | 469494561 | 47% | 715 | 473 | 100% |
| CGCRC317 | Colorectal Cancer | Tumor DNA | Targeted NGS | 150 | 639291 | 1107316250 | 560348663 | 51% | 855 | 552 | 100% |
| CGCRC318 | Colorectal Cancer | Tumor DNA | Targeted NGS | 150 | 639291 | 1434731100 | 691861596 | 48% | 1050 | 669 | 100% |
| CGCRC319 | Colorectal Cancer | Tumor DNA | Targeted NGS | 150 | 639291 | 1258206600 | 610731063 | 49% | 950 | 624 | 100% |
| CGCRC320 | Colorectal Cancer | Tumor DNA | Targeted NGS | 150 | 639291 | 1067872350 | 538856991 | 50% | 815 | 514 | 100% |
| CGCRC321 | Colorectal Cancer | Tumor DNA | Targeted NGS | 150 | 639291 | 1134618650 | 514924981 | 46% | 785 | 499 | 100% |
| CGCRC332 | Colorectal Cancer | Tumor DNA | Targeted NGS | 150 | 639291 | 1274461350 | 744251805 | 58% | 1135 | 508 | 100% |
| CGCRC333 | Colorectal Cancer | Tumor DNA | Targeted NGS | 150 | 639291 | 1407707550 | 796386336 | 57% | 1212 | 501 | 100% |
| CGCRC334 | Colorectal Cancer | Tumor DNA | Targeted NGS | 150 | 639291 | 1236847050 | 701921622 | 57% | 1076 | 507 | 100% |
| CGCRC335 | Colorectal Cancer | Tumor DNA | Targeted NGS | 150 | 639291 | 1123386600 | 441750380 | 39% | 675 | 340 | 100% |
| CGCRC336 | Colorectal Cancer | Tumor DNA | Targeted NGS | 150 | 639291 | 1112596650 | 647572679 | 58% | 995 | 495 | 100% |
| CGCRC337 | Colorectal Cancer | Tumor DNA | Targeted NGS | 150 | 639291 | 1206110850 | 665588725 | 55% | 997 | 574 | 100% |
| CGCRC338 | Colorectal Cancer | Tumor DNA | Targeted NGS | 150 | 639291 | 1156258950 | 519228652 | 45% | 780 | 361 | 100% |
| CGCRC339 | Colorectal Cancer | Tumor DNA | Targeted NGS | 150 | 639291 | NA | NA | NA | NA | NA | NA |
| CGCRC340 | Colorectal Cancer | Tumor DNA | Targeted NGS | 150 | 639291 | 1056358800 | 500654866 | 47% | 761 | 363 | 100% |
| CGCRC341 | Colorectal Cancer | Tumor DNA | Targeted NGS | 150 | 639291 | 1171364850 | 618828014 | 53% | 947 | 496 | NA |
| CGPLLU1 | Lung Cancer | Tumor DNA | Targeted NGS | 150 | 639291 | 1689013800 | 769286196 | 46% | 1152 | 721 | 100% |
| CGPLLU115 | Lung Cancer | Tumor DNA | Targeted NGS | 150 | 639291 | 1249447950 | 555225070 | 44% | 842 | 534 | 100% |
| CGPLLU116 | Lung Cancer | Tumor DNA | Targeted NGS | 150 | 639291 | 1226021550 | 543715026 | 44% | 826 | 520 | 100% |
| CGPLLU117 | Lung Cancer | Tumor DNA | Targeted NGS | 150 | 639291 | 1346899650 | 607087256 | 45% | 924 | 448 | 100% |
| CGPLLU118 | Lung Cancer | Tumor DNA | Targeted NGS | 150 | 639291 | 1541356200 | 667852108 | 43% | 1007 | 667 | 100% |
| CGPLLU119 | Lung Cancer | Tumor DNA | Targeted NGS | 150 | 639291 | 1248963650 | 509020204 | 41% | 770 | 513 | 100% |
| CGPLLU135 | Lung Cancer | Tumor DNA | Targeted NGS | 150 | 639291 | 1340064900 | 618218568 | 46% | 939 | 554 | 100% |
| CGPLLU136 | Lung Cancer | Tumor DNA | Targeted NGS | 150 | 639291 | 802359600 | 428240472 | 53% | 650 | 165 | 100% |
| CGPLLU137 | Lung Cancer | Tumor DNA | Targeted NGS | 150 | 639291 | 1363517850 | 612337794 | 45% | 933 | 594 | 100% |
| CGPLLU138 | Lung Cancer | Tumor DNA | Targeted NGS | 150 | 639291 | 1504663500 | 842387976 | 56% | 1277 | 720 | 100% |
| CGPLLU139 | Lung Cancer | Tumor DNA | Targeted NGS | 150 | 639291 | 1390145700 | 801181359 | 58% | 1207 | 650 | 100% |
| CGPLLU144 | Lung Cancer | Tumor DNA | Targeted NGS | 150 | 639291 | 1200200250 | 549449256 | 46% | 830 | 401 | 100% |
| CGPLLU146 | Lung Cancer | Tumor DNA | Targeted NGS | 150 | 639291 | 1116711600 | 390267100 | 35% | 592 | 383 | 100% |
| CGPLLU147 | Lung Cancer | Tumor DNA | Targeted NGS | 150 | 639291 | 808104900 | 399673367 | 49% | 608 | 388 | 100% |
| CGPLLU162 | Lung Cancer | Tumor DNA | Targeted NGS | 150 | 639291 | 1334133150 | 732531538 | 55% | 1111 | 619 | 100% |
| CGPLLU163 | Lung Cancer | Tumor DNA | Targeted NGS | 150 | 639291 | 1,352,545,050 | 696,512,666 | 51% | 1020 | 583 | 100% |
| CGPLLU164 | Lung Cancer | Tumor DNA | Targeted NGS | 150 | 639291 | 1305960150 | 678924309 | 52% | 1003 | 598 | 100% |

Figure 18D

| Sample | Cancer | DNA | Method | Read Len | Target | Total Bases | Mapped Bases | % | Mean Cov | Median Cov | % Target |
|---|---|---|---|---|---|---|---|---|---|---|---|
| CGPLLU165 | Lung Cancer | Tumor DNA | Targeted NGS | 150 | 639291 | 1063652400 | 607101865 | 57% | 912 | 211 | 100% |
| CGPLLU166 | Lung Cancer | Tumor DNA | Targeted NGS | 150 | 639291 | NA | NA | NA | NA | NA | NA |
| CGPLLU168 | Lung Cancer | Tumor DNA | Targeted NGS | 150 | 639291 | 1285271400 | 685373694 | 53% | 1037 | 661 | 100% |
| CGPLLU169 | Lung Cancer | Tumor DNA | Targeted NGS | 150 | 639291 | 1285960650 | 685393054 | 53% | 1041 | 666 | 100% |
| CGPLLU174 | Lung Cancer | Tumor DNA | Targeted NGS | 150 | 639291 | 645803700 | 355237091 | 55% | 535 | 350 | 100% |
| CGPLLU175 | Lung Cancer | Tumor DNA | Targeted NGS | 150 | 639291 | 1449611550 | 855214102 | 59% | 1308 | 391 | 100% |
| CGPLLU176 | Lung Cancer | Tumor DNA | Targeted NGS | 150 | 639291 | 1095470850 | 567775337 | 52% | 871 | 434 | 100% |
| CGPLLU177 | Lung Cancer | Tumor DNA | Targeted NGS | 150 | 639291 | 1472590050 | 834893525 | 57% | 1287 | 735 | 100% |
| CGPLLU178 | Lung Cancer | Tumor DNA | Targeted NGS | 150 | 639291 | 1148297400 | 667857382 | 58% | 1030 | 547 | 100% |
| CGPLLU179 | Lung Cancer | Tumor DNA | Targeted NGS | 150 | 639291 | 684354500 | 339072044 | 51% | 515 | 330 | 100% |
| CGPLLU180 | Lung Cancer | Tumor DNA | Targeted NGS | 150 | 639291 | 1086715200 | 600798880 | 55% | 916 | 193 | 100% |
| CGPLLU19 | Lung Cancer | Tumor DNA | Targeted NGS | 150 | 639291 | 1214483550 | 519092020 | 43% | 787 | 315 | 100% |
| CGPLLU197 | Lung Cancer | Tumor DNA | Targeted NGS | 150 | 639291 | 768799800 | 406238720 | 53% | 619 | 111 | 100% |
| CGPLLU198 | Lung Cancer | Tumor DNA | Targeted NGS | 150 | 639291 | NA | NA | NA | NA | NA | NA |
| CGPLLU2 | Lung Cancer | Tumor DNA | Targeted NGS | 150 | 639291 | 1632543150 | 749366432 | 46% | 1128 | 609 | 100% |
| CGPLLU20 | Lung Cancer | Tumor DNA | Targeted NGS | 150 | 639291 | 1150028400 | 506414454 | 44% | 758 | 475 | 100% |
| CGPLLU202 | Lung Cancer | Tumor DNA | Targeted NGS | 150 | 639291 | 1293513600 | 670182891 | 52% | 1023 | 504 | 100% |
| CGPLLU203 | Lung Cancer | Tumor DNA | Targeted NGS | 150 | 639291 | 1198142100 | 596099136 | 50% | 910 | 563 | 100% |
| CGPLLU204 | Lung Cancer | Tumor DNA | Targeted NGS | 150 | 639291 | 661557450 | 348927002 | 53% | 525 | 351 | 100% |
| CGPLLU205 | Lung Cancer | Tumor DNA | Targeted NGS | 150 | 639291 | 1259501400 | 676224830 | 54% | 1028 | 545 | 100% |
| CGPLLU206 | Lung Cancer | Tumor DNA | Targeted NGS | 150 | 639291 | 936519600 | 84546885 | 9% | 129 | 78 | 100% |
| CGPLLU207 | Lung Cancer | Tumor DNA | Targeted NGS | 150 | 639291 | 1122284550 | 498538490 | 44% | 759 | 438 | 100% |
| CGPLLU208 | Lung Cancer | Tumor DNA | Targeted NGS | 150 | 639291 | 1061510250 | 574889056 | 54% | 882 | 370 | 100% |
| CGPLLU209 | Lung Cancer | Tumor DNA | Targeted NGS | 150 | 639291 | 1041774600 | 505999221 | 49% | 770 | 406 | 100% |
| CGPLLU21 | Lung Cancer | Tumor DNA | Targeted NGS | 150 | 639291 | 1301333700 | 584929403 | 45% | 894 | 523 | 100% |
| CGPLLU22 | Lung Cancer | Tumor DNA | Targeted NGS | 150 | 639291 | 1223740200 | 573490645 | 47% | 870 | 427 | 100% |
| CGPLLU23 | Lung Cancer | Tumor DNA | Targeted NGS | 150 | 639291 | 1154575200 | 558261771 | 48% | 855 | 333 | 100% |
| CGPLLU26 | Lung Cancer | Tumor DNA | Targeted NGS | 150 | 639291 | NA | NA | NA | NA | NA | NA |
| CGPLLU28 | Lung Cancer | Tumor DNA | Targeted NGS | 150 | 639291 | 1253304300 | 536280022 | 43% | 809 | 474 | 100% |
| CGPLLU3 | Lung Cancer | Tumor DNA | Targeted NGS | 150 | 639291 | 1283482650 | 587505537 | 46% | 884 | 376 | 100% |
| CGPLLU30 | Lung Cancer | Tumor DNA | Targeted NGS | 150 | 639291 | 534800550 | 247881827 | 46% | 376 | 105 | 100% |
| CGPLLU31 | Lung Cancer | Tumor DNA | Targeted NGS | 150 | 639291 | 1250134500 | 557178929 | 45% | 841 | 426 | 100% |
| CGPLLU5 | Lung Cancer | Tumor DNA | Targeted NGS | 150 | 639291 | 1128982550 | 543920310 | 48% | 823 | 266 | 100% |
| CGPLLU54 | Lung Cancer | Tumor DNA | Targeted NGS | 150 | 639291 | 2039507400 | 891222046 | 45% | 593 | 123 | 100% |
| CGPLLU6 | Lung Cancer | Tumor DNA | Targeted NGS | 150 | 639291 | 1438016400 | 868685187 | 48% | 1013 | 523 | 100% |
| CGPLLU63 | Lung Cancer | Tumor DNA | Targeted NGS | 150 | 639291 | 1,284,084,450 | 536,873,644 | 42% | 816 | 334 | 100% |
| CGPLLU64 | Lung Cancer | Tumor DNA | Targeted NGS | 150 | 639291 | 1415779950 | 574175656 | 41% | 874 | 558 | 100% |
| CGPLLU65 | Lung Cancer | Tumor DNA | Targeted NGS | 150 | 639291 | 1226734500 | 555791782 | 45% | 841 | 299 | 100% |
| CGPLLU66 | Lung Cancer | Tumor DNA | Targeted NGS | 150 | 639291 | 1498678200 | 638138245 | 43% | 968 | 547 | 100% |
| CGPLLU67 | Lung Cancer | Tumor DNA | Targeted NGS | 150 | 639291 | 1148746200 | 492136159 | 43% | 747 | 388 | 100% |
| CGPLOV1 | Ovarian Cancer | Tumor DNA | Targeted NGS | 150 | 639291 | 1325971850 | 581484681 | 44% | 880 | 416 | 100% |
| CGPLOV10 | Ovarian Cancer | Tumor DNA | Targeted NGS | 150 | 639291 | 1252083750 | 539790788 | 43% | 821 | 350 | 100% |
| CGPLOV11 | Ovarian Cancer | Tumor DNA | Targeted NGS | 150 | 639291 | 1225968550 | 534800567 | 44% | 813 | 238 | 100% |
| CGPLOV13 | Ovarian Cancer | Tumor DNA | Targeted NGS | 150 | 639291 | 1330495800 | 655509142 | 49% | 993 | 414 | 100% |
| CGPLOV14 | Ovarian Cancer | Tumor DNA | Targeted NGS | 150 | 639291 | 1297177950 | 591287827 | 46% | 894 | 541 | 100% |
| CGPLOV15 | Ovarian Cancer | Tumor DNA | Targeted NGS | 150 | 639291 | 1150070300 | 452437890 | 39% | 692 | 378 | 100% |
| CGPLOV16 | Ovarian Cancer | Tumor DNA | Targeted NGS | 150 | 639291 | 968859000 | 495142955 | 51% | 754 | 202 | 100% |
| CGPLOV17 | Ovarian Cancer | Tumor DNA | Targeted NGS | 150 | 639291 | 1315764700 | 713860251 | 54% | 1089 | 500 | 100% |
| CGPLOV18 | Ovarian Cancer | Tumor DNA | Targeted NGS | 150 | 639291 | 891364900 | 557764532 | 63% | 853 | 197 | 100% |
| CGPLOV19 | Ovarian Cancer | Tumor DNA | Targeted NGS | 150 | 639291 | 1233679450 | 672750957 | 54% | 1023 | 327 | 100% |
| CGPLOV2 | Ovarian Cancer | Tumor DNA | Targeted NGS | 150 | 639291 | 1286955600 | 606105596 | 47% | 916 | 297 | 100% |
| CGPLOV20 | Ovarian Cancer | Tumor DNA | Targeted NGS | 150 | 639291 | 1163796600 | 632169517 | 54% | 964 | 430 | 100% |
| CGPLOV21 | Ovarian Cancer | Tumor DNA | Targeted NGS | 150 | 639291 | 1373819100 | 743538836 | 54% | 1136 | 341 | 100% |
| CGPLOV22 | Ovarian Cancer | Tumor DNA | Targeted NGS | 150 | 639291 | 1316281800 | 696435612 | 53% | 1061 | 408 | 100% |
| CGPLOV3 | Ovarian Cancer | Tumor DNA | Targeted NGS | 150 | 639291 | 1661075700 | 780726926 | 47% | 1173 | 581 | 100% |
| CGPLOV6 | Ovarian Cancer | Tumor DNA | Targeted NGS | 150 | 639291 | 1453338900 | 778245944 | 54% | 1187 | 307 | 100% |
| CGPLOV7 | Ovarian Cancer | Tumor DNA | Targeted NGS | 150 | 639291 | 1415413950 | 681644124 | 48% | 1017 | 429 | 100% |
| CGPLOV8 | Ovarian Cancer | Tumor DNA | Targeted NGS | 150 | 639291 | 1546324800 | 782429622 | 51% | 1169 | 545 | 100% |
| CGPLOV9 | Ovarian Cancer | Tumor DNA | Targeted NGS | 150 | 639291 | 1346789400 | 603639598 | 45% | 919 | 596 | 100% |
| CGPLBR100 | Breast Cancer | Germline DNA | Targeted NGS | 150 | 639291 | 587752350 | 303296797 | 52% | 466 | 316 | 100% |
| CGPLBR38 | Breast Cancer | Germline DNA | Targeted NGS | 150 | 639291 | 607162800 | 295989325 | 49% | 453 | 312 | 100% |
| CGPLBR39 | Breast Cancer | Germline DNA | Targeted NGS | 150 | 639291 | 536928000 | 258238473 | 48% | 395 | 284 | 100% |
| CGPLBR40 | Breast Cancer | Germline DNA | Targeted NGS | 150 | 639291 | 504208500 | 270658416 | 54% | 410 | 298 | 100% |
| CGPLBR44 | Breast Cancer | Germline DNA | Targeted NGS | 150 | 639291 | 574791000 | 316417055 | 55% | 484 | 331 | 100% |
| CGPLBR48 | Breast Cancer | Germline DNA | Targeted NGS | 150 | 639291 | 635913150 | 357101607 | 56% | 547 | 387 | 100% |
| CGPLBR49 | Breast Cancer | Germline DNA | Targeted NGS | 150 | 639291 | 594631950 | 337522575 | 57% | 512 | 347 | 100% |
| CGPLBR53 | Breast Cancer | Germline DNA | Targeted NGS | 150 | 639291 | 588261000 | 341304903 | 58% | 518 | 348 | 100% |
| CGPLBR55 | Breast Cancer | Germline DNA | Targeted NGS | 150 | 639291 | 428455950 | 119796448 | 28% | 180 | 117 | 100% |
| CGPLBR57 | Breast Cancer | Germline DNA | Targeted NGS | 150 | 639291 | 549441900 | 314057412 | 57% | 481 | 330 | 100% |
| CGPLBR59 | Breast Cancer | Germline DNA | Targeted NGS | 150 | 639291 | 677024100 | 354381703 | 52% | 537 | 346 | 100% |
| CGPLBR63 | Breast Cancer | Germline DNA | Targeted NGS | 150 | 639291 | 504208500 | 270658416 | 54% | 410 | 298 | 100% |
| CGPLBR64 | Breast Cancer | Germline DNA | Targeted NGS | 150 | 639291 | 413363850 | 193561159 | 47% | 291 | 186 | 100% |
| CGPLBR66 | Breast Cancer | Germline DNA | Targeted NGS | 150 | 639291 | 603047250 | 339194896 | 56% | 513 | 366 | 100% |
| CGPLBR67 | Breast Cancer | Germline DNA | Targeted NGS | 150 | 639291 | 699562950 | 409741164 | 59% | 623 | 410 | 100% |
| CGPLBR68 | Breast Cancer | Germline DNA | Targeted NGS | 150 | 639291 | 672427650 | 353985085 | 53% | 539 | 332 | 100% |
| CGPLBR69 | Breast Cancer | Germline DNA | Targeted NGS | 150 | 639291 | 591797550 | 327570487 | 55% | 500 | 349 | 100% |
| CGPLBR70 | Breast Cancer | Germline DNA | Targeted NGS | 150 | 639291 | 552791700 | 315920897 | 57% | 483 | 335 | 100% |
| CGPLBR71 | Breast Cancer | Germline DNA | Targeted NGS | 150 | 639291 | 675318450 | 386958218 | 57% | 591 | 389 | 100% |
| CGPLBR72 | Breast Cancer | Germline DNA | Targeted NGS | 150 | 639291 | 381478350 | 195921864 | 51% | 295 | 181 | 100% |
| CGPLBR73 | Breast Cancer | Germline DNA | Targeted NGS | 150 | 639291 | 1061212350 | 537918502 | 51% | 824 | 229 | 100% |
| CGPLBR74 | Breast Cancer | Germline DNA | Targeted NGS | 150 | 639291 | 696478500 | 204182619 | 29% | 311 | 218 | 100% |
| CGPLBR75 | Breast Cancer | Germline DNA | Targeted NGS | 150 | 639291 | 658538550 | 242257252 | 37% | 370 | 244 | 100% |
| CGPLBR76 | Breast Cancer | Germline DNA | Targeted NGS | 150 | 639291 | 409580550 | 161155508 | 39% | 236 | 148 | 100% |
| CGPLBR77 | Breast Cancer | Germline DNA | Targeted NGS | 150 | 639291 | 537431700 | 305330922 | 57% | 470 | 332 | 100% |
| CGPLBR80 | Breast Cancer | Germline DNA | Targeted NGS | 150 | 639291 | 610652400 | 273064709 | 45% | 413 | 269 | 100% |
| CGPLBR82 | Breast Cancer | Germline DNA | Targeted NGS | 150 | 639291 | 721861350 | 404540286 | 56% | 616 | 393 | 100% |
| CGPLBR83 | Breast Cancer | Germline DNA | Targeted NGS | 150 | 639291 | NA | NA | NA | NA | NA | NA |

Figure 18E

| | | | | | | | | | | |
|---|---|---|---|---|---|---|---|---|---|---|
| CGPLBR86 | Breast Cancer | Germline DNA | Targeted NGS | 150 | 639291 | 365127450 | 175449534 | 48% | 256 | 165 | 100% |
| CGPLBR87 | Breast Cancer | Germline DNA | Targeted NGS | 150 | 639291 | 825919350 | 324734673 | 52% | 493 | 305 | 100% |
| CGPLBR88 | Breast Cancer | Germline DNA | Targeted NGS | 150 | 639291 | 474856950 | 101788416 | 21% | 156 | 108 | 100% |
| CGPLBR91 | Breast Cancer | Germline DNA | Targeted NGS | 150 | 639291 | 649309800 | 260265354 | 40% | 397 | 292 | 100% |
| CGPLBR92 | Breast Cancer | Germline DNA | Targeted NGS | 150 | 639291 | 614417400 | 332144854 | 54% | 505 | 301 | 100% |
| CGPLBR96 | Breast Cancer | Germline DNA | Targeted NGS | 150 | 639291 | 601662300 | 226863862 | 38% | 347 | 245 | 100% |
| CGPLBR97 | Breast Cancer | Germline DNA | Targeted NGS | 150 | 639291 | 635832150 | 330334979 | 52% | 505 | 339 | 100% |
| CGPLBR99 | Breast Cancer | Germline DNA | Targeted NGS | 150 | 639291 | 1114707300 | 583697712 | 52% | 892 | 438 | 100% |
| CGCRC291 | Colorectal Cancer | Germline DNA | Targeted NGS | 150 | 639291 | 1074846000 | 479885292 | 45% | 733 | 485 | 100% |
| CGCRC292 | Colorectal Cancer | Germline DNA | Targeted NGS | 150 | 639291 | 997109550 | 448775788 | 45% | 685 | 452 | 100% |
| CGCRC293 | Colorectal Cancer | Germline DNA | Targeted NGS | 150 | 639291 | 956307150 | 428412364 | 45% | 653 | 427 | 100% |
| CGCRC294 | Colorectal Cancer | Germline DNA | Targeted NGS | 150 | 639291 | 941706900 | 399120498 | 42% | 609 | 410 | 100% |
| CGCRC295 | Colorectal Cancer | Germline DNA | Targeted NGS | 150 | 639291 | 1045862700 | 456802680 | 44% | 697 | 469 | 100% |
| CGCRC296 | Colorectal Cancer | Germline DNA | Targeted NGS | 150 | 639291 | 726412050 | 329483654 | 45% | 503 | 338 | 100% |
| CGCRC297 | Colorectal Cancer | Germline DNA | Targeted NGS | 150 | 639291 | 686847900 | 305825261 | 45% | 467 | 313 | 100% |
| CGCRC298 | Colorectal Cancer | Germline DNA | Targeted NGS | 150 | 639291 | 915267600 | 391756000 | 43% | 601 | 401 | 100% |
| CGCRC299 | Colorectal Cancer | Germline DNA | Targeted NGS | 150 | 639291 | 962294850 | 410283252 | 43% | 622 | 414 | 100% |
| CGCRC300 | Colorectal Cancer | Germline DNA | Targeted NGS | 150 | 639291 | 1086992200 | 464279410 | 43% | 711 | 464 | 100% |
| CGCRC301 | Colorectal Cancer | Germline DNA | Targeted NGS | 150 | 639291 | 915540150 | 400988996 | 44% | 615 | 414 | 100% |
| CGCRC302 | Colorectal Cancer | Germline DNA | Targeted NGS | 150 | 639291 | 811854000 | 351266173 | 43% | 538 | 359 | 100% |
| CGCRC303 | Colorectal Cancer | Germline DNA | Targeted NGS | 150 | 639291 | 1060418400 | 442109304 | 42% | 676 | 446 | 100% |
| CGCRC304 | Colorectal Cancer | Germline DNA | Targeted NGS | 150 | 639291 | 1007139450 | 431385782 | 43% | 660 | 433 | 100% |
| CGCRC305 | Colorectal Cancer | Germline DNA | Targeted NGS | 150 | 639291 | 1246122600 | 632083848 | 51% | 957 | 623 | 100% |
| CGCRC306 | Colorectal Cancer | Germline DNA | Targeted NGS | 150 | 639291 | 1018205250 | 425416271 | 42% | 651 | 415 | 100% |
| CGCRC307 | Colorectal Cancer | Germline DNA | Targeted NGS | 150 | 639291 | 913508250 | 387133404 | 42% | 591 | 396 | 100% |
| CGCRC308 | Colorectal Cancer | Germline DNA | Targeted NGS | 150 | 639291 | 938120700 | 425166128 | 45% | 651 | 419 | 100% |
| CGCRC309 | Colorectal Cancer | Germline DNA | Targeted NGS | 150 | 639291 | 1025337600 | 447153051 | 44% | 679 | 443 | 100% |
| CGCRC310 | Colorectal Cancer | Germline DNA | Targeted NGS | 150 | 639291 | 980782650 | 427168989 | 44% | 648 | 419 | 100% |
| CGCRC311 | Colorectal Cancer | Germline DNA | Targeted NGS | 150 | 639291 | 846414300 | 367848055 | 43% | 563 | 373 | 100% |
| CGCRC312 | Colorectal Cancer | Germline DNA | Targeted NGS | 150 | 639291 | 1045262100 | 465476158 | 45% | 712 | 454 | 100% |
| CGCRC313 | Colorectal Cancer | Germline DNA | Targeted NGS | 150 | 639291 | 1411402200 | 622602217 | 44% | 934 | 597 | 100% |
| CGCRC314 | Colorectal Cancer | Germline DNA | Targeted NGS | 150 | 639291 | 948293550 | 408431471 | 43% | 625 | 409 | 100% |
| CGCRC315 | Colorectal Cancer | Germline DNA | Targeted NGS | 150 | 639291 | 944269800 | 470119319 | 50% | 714 | 469 | 100% |
| CGCRC316 | Colorectal Cancer | Germline DNA | Targeted NGS | 150 | 639291 | 1102555350 | 549138041 | 50% | 837 | 551 | 100% |
| CGCRC317 | Colorectal Cancer | Germline DNA | Targeted NGS | 150 | 639291 | 1099990350 | 547860243 | 50% | 825 | 542 | 100% |
| CGCRC318 | Colorectal Cancer | Germline DNA | Targeted NGS | 150 | 639291 | 990188550 | 489300022 | 49% | 746 | 483 | 100% |
| CGCRC319 | Colorectal Cancer | Germline DNA | Targeted NGS | 150 | 639291 | 1098523800 | 536937209 | 49% | 816 | 533 | 100% |
| CGCRC320 | Colorectal Cancer | Germline DNA | Targeted NGS | 150 | 639291 | 881784300 | 449537819 | 51% | 680 | 431 | 100% |
| CGCRC321 | Colorectal Cancer | Germline DNA | Targeted NGS | 150 | 639291 | 1068635550 | 502245626 | 47% | 768 | 486 | 100% |
| CGCRC332 | Colorectal Cancer | Germline DNA | Targeted NGS | 150 | 639291 | 758356050 | 406546836 | 54% | 621 | 354 | 100% |
| CGCRC333 | Colorectal Cancer | Germline DNA | Targeted NGS | 150 | 639291 | 560436600 | 241285888 | 43% | 368 | 225 | 100% |
| CGCRC334 | Colorectal Cancer | Germline DNA | Targeted NGS | 150 | 639291 | 562592100 | 287288732 | 51% | 439 | 304 | 100% |
| CGCRC335 | Colorectal Cancer | Germline DNA | Targeted NGS | 150 | 639291 | 733030800 | 391132272 | 53% | 596 | 355 | 100% |
| CGCRC336 | Colorectal Cancer | Germline DNA | Targeted NGS | 150 | 639291 | 450245550 | 228507680 | 51% | 351 | 246 | 100% |
| CGCRC337 | Colorectal Cancer | Germline DNA | Targeted NGS | 150 | 639291 | 457483050 | 216548896 | 47% | 330 | 228 | 100% |
| CGCRC338 | Colorectal Cancer | Germline DNA | Targeted NGS | 150 | 639291 | 654071250 | 285478494 | 44% | 434 | 257 | 100% |
| CGCRC339 | Colorectal Cancer | Germline DNA | Targeted NGS | 150 | 639291 | NA | NA | NA | NA | NA | NA |
| CGCRC340 | Colorectal Cancer | Germline DNA | Targeted NGS | 150 | 639291 | 579149550 | 234017537 | 40% | 356 | 234 | 100% |
| CGPLLU1 | Lung Cancer | Germline DNA | Targeted NGS | 150 | 639291 | 677237100 | 268756748 | 40% | 408 | 289 | 100% |
| CGPLLU115 | Lung Cancer | Germline DNA | Targeted NGS | 150 | 639291 | 673939500 | 254019687 | 38% | 386 | 263 | 100% |
| CGPLLU116 | Lung Cancer | Germline DNA | Targeted NGS | 150 | 639291 | 536485350 | 194819603 | 36% | 296 | 210 | 100% |
| CGPLLU117 | Lung Cancer | Germline DNA | Targeted NGS | 150 | 639291 | 562698450 | 214221603 | 38% | 327 | 227 | 100% |
| CGPLLU118 | Lung Cancer | Germline DNA | Targeted NGS | 150 | 639291 | 824984250 | 340283945 | 41% | 515 | 353 | 100% |
| CGPLLU119 | Lung Cancer | Germline DNA | Targeted NGS | 150 | 639291 | 622004250 | 238879678 | 38% | 362 | 254 | 100% |
| CGPLLU135 | Lung Cancer | Germline DNA | Targeted NGS | 150 | 639291 | 689515950 | 271757497 | 39% | 411 | 282 | 100% |
| CGPLLU136 | Lung Cancer | Germline DNA | Targeted NGS | 150 | 639291 | 570675300 | 226580792 | 40% | 344 | 239 | 100% |
| CGPLLU137 | Lung Cancer | Germline DNA | Targeted NGS | 150 | 639291 | 677915850 | 256959903 | 38% | 390 | 275 | 100% |
| CGPLLU138 | Lung Cancer | Germline DNA | Targeted NGS | 150 | 639291 | 764916750 | 375266555 | 49% | 571 | 390 | 100% |
| CGPLLU139 | Lung Cancer | Germline DNA | Targeted NGS | 150 | 639291 | 680111250 | 353773681 | 52% | 532 | 197 | 100% |
| CGPLLU144 | Lung Cancer | Germline DNA | Targeted NGS | 150 | 639291 | 695037000 | 361563821 | 52% | 550 | 366 | 100% |
| CGPLLU146 | Lung Cancer | Germline DNA | Targeted NGS | 150 | 639291 | 608225100 | 316448889 | 52% | 483 | 274 | 100% |
| CGPLLU147 | Lung Cancer | Germline DNA | Targeted NGS | 150 | 639291 | 1174428600 | 536650801 | 46% | 808 | 517 | 100% |
| CGPLLU162 | Lung Cancer | Germline DNA | Targeted NGS | 150 | 639291 | 429361300 | 151297004 | 35% | 226 | 188 | 100% |
| CGPLLU163 | Lung Cancer | Germline DNA | Targeted NGS | 150 | 639291 | 524,208,300 | 200,482,808 | 38% | 301 | 236 | 100% |
| CGPLLU164 | Lung Cancer | Germline DNA | Targeted NGS | 150 | 639291 | 509906100 | 220862753 | 43% | 322 | 241 | 100% |
| CGPLLU165 | Lung Cancer | Germline DNA | Targeted NGS | 150 | 639291 | 535155150 | 224433873 | 42% | 328 | 150 | 100% |
| CGPLLU166 | Lung Cancer | Germline DNA | Targeted NGS | 150 | 639291 | NA | NA | NA | NA | NA | NA |
| CGPLLU168 | Lung Cancer | Germline DNA | Targeted NGS | 150 | 639291 | 510783000 | 285892642 | 56% | 438 | 164 | 100% |
| CGPLLU169 | Lung Cancer | Germline DNA | Targeted NGS | 150 | 639291 | 591105000 | 300994824 | 51% | 457 | 326 | 100% |
| CGPLLU174 | Lung Cancer | Germline DNA | Targeted NGS | 150 | 639291 | 2072868200 | 1190204964 | 57% | 1786 | 303 | 100% |
| CGPLLU175 | Lung Cancer | Germline DNA | Targeted NGS | 150 | 639291 | 618550950 | 339691335 | 55% | 517 | 358 | 100% |
| CGPLLU176 | Lung Cancer | Germline DNA | Targeted NGS | 150 | 639291 | 610189200 | 337041659 | 55% | 516 | 332 | 100% |
| CGPLLU177 | Lung Cancer | Germline DNA | Targeted NGS | 150 | 639291 | 659891250 | 372266268 | 56% | 566 | 373 | 100% |
| CGPLLU178 | Lung Cancer | Germline DNA | Targeted NGS | 150 | 639291 | 694574700 | 380911029 | 55% | 577 | 380 | 100% |
| CGPLLU179 | Lung Cancer | Germline DNA | Targeted NGS | 150 | 639291 | 1535136750 | 925596393 | 60% | 1405 | 341 | 100% |
| CGPLLU180 | Lung Cancer | Germline DNA | Targeted NGS | 150 | 639291 | 1498872600 | 781889116 | 52% | 1190 | 639 | 100% |
| CGPLLU19 | Lung Cancer | Germline DNA | Targeted NGS | 150 | 639291 | 591053700 | 223344073 | 38% | 341 | 172 | 100% |
| CGPLLU197 | Lung Cancer | Germline DNA | Targeted NGS | 150 | 639291 | 491469750 | 173279191 | 35% | 266 | 132 | 100% |
| CGPLLU198 | Lung Cancer | Germline DNA | Targeted NGS | 150 | 639291 | 571152750 | 243139384 | 43% | 369 | 259 | 100% |
| CGPLLU2 | Lung Cancer | Germline DNA | Targeted NGS | 150 | 639291 | 499588050 | 197204704 | 39% | 300 | 221 | 100% |
| CGPLLU20 | Lung Cancer | Germline DNA | Targeted NGS | 150 | 639291 | 574141350 | 228443607 | 40% | 347 | 248 | 100% |
| CGPLLU202 | Lung Cancer | Germline DNA | Targeted NGS | 150 | 639291 | 645258450 | 207925335 | 32% | 316 | 209 | 100% |
| CGPLLU203 | Lung Cancer | Germline DNA | Targeted NGS | 150 | 639291 | 557531850 | 297213725 | 53% | 453 | 303 | 100% |
| CGPLLU204 | Lung Cancer | Germline DNA | Targeted NGS | 150 | 639291 | 1178585700 | 582456480 | 49% | 883 | 341 | 100% |
| CGPLLU205 | Lung Cancer | Germline DNA | Targeted NGS | 150 | 639291 | 704826750 | 297031777 | 42% | 453 | 294 | 100% |
| CGPLLU206 | Lung Cancer | Germline DNA | Targeted NGS | 150 | 639291 | 587897550 | 260243234 | 44% | 396 | 265 | 100% |
| CGPLLU207 | Lung Cancer | Germline DNA | Targeted NGS | 150 | 639291 | 635760000 | 252119850 | 40% | 384 | 263 | 100% |

Figure 18F

| | | | | | | | | | | | |
|---|---|---|---|---|---|---|---|---|---|---|---|
| CGPLLU208 | Lung Cancer | Germline DNA | Targeted NGS | 150 | 639291 | 549011700 | 306386280 | 56% | 472 | 327 | 100% |
| CGPLLU209 | Lung Cancer | Germline DNA | Targeted NGS | 150 | 639291 | 578241150 | 293725997 | 51% | 450 | 302 | 100% |
| CGPLLU21 | Lung Cancer | Germline DNA | Targeted NGS | 150 | 639291 | 589913250 | 196975420 | 33% | 301 | 223 | 100% |
| CGPLLU22 | Lung Cancer | Germline DNA | Targeted NGS | 150 | 639291 | 745022400 | 191886179 | 26% | 291 | 211 | 100% |
| CGPLLU23 | Lung Cancer | Germline DNA | Targeted NGS | 150 | 639291 | 621765750 | 243401140 | 39% | 373 | 224 | 100% |
| CGPLLU26 | Lung Cancer | Germline DNA | Targeted NGS | 150 | 639291 | 826125900 | 249126153 | 30% | 361 | 268 | 100% |
| CGPLLU28 | Lung Cancer | Germline DNA | Targeted NGS | 150 | 639291 | 642068100 | 269574172 | 42% | 407 | 321 | 100% |
| CGPLLU3 | Lung Cancer | Germline DNA | Targeted NGS | 150 | 639291 | 600536700 | 243416472 | 41% | 371 | 195 | 100% |
| CGPLLU30 | Lung Cancer | Germline DNA | Targeted NGS | 150 | 639291 | 592419600 | 254080805 | 43% | 384 | 289 | 100% |
| CGPLLU31 | Lung Cancer | Germline DNA | Targeted NGS | 150 | 639291 | 658089150 | 222043822 | 34% | 334 | 231 | 100% |
| CGPLLU5 | Lung Cancer | Germline DNA | Targeted NGS | 150 | 639291 | 566575050 | 218275022 | 39% | 332 | 241 | 100% |
| CGPLLU54 | Lung Cancer | Germline DNA | Targeted NGS | 150 | 639291 | 324943500 | 108468275 | 33% | 167 | 122 | 100% |
| CGPLLU6 | Lung Cancer | Germline DNA | Targeted NGS | 150 | 639291 | 498756750 | 194335181 | 39% | 295 | 224 | 100% |
| CGPLLU63 | Lung Cancer | Germline DNA | Targeted NGS | 150 | 639291 | 667,879,450 | 309,382,277 | 46% | 470 | 280 | 100% |
| CGPLLU64 | Lung Cancer | Germline DNA | Targeted NGS | 150 | 639291 | 652960200 | 296973185 | 45% | 450 | 309 | 100% |
| CGPLLU65 | Lung Cancer | Germline DNA | Targeted NGS | 150 | 639291 | 656203200 | 256082240 | 39% | 387 | 271 | 100% |
| CGPLLU66 | Lung Cancer | Germline DNA | Targeted NGS | 150 | 639291 | 600045150 | 239464814 | 40% | 363 | 250 | 100% |
| CGPLLU67 | Lung Cancer | Germline DNA | Targeted NGS | 150 | 639291 | 596848350 | 230461277 | 39% | 348 | 242 | 100% |
| CGPLOV1 | Ovarian Cancer | Germline DNA | Targeted NGS | 150 | 639291 | 739803600 | 260650215 | 35% | 394 | 254 | 100% |
| CGPLOV10 | Ovarian Cancer | Germline DNA | Targeted NGS | 150 | 639291 | 639810000 | 321433448 | 50% | 487 | 334 | 100% |
| CGPLOV11 | Ovarian Cancer | Germline DNA | Targeted NGS | 150 | 639291 | 703802550 | 353128590 | 50% | 536 | 359 | 100% |
| CGPLOV13 | Ovarian Cancer | Germline DNA | Targeted NGS | 150 | 639291 | 818085300 | 401086839 | 49% | 607 | 389 | 100% |
| CGPLOV14 | Ovarian Cancer | Germline DNA | Targeted NGS | 150 | 639291 | 791921100 | 385336443 | 49% | 583 | 403 | 100% |
| CGPLOV15 | Ovarian Cancer | Germline DNA | Targeted NGS | 150 | 639291 | 701500350 | 360045925 | 51% | 551 | 360 | 100% |
| CGPLOV16 | Ovarian Cancer | Germline DNA | Targeted NGS | 150 | 639291 | 734391000 | 314221694 | 43% | 480 | 237 | 100% |
| CGPLOV17 | Ovarian Cancer | Germline DNA | Targeted NGS | 150 | 639291 | 734076450 | 345696639 | 47% | 529 | 357 | 100% |
| CGPLOV18 | Ovarian Cancer | Germline DNA | Targeted NGS | 150 | 639291 | 583473150 | 302593210 | 52% | 463 | 317 | 100% |
| CGPLOV19 | Ovarian Cancer | Germline DNA | Targeted NGS | 150 | 639291 | 653914950 | 257169658 | 39% | 393 | 254 | 100% |
| CGPLOV2 | Ovarian Cancer | Germline DNA | Targeted NGS | 150 | 639291 | 750964800 | 323423781 | 43% | 488 | 309 | 100% |
| CGPLOV20 | Ovarian Cancer | Germline DNA | Targeted NGS | 150 | 639291 | 589255200 | 291459229 | 49% | 443 | 316 | 100% |
| CGPLOV21 | Ovarian Cancer | Germline DNA | Targeted NGS | 150 | 639291 | 540460950 | 262969134 | 49% | 401 | 274 | 100% |
| CGPLOV22 | Ovarian Cancer | Germline DNA | Targeted NGS | 150 | 639291 | 588115950 | 289776487 | 49% | 443 | 297 | 100% |
| CGPLOV3 | Ovarian Cancer | Germline DNA | Targeted NGS | 150 | 639291 | 565973400 | 199491765 | 35% | 296 | 193 | 100% |
| CGPLOV6 | Ovarian Cancer | Germline DNA | Targeted NGS | 150 | 639291 | 778602000 | 297048515 | 38% | 452 | 296 | 100% |
| CGPLOV7 | Ovarian Cancer | Germline DNA | Targeted NGS | 150 | 639291 | 680537300 | 211116154 | 31% | 316 | 208 | 100% |
| CGPLOV8 | Ovarian Cancer | Germline DNA | Targeted NGS | 150 | 639291 | 555609900 | 288758931 | 52% | 443 | 232 | 100% |
| CGPLOV9 | Ovarian Cancer | Germline DNA | Targeted NGS | 150 | 639291 | 558193200 | 276211572 | 49% | 413 | 235 | 100% |

*NA denotes data not available.

Table S8. Summary of CRC patient outcomes

| Patient | Patient Type | Analysis Type | Stage at Diagnosis | Maximum Mutant Allele Fraction (TEC-Seq) | Progression-free Survival (0 - Progression-free ; 1 - Progression) | Time to Progression-free Survival (months) | Overall Survival (0 - Alive ; 1 - Dead of disease) | Time to Overall Survival (months) | CEA (ng/ml) | Smoking status |
|---|---|---|---|---|---|---|---|---|---|---|
| CGCRC291 | Colorectal Cancer | TEC-Seq and Targeted NGS | IV | 22.85% | 1 | 21.10 | 1 | 25.87 | 2.10 | Non-smoker |
| CGCRC292 | Colorectal Cancer | TEC-Seq and Targeted NGS | IV | 1.41% | 0 | 32.07 | 0 | 32.07 | 8.90 | Non-smoker |
| CGCRC293 | Colorectal Cancer | TEC-Seq and Targeted NGS | IV | 0.35% | 0 | 2.67 | 0 | 2.67 | 23.00 | Non-smoker |
| CGCRC294 | Colorectal Cancer | TEC-Seq and Targeted NGS | III | 0.17% | 0 | 31.37 | 0 | 31.37 | 2.90 | Non-smoker |
| CGCRC295 | Colorectal Cancer | TEC-Seq and Targeted NGS | IV | 2.26% | 1 | 7.43 | 1 | 19.00 | No Data | Non-smoker |
| CGCRC296 | Colorectal Cancer | TEC-Seq and Targeted NGS | II | 0.00% | 0 | 31.00 | 0 | 31.00 | 3.50 | Former-smoker |
| CGCRC297 | Colorectal Cancer | TEC-Seq and Targeted NGS | III | 0.00% | 0 | 30.83 | 0 | 30.83 | 2.70 | Former-smoker |
| CGCRC298 | Colorectal Cancer | TEC-Seq and Targeted NGS | II | 0.55% | 0 | 30.80 | 0 | 30.80 | 3.40 | Non-smoker |
| CGCRC299 | Colorectal Cancer | TEC-Seq and Targeted NGS | I | 0.00% | 0 | 30.43 | 0 | 30.43 | 4.80 | Non-smoker |
| CGCRC300 | Colorectal Cancer | TEC-Seq and Targeted NGS | I | 0.00% | 0 | 30.40 | 0 | 30.40 | 3.50 | Non-smoker |
| CGCRC301 | Colorectal Cancer | TEC-Seq and Targeted NGS | III | 0.21% | 0 | 30.37 | 0 | 30.37 | No Data | Current-smoker |
| CGCRC302 | Colorectal Cancer | TEC-Seq and Targeted NGS | II | 0.12% | 0 | 9.53 | 0 | 9.53 | 2.50 | Former-smoker |
| CGCRC303 | Colorectal Cancer | TEC-Seq and Targeted NGS | III | 0.08% | 0 | 30.13 | 0 | 30.13 | 19.00 | Non-smoker |
| CGCRC304 | Colorectal Cancer | TEC-Seq and Targeted NGS | III | 0.27% | 1 | 22.73 | 1 | 28.90 | 2.40 | Former-smoker |
| CGCRC305 | Colorectal Cancer | TEC-Seq and Targeted NGS | II | 0.19% | 0 | 29.20 | 0 | 29.20 | 1.80 | Non-smoker |
| CGCRC306 | Colorectal Cancer | TEC-Seq and Targeted NGS | II | 8.02% | 1 | 11.43 | 1 | 11.57 | 39.00 | Non-smoker |
| CGCRC307 | Colorectal Cancer | TEC-Seq and Targeted NGS | II | 0.56% | 1 | 24.17 | 0 | 24.17 | 37.00 | Non-smoker |
| CGCRC308 | Colorectal Cancer | TEC-Seq and Targeted NGS | III | 0.11% | 0 | 28.80 | 0 | 28.80 | 116.00 | Current-smoker |
| CGCRC309 | Colorectal Cancer | TEC-Seq and Targeted NGS | II | 3.00% | 1 | 7.03 | 1 | 7.67 | 1.90 | Non-smoker |
| CGCRC310 | Colorectal Cancer | TEC-Seq and Targeted NGS | III | 0.15% | 0 | 28.57 | 0 | 28.57 | 3.80 | Former-smoker |
| CGCRC311 | Colorectal Cancer | TEC-Seq and Targeted NGS | I | 0.00% | 0 | 28.43 | 0 | 28.43 | 1.60 | Non-smoker |
| CGCRC312 | Colorectal Cancer | TEC-Seq and Targeted NGS | III | 0.59% | 0 | 28.27 | 0 | 28.27 | 2.50 | Current-smoker |
| CGCRC313 | Colorectal Cancer | TEC-Seq and Targeted NGS | III | 0.17% | 0 | 28.00 | 0 | 28.00 | 18.00 | Former-smoker |
| CGCRC314 | Colorectal Cancer | TEC-Seq and Targeted NGS | I | 0.38% | 0 | 27.63 | 0 | 27.63 | 4.00 | Former-smoker |
| CGCRC315 | Colorectal Cancer | TEC-Seq and Targeted NGS | III | 0.27% | 0 | 27.63 | 0 | 27.63 | 1.50 | Non-smoker |
| CGCRC316 | Colorectal Cancer | TEC-Seq and Targeted NGS | III | 6.52% | 0 | 27.17 | 0 | 27.17 | 8.40 | Non-smoker |
| CGCRC317 | Colorectal Cancer | TEC-Seq and Targeted NGS | III | 0.36% | 0 | 27.17 | 0 | 27.17 | 6.40 | Non-smoker |
| CGCRC318 | Colorectal Cancer | TEC-Seq and Targeted NGS | I | 0.00% | 0 | 26.93 | 0 | 26.93 | 1.90 | Non-smoker |
| CGCRC319 | Colorectal Cancer | TEC-Seq and Targeted NGS | III | 0.13% | 0 | 26.83 | 0 | 26.83 | 5.30 | Non-smoker |
| CGCRC320 | Colorectal Cancer | TEC-Seq and Targeted NGS | I | 0.64% | 0 | 26.90 | 0 | 26.90 | 3.10 | Former-smoker |
| CGCRC321 | Colorectal Cancer | TEC-Seq and Targeted NGS | I | 0.20% | 0 | 26.17 | 0 | 26.17 | 2.40 | Non-smoker |

Figure 22

DETECTION OF CANCER

CROSS-REFERENCE TO RELATED APPLICATIONS

This application is a 35 U.S.C. § 371 U.S. national entry of International Application PCT/US18/030905, having an International filing date of May 3, 2018, which claims the benefit of U.S. Provisional Application Ser. No. 62/501,686 filed May 4, 2017 and 62/516,009 and filed on Jun. 6, 2017, the entire contents of these applications are incorporated herein by reference in their entirety.

INCORPORATION BY REFERENCE OF SEQUENCE LISTING

The contents of the text file named "04807-002WO1-SequenceListing.TXT", which was created on Aug. 11, 2018, and is 1,062 bytes in size, are hereby incorporated by reference in their entireties and for all purposes.

BACKGROUND

Early detection and intervention are likely to be the most effective means for reducing morbidity and mortality of human cancer. However, development of methods for non-invasive detection of early stage tumors has remained a challenge.

Over 14 million individuals are diagnosed with cancer world-wide, with the majority having invasive or metastatic disease (1). A large number of studies have established that much of the morbidity and mortality in human cancer is related to the late diagnosis of this disease where surgical and pharmacologic therapies are less effective (2). Unfortunately, clinically proven biomarkers that can be used to diagnose and guide patient management early in the course of disease are available for only a limited number of patients. Serum-based protein biomarkers such as carcinoma antigen-125 (CA-125), carcinoembryonic antigen (CEA), prostate-specific antigen (PSA), and cancer antigen 19-9 (CA 19-9) are commonly used for monitoring cancer patients, but as these proteins are also found in the serum of individuals without cancer, they are typically not useful for disease diagnosis (3-7). Other approaches for early detection of cancer, such as stool-based molecular tests or colonoscopies, are limited to individual tumor types and have challenges in patient compliance (8, 9). Currently, no widely-applicable biomarkers have been developed for broad detection of human cancer.

The development of non-invasive liquid biopsy methods based on the analysis of cell free DNA provides the opportunity for a new generation of diagnostic approaches. Although cell-free DNA in the circulation was first described over fifty years ago (10), abnormalities in cancer patients were observed only decades later (11, 12) and showed that such individuals have higher levels of cell-free DNA. In patients with cancer, a fraction of cell-free DNA is tumor derived and is termed circulating tumor DNA. Analysis of circulating tumor DNA has the advantage of identifying alterations that are exquisitely specific to the tumor. The application of next-generation sequencing (NGS) together with advanced computational methods has recently allowed circulating tumor DNA-based tumor genotyping in a variety of cancer types (13-21). However, these approaches have largely been utilized in patients with late stage cancers or have used tumor tissue sequencing to guide mutational analyses in the blood.

SUMMARY

The present disclosure relates generally to methods of detecting cancer. Provided herein are methods of detecting circulating tumor DNA, cancer cell mutations, and/or cancer cells harboring one or more mutations. In some embodiments, methods provided herein include detecting one or more genetic alterations in cell-free DNA. In some embodiments, methods provided herein for detecting one or more genetic alterations in cell-free DNA can be performed when the subject is not known to harbor a cancer cell and/or a cancer cell mutation (e.g., when the subject is not known to harbor a cancer cell having the cancer cell mutation).

In some aspects, provided herein are methods for identifying the presence of circulating tumor DNA in a subject, comprising: detecting one or more genetic alterations in cell-free DNA in a biological sample isolated from the subject, wherein the step of detecting is performed when the subject is not known to harbor a cancer cell, and identifying the presence of circulating tumor DNA when at least one of the detected genetic alterations in the cell-free DNA is a cancer cell mutation. In some embodiments, the biological sample can be isolated from subject. In some embodiments, the biological sample is, or can include, blood, plasma, urine, cerebrospinal fluid, saliva, sputum, broncho-alveolar lavage, bile, lymphatic fluid, cyst fluid, stool, ascites, and combinations thereof. In some embodiments, the presence of circulating tumor DNA can indicate the presence of a cancer cell. In some embodiments, the cancer cell mutation can be present in a gene listed in Table S7. In some embodiments, the cancer cell mutation can be one or more of the somatic alterations listed in Table S7. In some embodiments, the step of detecting one or more genetic alterations in cell-free DNA can include using a method selected from the group consisting of: a targeted capture method, a next-generation sequencing method, and an array-based method, and combinations thereof. In some embodiments, the step of detecting one or more genetic alterations in cell-free DNA can include using a method comprising steps of: extracting cell-free DNA from blood, ligating a low complexity pool of dual index barcode adapters to the cell-free DNA to generate a plurality of barcode adapter-ligated cell-free DNA segments, capturing the plurality of barcode adapter-ligated cell-free DNA segments, sequencing the plurality of captured barcode adapter-ligated cell-free DNA segments, aligning the sequenced plurality of captured barcode adapter-ligated cell-free DNA segments to a reference genome, and identifying sequence alterations using aligned sequences of multiple distinct molecules containing identical redundant changes. In some embodiments, the cell-free DNA in the biological sample can be present in an amount less than about 1500 ng. In some embodiments, the circulating tumor DNA in the biological sample can be present in an amount less than about 2%. In some embodiments, the presence of circulating tumor DNA can be detected at a time period prior to diagnosis of the subject with an early-stage cancer. In some embodiments, the presence of the circulating tumor DNA can be detected at a time period when the subject has not been diagnosed with a stage II cancer, has not been diagnosed with a stage I cancer, has not had a biopsy to confirm abnormal cellular growth, has not had a biopsy to confirm the presence of a tumor, has not undergone a diagnostic scan to detect a cancer, or any combination thereof. In some embodiments, the cancer cell mutation can be present in the DNA of a cancer cell in the subject (e.g., a lung cancer cell, an ovarian cancer cell, a breast cancer cell, or a colorectal cancer cell). In some embodiments, the cancer cell mutation is not a blood cell proliferation mutation (e.g., a blood cell proliferation mutation listed in Table S5) or germline alteration (e.g., a germline alteration listed in Table S6). In some embodiments, a therapeutic intervention can be administered to the subject (e.g., a therapeutic intervention is selected from the group consisting of: adoptive T cell therapy, radiation therapy, surgery, administration of a chemotherapeutic agent, administration of an immune checkpoint inhibitor, administration of a targeted therapy, administration of a kinase inhibitor, administration of a signal transduction inhibitor, administration of a bispecific antibody, administration of a monoclonal antibody, and combinations thereof). In some embodiments, the therapeutic intervention can be administered at a time when the subject has an early-stage cancer, and wherein the therapeutic intervention is more effective that if the therapeutic intervention were to be administered to a subject at a later time.

In some aspects, provided herein are methods for identifying the presence of a cancer cell in a subject, comprising: detecting one or more genetic alterations in cell-free DNA in a biological sample isolated from the subject, wherein the step of detecting is performed when the subject is not known to harbor a cancer cell, identifying the presence of circulating tumor DNA when at least one of the detected genetic alterations in the cell-free DNA is a cancer cell mutation, and identifying the presence of the cancer cell when the presence of circulating tumor DNA is identified. In some embodiments, the biological sample can be isolated from subject. In some embodiments, the biological sample is, or can include, blood, plasma, urine, cerebrospinal fluid, saliva, sputum, broncho-alveolar lavage, bile, lymphatic fluid, cyst fluid, stool, ascites, and combinations thereof. In some embodiments, the cancer cell mutation can be present in a gene listed in Table S7. In some embodiments, the cancer cell mutation can be one or more of the somatic alterations listed in Table S7. In some embodiments, the step of detecting one or more genetic alterations in cell-free DNA can include using a method selected from the group consisting of: a targeted capture method, a next-generation sequencing method, and an array-based method, and combinations thereof. In some embodiments, the step of detecting one or more genetic alterations in cell-free DNA can include using a method comprising steps of: extracting cell-free DNA from blood, ligating a low complexity pool of dual index barcode adapters to the cell-free DNA to generate a plurality of barcode adapter-ligated cell-free DNA segments, capturing the plurality of barcode adapter-ligated cell-free DNA segments, sequencing the plurality of captured barcode adapter-ligated cell-free DNA segments, aligning the sequenced plurality of captured barcode adapter-ligated cell-free DNA segments to a reference genome, and identifying sequence alterations using aligned sequences of multiple distinct molecules containing identical redundant changes. In some embodiments, the cell-free DNA in the biological sample can be present in an amount less than about 1500 ng. In some embodiments, the circulating tumor DNA in the biological sample can be present in an amount less than about 2%. In some embodiments, the presence of circulating tumor DNA can be detected at a time period prior to diagnosis of the subject with an early-stage cancer. In some embodiments, the presence of the circulating tumor DNA can be detected at a time period when the subject has not been diagnosed with a stage II cancer, has not been diagnosed with a stage I cancer, has not had a biopsy to confirm abnormal cellular growth, has not had a biopsy to confirm the presence of a tumor, has not undergone a diagnostic scan to detect a cancer, or any combination thereof. In some embodiments, the cancer cell mutation can be present in the DNA of a cancer cell in the subject (e.g., a lung cancer cell, an ovarian cancer cell, a breast cancer cell, or a colorectal cancer cell). In some embodiments, the cancer cell mutation is not a blood cell proliferation mutation (e.g., a blood cell proliferation mutation listed in Table S5) or germline alteration (e.g., a germline alteration listed in Table S6). In some embodiments, a therapeutic intervention can be administered to the subject (e.g., a therapeutic intervention is selected from the group consisting of: adoptive T cell therapy, radiation therapy, surgery, administration of a chemotherapeutic agent, administration of an immune checkpoint inhibitor, administration of a targeted therapy, administration of a kinase inhibitor, administration of a signal transduction inhibitor, administration of a bispecific antibody, administration of a monoclonal antibody, and combinations thereof). In some embodiments, the therapeutic intervention can be administered at a time when the subject has an early-stage cancer, and wherein the therapeutic intervention is more effective that if the therapeutic intervention were to be administered to a subject at a later time.

In some aspects, provided herein are methods for detecting a blood cell proliferation mutation in a subject, comprising: detecting one or more genetic alterations in cell-free DNA in a biological sample isolated from the subject, wherein the step of detecting is performed when the subject is not known to harbor the blood cell proliferation mutation, and identifying the presence of a blood cell proliferation mutation when at least one of the detected genetic alterations in the cell-free DNA is a blood cell proliferation mutation. In some embodiments, the one or more detected genetic alterations can include an alteration listed in Table S5.

In some aspects, provided herein are methods for detecting a blood cell proliferation disorder in a subject, comprising: detecting one or more genetic alterations in cell-free DNA in a biological sample isolated from the subject, wherein the step of detecting is performed when the subject is not known to harbor the blood cell proliferation disorder, identifying the presence of a blood cell proliferation mutation when at least one of the detected genetic alterations in the cell-free DNA is a blood cell proliferation mutation, and identifying the presence of the blood cell proliferation disorder when the presence of the blood cell proliferation mutation is identified. In some embodiments, the one or more detected genetic alterations can include an alteration listed in Table S5.

In some aspects, provided herein are methods for detecting a germline alteration in a subject, comprising: detecting one or more genetic alterations in cell-free DNA in a biological sample isolated from the subject, wherein the step of detecting is performed when the subject is not known to harbor the germline alteration, and identifying the presence of a germline alteration when at least one of the detected genetic alterations in the cell-free DNA is a germline alteration. In some embodiments, the one or more detected genetic alterations can include an alteration listed in Table S6.

In some aspects, provided herein are methods for distinguishing subtypes of cell-free DNA in a subject, comprising: detecting one or more genetic alterations in cell-free DNA in a biological sample isolated from the subject, and (i) identifying the presence of circulating tumor DNA, the presence of a cancer cell mutation, or the presence of a cancer cell when at least one of the detected genetic alterations in the cell-free DNA is a cancer cell mutation, (ii) identifying the presence of a blood cell proliferation mutation or the presence of a blood cell proliferation disorder in the subject when at least one of the detected genetic alterations in the cell-free DNA is a blood cell proliferation mutation, or (iii) identifying the presence of a germline alteration in the subject when at least one of the detected genetic alterations in the cell-free DNA is a germline alteration.

In some aspects, provided herein are methods for determining a poor prognosis in a subject having cancer (e.g., colorectal cancer), comprising: identifying the level of circulating tumor DNA present a sample isolated from the subject, and determining that the subject has a poor prognosis when the level of circulating tumor DNA is higher than a reference level of circulating tumor DNA. In some embodiments, identifying the level of circulating tumor DNA present in the subject can include determining the amount of cell-free DNA that comprises one or more genetic alterations in a biological sample isolated from the subject. In some embodiments, the one or more genetic alterations can include an alteration listed in Table S7. In some embodiments, the poor prognosis is selected from the group consisting of: shorter progression-free survival, lower overall survival, and combinations thereof.

In some aspects, provided herein are methods for determining a poor prognosis in a subject having cancer (e.g., colorectal cancer), comprising: identifying the level of cell-free DNA present in the subject, and determining that the subject has a poor prognosis when the identified level of cell-free DNA is higher than a reference level of cell-free DNA. In some embodiments, the identified level of cell-free DNA in the subject can about 2-fold higher than a reference level of cell-free DNA. In some embodiments, the identified level of cell-free DNA in the subject can about 3-fold higher than a reference level of cell-free DNA. In some embodiments, the identified level of cell-free DNA in the subject can about 4-fold higher than a reference level of cell-free DNA. In some embodiments, the identified level of cell-free DNA in the subject can about 6-fold higher than a reference level of cell-free DNA. In some embodiments, the identified level of cell-free DNA in the subject can about 10-fold higher than a reference level of cell-free DNA. In some embodiments, the poor prognosis is selected from the group consisting of: shorter progression-free survival, lower overall survival, and combinations thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 15. Table S1: Genes analyzed by TEC-Seq.
FIG. 16. Table S2: Summary of TEC-Seq validation.
FIG. 17. Table S3: Summary of patients analyzed.
FIG. 18. Table S4: Summary of genomic analyses.
FIG. 19. Table S5: Alterations in blood cell proliferation genes in healthy individuals and cancer patients.
FIG. 20. Table S6: Germline alterations identified in cell-free DNA.
FIG. 21. Table S7: Somatic alterations detected in cell-free DNA of cancer patients.
FIG. 22. Table S8: Summary of CRC patient outcomes.

DETAILED DESCRIPTION

Figure 1:
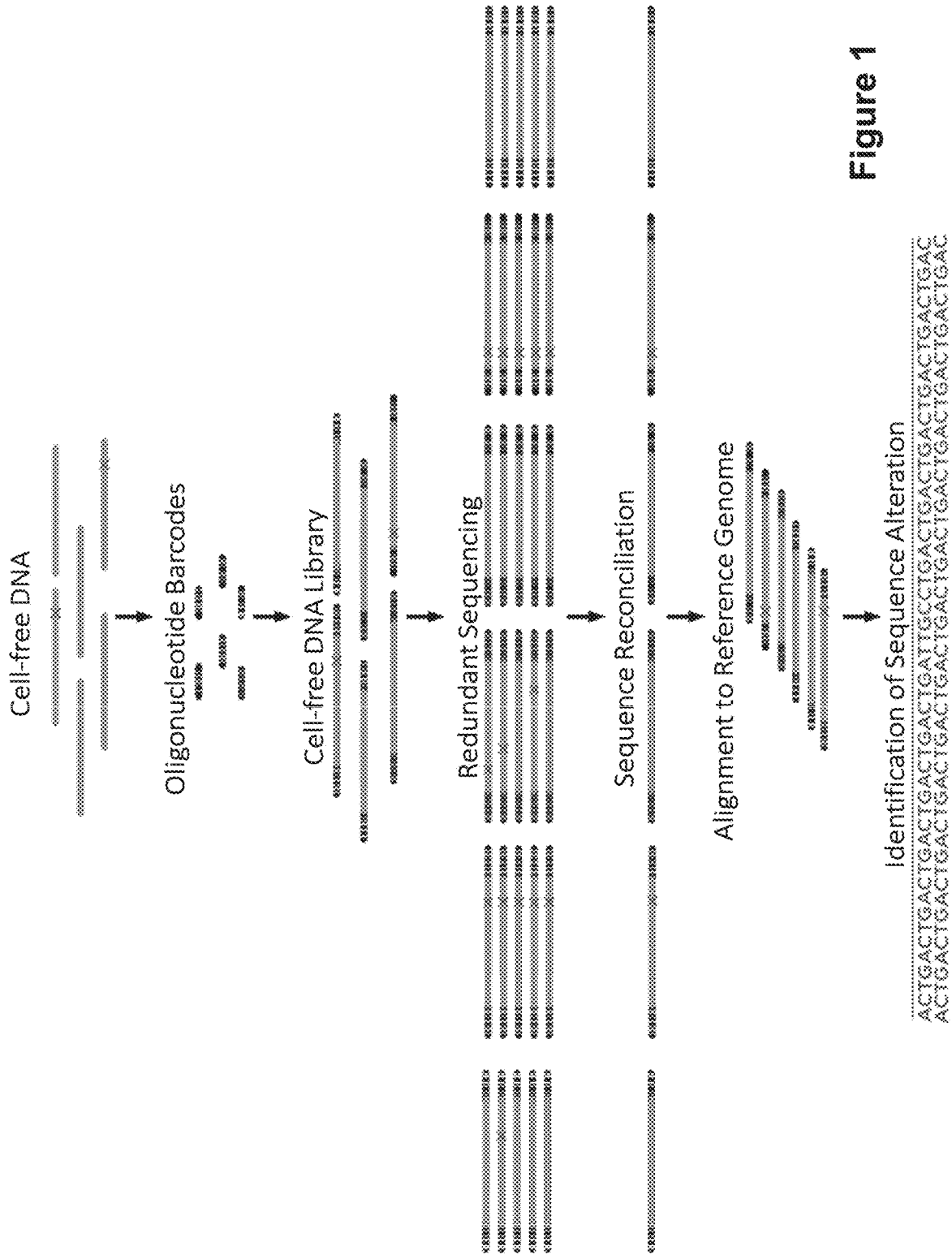
FIG. 1. Schematic of TEC-Seq method. Cell-free DNA is extracted from blood and converted to a genomic library through ligation of a low complexity pool of dual index barcode adapters. The resulting cell-free DNA library is captured and redundantly sequenced to produce multiple duplicates of each DNA fragment. Sequence reconciliation among duplicate fragments identifies alterations present in identical DNA molecule with the same start and end position and exogenous barcodes. Alignment to the reference genome of multiple distinct molecules containing identical redundant changes is used to identify bona fide alterations.

Methods disclosed herein provide a broadly applicable approach for non-invasive direct detection of patients with early-stage cancer. Methods disclosed herein for improved detection of cancer (e.g., circulating tumor DNA or cancer cells harboring a cancer cell mutation) provide certain benefits in that detectable alterations in cell-free DNA are by definition clonal and therefore indicate an underlying population of cells with identical somatic mutations. Methods disclosed herein provide a high degree of specificity for detecting circulating tumor DNA compared to other blood-based biomarkers, which may be elevated in other normal tissues in patients without cancer.

The de novo identification of somatic alterations has remained a significant challenge for development of early detection approaches (13, 30). Certain analytical performance characteristics of methods provided herein indicate their suitability for such early detection approaches. Methods provided herein can help reduce or eliminate over-diagnoses, since no tumor-derived alterations were identified in plasma of the healthy individuals in our study. Likewise, the concordance between liquid and tumor biopsies using methods provided herein was determined to be high, and indicated that liquid biopsies may have advantages for detection of heterogeneous tumor-specific alterations that may be missed by tissue biopsies or other conventional methods. Imaging and other diagnostic studies can be used in combination with methods provided herein to confirm the tumor of origin. Detection of cancer cell mutations in circulating tumor DNA combined with other molecular characteristics (31) can also be used to identify the source of occult lesions.

The high conversion of cell-free DNA molecules using methods provided herein has increased the number of molecules that can be evaluated through next generation sequencing approaches. The parallel analysis of cancer driver genes using methods provided herein has the advantage of detecting a high fraction of tumors without prior knowledge of the genetic make-up of these cancers. The ability to detect multiple alterations in each case can increase overall sensitivity, even when an individual mutation may not be detected.

The ability to detect a large portion (e.g., half to three quarters) of patients with early-stage cancer (e.g., colorectal, ovarian, lung and/or breast cancer) provides new opportunities for early detection and intervention. The survival difference between late stage and early stage disease in these cancers accounts for over a million lives world-wide each year (1). Circulating tumor DNA-based cancer detection followed by appropriate therapeutic intervention in even a fraction of individuals at earlier stages would likely dwarf the current health impact of most late-stage cancer therapies. Additionally or alternatively, the level and type of circulating tumor DNA at the time of diagnosis can provide additional information related to patient prognosis that may ultimately lead to further therapeutic intervention. Cancer screening efforts based on other molecular tests have been described (32). The methods provided herein can be implemented a broad scale.

As used herein, the word "a" before a noun represents one or more of the particular noun. For example, the phrase "a genetic alteration" encompasses "one or more genetic alterations."

As used herein, the term "about" means approximately, in the region of, roughly, or around. When used in conjunction with a numerical range, the term "about" modifies that range by extending the boundaries above and below the numerical values set forth. In general, the term "about" is used herein to modify a numerical value above and below the stated value by a variance of 10%.

As used herein, the phrase "reference blood cell" refers to a cell circulating in the blood which contains nuclear genetic material in the form of DNA. Examples of reference blood cells include white blood cells which include but are not limited to neutrophils, eosinophils, basophils, lymphocytes, and monocytes.

As used herein, the phrase "blood cell proliferation mutation" refers to a genetic alteration that is present in the DNA of a reference blood cell but is determined not to be a germline alteration. In some embodiments, a blood cell proliferation mutation may exist in a reference blood cell which may lead to a blood cell proliferation disorder. Examples of blood cell proliferation disorders include, without limitation, pre-leukemic hematopoietic proliferation and/or expansion, myelodysplasia, polycythemia vera, myelofibrosis, thrombocythemia, leukemias, and lymphomas. In some embodiments, a blood cell proliferation disorder may lead to a serious and/or life-threatening condition or disease state such as, without limitation, leukemia or lymphoma. In some embodiments, a blood cell proliferation mutation is a point mutation. In some embodiments, a blood cell proliferation mutation is a deletion. In some embodiments, a blood cell proliferation mutation is an insertion. In some embodiments, a blood cell proliferation mutation is a translocation event. In some embodiments, a translocation event results in a gene fusion. In some embodiments, a blood cell proliferation mutation is a structural alteration. In some embodiments, a blood cell proliferation mutation includes a mutation listed in Table S5. For example, blood cell proliferation mutation can be a mutation in DNA Methyltransferase 3 Alpha (DNMT3A), e.g., a mutation that results in a R882C amino acid substitution in DNMT3A.

As used herein, the term "cancer cell mutation" refers to a genetic alteration that has been identified in a reference cancer tissue or cell, or in DNA derived from a reference cancer tissue or cell, including but not limited to tumor cells, circulating tumor cells and/or circulating tumor DNA. Any of a variety of cancer cell mutations can be detected using any of the variety of methods provided herein. For example, a cancer cell mutation can be any of the variety of mutations disclosed in COSMIC, the Catalogue of Somatic Mutations in Cancer, which can be found at the URL cancer.sanger.ac.uk/cosmic. In some embodiments, a cancer cell mutation is a point mutation. In some embodiments, a cancer cell mutation is a deletion. In some embodiments, a cancer cell mutation is an insertion. In some embodiments, a cancer cell mutation is a translocation event that results in a gene fusion. In some embodiments, a cancer cell mutation is a structural alteration. In some embodiments, a cancer cell mutation is a mutation in a gene listed in Table S7. In some embodiments, a cancer cell mutation is a somatic alteration listed in Table S7.

As used herein, the term "germline alteration" refers to a genetic alteration that has been identified as being present in most or all cells of a subject (e.g., a mutation that was present in the germ cells of at least one of the subject's parents, and resulted in a constitutional mutation in the subject). In some embodiments, a germline alteration is present in a heterozygous state (e.g., one of the subject's alleles harbors the germline alteration, while the other is wild-type). In some embodiments, a heterozygous germline alteration can lead to a cancerous state in the subject when a mutation occurs in the conserved and expressed allele while the wild-type copy of the allele is lost, an occurrence commonly referred to as "loss of heterozygosity." In some embodiments, a germline alteration is a point mutation. In some embodiments, a germline alteration is a deletion. In some embodiments, a germline alteration is an insertion. In some embodiments, a germline alteration is a translocation event that results in a gene fusion. In some embodiments, a germline alteration is a structural alteration. In some embodiments, a germline alteration is a mutation in a gene listed in Table S6. In some embodiments, a germline alteration is mutation listed in Table S6.

As used herein, the term "subject" means a vertebrate, including any member of the class mammalia, including humans, domestic and farm animals, and zoo, sports or pet animals, such as mouse, rabbit, pig, sheep, goat, cattle, horse (e.g., race horse), and higher primates. In some embodiments, the subject is a human. In some embodiments, the subject is a human harboring a cancer cell. In some embodiments, the subject is a human harboring a cancer cell, but who is not known to harbor the cancer cell.

Identifying the Presence of Circulating Tumor DNA in a Subject

Provided herein are methods for identifying the presence of circulating tumor DNA in a subject. In some embodiments, methods for identifying the presence of circulating tumor DNA in a subject include detecting one or more genetic alterations in cell-free DNA in a biological sample isolated from the subject, and identifying the presence of circulating tumor DNA where at least one of the detected genetic alterations in the cell-free DNA is a cancer cell mutation. In some embodiments, the step of detecting is performed when the subject is not known to harbor a cancer cell. In some embodiments, the presence of circulating tumor DNA indicates the presence of a cancer cell in the subject (e.g., a cancer cell from any of the exemplary cancers described herein).

In some embodiments, the biological sample is isolated from subject. Any suitable biological sample that contains cell-free DNA can be used in accordance with any of the variety of methods disclosed herein. For example, the biological sample can include blood, plasma, urine, cerebrospinal fluid, saliva, sputum, broncho-alveolar lavage, bile, lymphatic fluid, cyst fluid, stool, ascites, and combinations thereof. Methods of isolating biological samples from a subject are known to those of ordinary skill in the art.

In some embodiments, the step of detecting a genetic alteration (e.g., one or more genetic alterations) in cell-free DNA is performed using one or more of the methods described herein (e.g., a targeted capture method, a next-generation sequencing method, and an array-based method, or any combinations thereof).

In some embodiments, methods provided herein can be used to detect a genetic alteration (e.g., one or more genetic alterations) in circulating tumor DNA present in cell-free DNA, where the cell-free DNA is present in an amount less than about 1500 ng, e.g., less than about 1400 ng, less than about 1300 ng, less than about 1200 ng, less than about 1100 ng, less than about 1000 ng, less than about 900 ng, less than about 800 ng, less than about 700 ng, less than about 600 ng, less than about 500 ng, less than about 400 ng, less than about 300 ng, less than about 200 ng, less than about 150 ng, less than about 100 ng, less than about 95 ng, less than about 90 ng, less than about 85 ng, less than about 80 ng, less than about 75 ng, less than about 70 ng, less than about 65 ng, less than about 60 ng, less than about 55 ng, less than about 50 ng, less than about 45 ng, less than about 40 ng, less than about 35 ng, less than about 30 ng, less than about 25 ng, less than about 20 ng, less than about 15 ng, less than about 10 ng, or less than about 5 ng. In some embodiments, methods provided herein can be used to detect a genetic alteration (e.g., one or more genetic alterations) in circulating tumor DNA present in cell-free DNA, where the circulating tumor DNA represents 100% of the cell-free DNA. In some embodiments, methods provided herein can be used to detect a genetic alteration (e.g., one or more genetic alterations) in circulating tumor DNA present in cell-free DNA, where the circulating tumor DNA represents less than 100% of the cell-free DNA, e.g. about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, about 0.95%, about 0.90%, about 0.85%, about 0.80%, about 0.75%, about 0.70%, about 0.65%, about 0.60%, about 0.55%, about 0.50%, about 0.45%, about 0.40%, about 0.35%, about 0.30%, about 0.25%, about 0.20%, about 0.15%, about 0.10%, about 0.09%, about 0.08%, about 0.07%, about 0.06%, about 0.05% of the cell-free DNA, or less.

In some embodiments, methods provided herein can be used to detect the presence of circulating tumor DNA at a time period prior to diagnosis of the subject with an early-stage cancer. For example, methods provided herein can be used when a subject has not been diagnosed with cancer and/or when a subject is not known to harbor a cancer cell.

In some embodiments, a cancer cell mutation that is detected by any of the variety of methods disclosed herein is present in a cancer cell present in the subject. For example, a cancer cell mutation listed in Table S7 that is detected using any of the variety of methods disclosed herein can be present in a cancer cell present in the subject. In some embodiments, a cancer cell mutation detected by any of the variety of methods disclosed herein is confirmed to be present in a cancer cell present in the subject through further diagnostic testing (e.g., diagnostic scans, biopsies, molecular-based techniques to confirm the presence of the cancer cell mutation, or any of the other diagnostic testing methods disclosed herein or known in the art).

In some embodiments, a cancer cell mutation that is detected by any of the variety of methods disclosed herein can be different from a blood proliferative disorder mutation or germline alteration (e.g., the cancer cell mutation is not a blood proliferative disorder mutation or germline alteration). For example, a cancer cell mutation that is detected by any of the variety of methods disclosed herein can be different from a blood proliferative disorder mutation in a gene listed in Table S5, or different from a blood proliferative disorder mutation listed in Table S5. Additionally or alternatively, a cancer cell mutation that is detected by any of the variety of methods disclosed herein can be different from a germline alteration in a gene listed in Table S6, or different from a germline alteration listed in Table S6.

In some embodiments, a therapeutic intervention is administered to the subject after a cancer cell mutation is detected. Any of the therapeutic interventions disclosed herein or known in the art can be administered.

In some embodiments, methods provided herein can be used to identify the presence of circulating tumor DNA in a subject at a time period prior to diagnosis of the subject with an early-stage cancer (e.g., when the subject is not known to harbor a cancer cell), after which a therapeutic intervention (e.g., any of the therapeutic interventions described herein) can be administered to the subject. In some embodiments, methods provided herein can be used to determine that a subject has an early-stage cancer before other methods (e.g., conventional diagnostic methods) are capable of determining the presence of cancer. In some embodiments, a therapeutic intervention administered to a subject that is determined to have an early-stage cancer using any of the variety of methods provided herein is more effective that if the therapeutic intervention were to be administered to a subject at a later time (e.g., after the cancer has progressed beyond early-stage). In some embodiments, a therapeutic intervention administered to a subject determined to have an early-stage cancer can be administered at a lower frequency, duration, and/or dose. For example, a therapeutic intervention can be a targeted therapy (e.g. a kinase inhibitor, and antibody, a bispecific antibody, etc.), which targeted therapy is administered at a lower frequency, duration, and/or dose than if the subject had cancer that was not early-stage (e.g., than if the subject had a late-stage cancer). In some embodiments, a therapeutic intervention is administered to a subject identified as having an early-stage cancer at a frequency that is about 2-fold, 3-fold, 4-fold, 5-fold, 6-fold, 7-fold, 8-fold, 9-fold, 10-fold or more less frequent that if the subject had a cancer that was not early-stage. In some embodiments, a therapeutic intervention is administered to a subject identified as having an early-stage cancer for a duration that is reduced by about 2-fold, 3-fold, 4-fold, 5-fold, 6-fold, 7-fold, 8-fold, 9-fold, 10-fold or more that if the subject had a cancer that was not early-stage. In some embodiments, a therapeutic intervention is administered to a subject identified as having an early-stage cancer at a dosage that is about 2-fold, 3-fold, 4-fold, 5-fold, 6-fold, 7-fold, 8-fold, 9-fold, 10-fold or more less that if the subject had a cancer that was not early-stage. In some embodiments, a therapeutic intervention administered to a subject determined to have an early-stage cancer can be a surgical intervention, and the surgical intervention can be less invasive and/or last for a shorter period of time than if the subject had cancer that was not early-stage (e.g., than if the subject had a late-stage cancer). As one non-limiting example, methods provided herein can be used to determine that a subject has an early-stage cancer, and surgical resection can be used to remove cancer cells or a tumor from the subject. As another non-limiting example, methods provided herein can be used to determine that a subject has an early-stage cancer, and a targeted therapy that is specific for the type of cancer, cancer cell, or cancer cell mutation can be administered to the subject. In some embodiments, a therapeutic intervention administered after the subject has been determined to have an early-stage cancer (e.g. by any of the variety of methods provided herein) results in the cancer being cured. For example, the therapeutic intervention can result in complete elimination of the detected cancer in the subject.

Identifying the Presence of a Cancer Cell in a Subject

Also provided herein are methods for identifying the presence of a cancer cell in a subject. In some embodiments, methods for identifying the presence of a cancer cell in a subject include detecting one or more genetic alterations in a cell-free DNA in a biological sample isolated from the subject, identifying the presence of circulating tumor DNA when at least one of the detected genetic alterations in the cell-free DNA is a cancer cell mutation, and identifying the presence of the cancer cell when the presence of circulating tumor DNA is identified. In some embodiments, the step of detecting is performed when the subject is not known to harbor a cancer cell. In some embodiments, the detected cancer cell can be a cancer cell from any of the exemplary cancers described herein.

In some embodiments, the biological sample is isolated from subject. Any suitable biological sample that contains cell-free DNA can be used in accordance with any of the variety of methods disclosed herein. For example, the biological sample can include blood, plasma, urine, cerebrospinal fluid, saliva, sputum, broncho-alveolar lavage, bile, lymphatic fluid, cyst fluid, stool, ascites, and combinations thereof. Methods of isolating biological samples from a subject are known to those of ordinary skill in the art.

In some embodiments, the step of detecting a genetic alteration (e.g., one or more genetic alterations) in cell-free DNA is performed using one or more of the methods described herein (e.g., a targeted capture method, a next-generation sequencing method, and an array-based method, or any combinations thereof).

In some embodiments, methods provided herein can be used to identify the presence of a cancer cell in a subject by detecting a genetic alteration (e.g., one or more genetic alterations) in circulating tumor DNA present in cell-free DNA, where the cell-free DNA is present in an amount less than about 1500 ng, e.g., less than about 1400 ng, less than about 1300 ng, less than about 1200 ng, less than about 1100 ng, less than about 1000 ng, less than about 900 ng, less than about 800 ng, less than about 700 ng, less than about 600 ng, less than about 500 ng, less than about 400 ng, less than about 300 ng, less than about 200 ng, less than about 150 ng, less than about 100 ng, less than about 95 ng, less than about 90 ng, less than about 85 ng, less than about 80 ng, less than about 75 ng, less than about 70 ng, less than about 65 ng, less than about 60 ng, less than about 55 ng, less than about 50 ng, less than about 45 ng, less than about 40 ng, less than about 35 ng, less than about 30 ng, less than about 25 ng, less than about 20 ng, less than about 15 ng, less than about 10 ng, or less than about 5 ng. In some embodiments, methods provided herein can be used to identify the presence of a cancer cell in a subject by detecting a genetic alteration (e.g., one or more genetic alterations) in circulating tumor DNA present in cell-free DNA, where the circulating tumor DNA represents 100% of the cell-free DNA. In some embodiments, methods provided herein can be used to identify the presence of a cancer cell in a subject by detecting a genetic alteration (e.g., one or more genetic alterations) in circulating tumor DNA present in cell-free DNA, where the circulating tumor DNA represents less than 100% of the cell-free DNA, e.g. about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, about 0.95%, about 0.90%, about 0.85%, about 0.80%, about 0.75%, about 0.70%, about 0.65%, about 0.60%, about 0.55%, about 0.50%, about 0.45%, about 0.40%, about 0.35%, about 0.30%, about 0.25%, about 0.20%, about 0.15%, about 0.10%, about 0.09%, about 0.08%, about 0.07%, about 0.06%, about 0.05% of the cell-free DNA, or less.

In some embodiments, methods provided herein can be used to detect the presence of a cancer cell in a subject at a time period prior to diagnosis of the subject with an early-stage cancer. For example, methods provided herein can be used when a subject has not been diagnosed with cancer and/or when a subject is not known to harbor a cancer cell.

In some embodiments, a cancer cell that is identified in a subject by any of the variety of methods disclosed herein harbors a cancer cell mutation listed in Table S7. In some embodiments, when a cancer cell is identified in a subject by any of the variety of methods disclosed herein, the presence of cancer in the subject is confirmed through further diagnostic testing (e.g., diagnostic scans, biopsies, molecular-based techniques to confirm the presence of the cancer cell mutation, or any of the other diagnostic testing methods disclosed herein or known in the art).

In some embodiments, a cancer cell in a subject that is identified by any of the variety of methods disclosed herein does not include a blood proliferative disorder mutation or germline alteration. For example, a cancer cell that is identified by any of the variety of methods disclosed herein can include a cancer cell mutation that is different from a blood proliferative disorder mutation in a gene listed in Table S5, or different from a blood proliferative disorder mutation listed in Table S5. Additionally or alternatively, a cancer cell that is identified by any of the variety of methods disclosed herein can include a cancer cell mutation that is different from a germline alteration in a gene listed in Table S6, or different from a germline alteration listed in Table S6.

In some embodiments, a therapeutic intervention is administered to the subject after the presence of a cancer cell mutation is identified. Any of the therapeutic interventions disclosed herein or known in the art can be administered.

In some embodiments, methods provided herein can be used to identify the presence of a cancer cell in a subject at a time period prior to diagnosis of the subject with an early-stage cancer (e.g., when the subject is not known to harbor a cancer cell), after which a therapeutic intervention (e.g., any of the therapeutic interventions described herein) can be administered to the subject. In some embodiments, methods provided herein can be used to determine that a subject has an early-stage cancer before other methods (e.g., conventional diagnostic methods) are capable of determining the presence of cancer. In some embodiments, a therapeutic intervention administered to a subject that is determined to have an early-stage cancer using any of the variety of methods provided herein is more effective that if the therapeutic intervention were to be administered to a subject at a later time (e.g., after the cancer has progressed beyond early-stage). In some embodiments, a therapeutic intervention administered to a subject determined to have an early-stage cancer can be administered at a lower frequency, duration, and/or dose. For example, a therapeutic intervention can be a targeted therapy (e.g. a kinase inhibitor, and antibody, a bispecific antibody, etc.), which targeted therapy is administered at a lower frequency, duration, and/or dose than if the subject had cancer that was not early-stage (e.g., than if the subject had a late-stage cancer). In some embodiments, a therapeutic intervention is administered to a subject identified as having an early-stage cancer at a frequency that is about 2-fold, 3-fold, 4-fold, 5-fold, 6-fold, 7-fold, 8-fold, 9-fold, 10-fold or more less frequent that if the subject had a cancer that was not early-stage. In some embodiments, a therapeutic intervention is administered to a subject identified as having an early-stage cancer for a duration that is reduced by about 2-fold, 3-fold, 4-fold, 5-fold, 6-fold, 7-fold, 8-fold, 9-fold, 10-fold or more that if the subject had a cancer that was not early-stage. In some embodiments, a therapeutic intervention is administered to a subject identified as having an early-stage cancer at a dosage that is about 2-fold, 3-fold, 4-fold, 5-fold, 6-fold, 7-fold, 8-fold, 9-fold, 10-fold or more less that if the subject had a cancer that was not early-stage. In some embodiments, a therapeutic intervention administered to a subject determined to have an early-stage cancer can be a surgical intervention, and the surgical intervention can be less invasive and/or last for a shorter period of time than if the subject had cancer that was not early-stage (e.g., than if the subject had a late-stage cancer). As one non-limiting example, methods provided herein can be used to determine that a subject has an early-stage cancer, and surgical resection can be used to remove cancer cells or a tumor from the subject. As another non-limiting example, methods provided herein can be used to determine that a subject has an early-stage cancer, and a targeted therapy that is specific for the type of cancer, cancer cell, or cancer cell mutation can be administered to the subject. In some embodiments, a therapeutic intervention administered after the subject has been determined to have an early-stage cancer (e.g. by any of the variety of methods provided herein) results in the cancer being cured. For example, the therapeutic intervention can result in complete elimination of the detected cancer in the subject.

Determining Efficacy of a Therapeutic Intervention

Also provided herein are methods of determining the efficacy of a therapeutic intervention administered to a subject. In some embodiments, determining the efficacy of a therapeutic intervention (e.g., any of the therapeutic interventions disclosed herein or known in the art) administered to a subject identified as having a cancer cell includes administering the therapeutic intervention to the subject, identifying the presence or absence of circulating tumor DNA by detecting the presence or absence of one or more genetic alterations in cell-free DNA in a biological sample isolated from the subject, wherein at least one of the detected genetic alterations is a cancer cell mutation, and (i) determining that the therapeutic intervention was effective when the absence of circulating tumor DNA is identified, or (ii) determining that the therapeutic intervention was not effective when the presence of circulating tumor DNA is identified.

In some embodiments, determining the efficacy of a therapeutic intervention administered to a subject includes identifying the presence or absence of circulating tumor DNA at a first time point by detecting the presence or absence of one or more genetic alterations in cell-free DNA in a biological sample isolated from the subject, wherein at least one of the detected genetic alterations is a cancer cell mutation, identifying the presence or absence of circulating tumor DNA at a second time point by detecting the presence or absence of one or more genetic alterations in cell-free DNA in a biological sample isolated from the subject, wherein at least one of the detected genetic alterations is the cancer cell mutation, and (i) determining that the therapeutic intervention was effective when the circulating tumor DNA is identified at the first time point, but is not identified at the second time point, or (ii) determining that the therapeutic intervention was not effective when the presence of circulating tumor DNA is identified at both the first and second time points, wherein the subject is administered a therapeutic intervention (e.g., any of the therapeutic interventions disclosed herein or known in the art) between the first and second time points. In some embodiments, the subject is not known to harbor a cancer cell before the first time point.

In some embodiments, determining the efficacy of a therapeutic intervention administered to a subject includes administering the therapeutic intervention (e.g., any of the therapeutic interventions disclosed herein or known in the art) to the subject, identifying the amount of circulating tumor DNA by detecting the presence or absence of one or more genetic alterations in cell-free DNA in a biological sample isolated from the subject, wherein at least one of the detected genetic alterations is a cancer cell mutation, and (i) determining that the therapeutic intervention was effective when the amount of circulating tumor DNA is lower than a reference level of circulating tumor DNA, or (ii) determining that the therapeutic intervention was not effective when the amount of circulating tumor DNA about the same or higher than a reference level of circulating tumor DNA. In some embodiments, the amount of circulating tumor DNA is determined by comparing the amount of cell-free DNA that contains the one or more genetic alterations to the amount of cell-free DNA that does not contain the one or more genetic alterations. In some embodiments, a therapeutic intervention is determined to be effective when the amount of circulating tumor DNA is decreased by about 2-fold, 3-fold, 4-fold, 5-fold, 6-fold, 7-fold, 8-fold, 9-fold, 10-fold or more compared to a reference level of circulating tumor DNA. In some embodiments, a therapeutic intervention is determined to be effective when the amount of circulating tumor DNA is about the same as the amount of a reference level of circulating tumor DNA identified in the subject at a time prior to the first time point when the subject did not harbor a cancer cell. For example, a reference level of circulating tumor DNA in the subject can be the amount of circulating tumor DNA when the subject did not harbor a cancer cell. The amount of circulating tumor DNA when the subject did not harbor a cancer cell can be the level of cell-free DNA that was present in the subject about 1 month, 2 months, 3 months, 4 months, 5 months, 6 months, 1 year, 2 years, 3 years, 4 years, 5 years, 10 years, or more (or any time period between these time periods) before the subject was identified as harboring a cancer cell. In some embodiments, a therapeutic intervention is determined to be effective when the amount of circulating tumor DNA is about the same as the amount of circulating tumor DNA identified in a reference subject that does not harbor, or is not known to harbor, a cancer cell.

In some embodiments, determining the efficacy of a therapeutic intervention administered to a subject includes identifying the amount of circulating tumor DNA at a first time point by detecting the presence or absence of one or more genetic alterations in cell-free DNA in a biological sample isolated from the subject, wherein at least one of the detected genetic alterations is a cancer cell mutation, identifying the amount of circulating tumor DNA at a second time point by detecting the presence or absence of one or more genetic alterations in cell-free DNA in a biological sample isolated from the subject, wherein at least one of the detected genetic alterations is the cancer cell mutation, and (i) determining that the therapeutic intervention was effective when the amount of circulating tumor DNA identified at the second time point is lower than the amount of circulating tumor DNA identified at the first time point, or (ii) determining that the therapeutic intervention was not effective when the amount of circulating tumor DNA identified at the second time point is about the same or higher than the amount of circulating tumor DNA identified at the first time point, wherein the subject is administered a therapeutic intervention (e.g., any of the therapeutic interventions disclosed herein or known in the art) between the first and second time points. In some embodiments, the amount of circulating tumor DNA at the first time point, the second time point, or both is determined by comparing the amount of cell-free DNA that contains the one or more genetic alterations to the amount of cell-free DNA that does not contain the one or more genetic alterations. In some embodiments, the subject is not known to harbor a cancer cell before the first time point. In some embodiments, a therapeutic intervention is determined to be effective when the amount of circulating tumor DNA identified at the second time point is decreased by about 2-fold, 3-fold, 4-fold, 5-fold, 6-fold, 7-fold, 8-fold, 9-fold, 10-fold or more compared to the amount of circulating tumor DNA identified at the first time point. In some embodiments, a therapeutic intervention is determined to be effective when the amount of circulating tumor DNA identified at the second time point is about the same as the amount of a reference level of circulating tumor DNA identified in the subject at a time prior to the first time point when the subject did not harbor a cancer cell. For example, a reference level of circulating tumor DNA in the subject when the subject did not harbor a cancer cell can be the level of circulating tumor DNA that was present in the subject about 1 month, 2 months, 3 months, 4 months, 5 months, 6 months, 1 year, 2 years, 3 years, 4 years, 5 years, 10 years, or more (or any time period between these time periods) before the subject was identified as harboring a cancer cell. In some embodiments, a therapeutic intervention is determined to be effective when the amount of circulating tumor DNA identified at the second time point is about the same as the amount of circulating tumor DNA identified in a reference subject that does not harbor, or is not known to harbor, a cancer cell.

In some embodiments, determining the efficacy of a therapeutic intervention administered to a subject identified as having a cancer cell includes administering the therapeutic intervention (e.g., any of the therapeutic interventions disclosed herein or known in the art) to the subject, identifying the amount of cell-free DNA in a biological sample isolated from the subject, and (i) determining that the therapeutic intervention was effective when the amount of cell-free DNA is lower than a reference level of cell-free DNA, or (ii) determining that the therapeutic intervention was not effective when the amount of cell-free DNA is higher than a reference level of cell-free DNA. In some embodiments, a therapeutic intervention is determined to be effective when the identified amount of cell-free DNA is decreased by about 2-fold, 3-fold, 4-fold, 5-fold, 6-fold, 7-fold, 8-fold, 9-fold, 10-fold or more compared to the amount of a reference level of cell-free DNA. In some embodiments, a therapeutic intervention is determined to be effective when the identified amount of cell-free DNA is about the same as the amount of a reference level of cell-free DNA identified in the subject at a time when the subject did not harbor a cancer cell. For example, a reference level of cell-free DNA in the subject when the subject did not harbor a cancer cell can be the level of cell-free DNA that was present in the subject about 1 month, 2 months, 3 months, 4 months, 5 months, 6 months, 1 year, 2 years, 3 years, 4 years, 5 years, 10 years, or more (or any time period between these time periods) before the subject was identified as harboring a cancer cell. In some embodiments, a therapeutic intervention is determined to be effective when the identified amount of cell-free DNA is about the same as the amount of cell-free DNA identified in a reference subject that does not harbor, or is not known to harbor, a cancer cell.

In some embodiments, determining the efficacy of a therapeutic intervention administered to a subject includes identifying the amount of cell-free DNA at a first time point in a biological sample isolated from the subject, identifying the amount of cell-free DNA at a second time point in a biological sample isolated from the subject, and (i) determining that the therapeutic intervention was effective when the amount of cell-free DNA is lower at the second time point than at the first time point, or (ii) determining that the therapeutic intervention was not effective when the amount of cell-free DNA is about the same or higher at the second time point than at the first time point, wherein the subject is administered a therapeutic intervention (e.g., any of the therapeutic interventions disclosed herein or known in the art) between the first and second time points. In some embodiments, the subject is not known to harbor a cancer cell before the first time point. In some embodiments, a therapeutic intervention is determined to be effective when the amount of cell-free DNA identified at the second time point is decreased by about 2-fold, 3-fold, 4-fold, 5-fold, 6-fold, 7-fold, 8-fold, 9-fold, 10-fold or more compared to the amount of cell-free DNA identified at the first time point. In some embodiments, a therapeutic intervention is determined to be effective when the amount of cell-free DNA identified at the second time point is about the same as the amount of a reference level of cell-free DNA identified in the subject at a time prior to the first time point when the subject did not harbor a cancer cell. For example, a reference level of cell-free DNA in the subject when the subject did not harbor a cancer cell can be the level of cell-free DNA that was present in the subject about 1 month, 2 months, 3 months, 4 months, 5 months, 6 months, 1 year, 2 years, 3 years, 4 years, 5 years, 10 years, or more (or any time period between these time periods) before the subject was identified as harboring a cancer cell. In some embodiments, a therapeutic intervention is determined to be effective when the amount of cell-free DNA identified at the second time point is about the same as the amount of cell-free DNA identified in a reference subject that does not harbor, or is not known to harbor, a cancer cell. In some embodiments, the subject is not known to harbor a cancer cell before the first time point.

In some embodiments of determining the efficacy of a therapeutic intervention, the presence or absence of circulating tumor DNA is identified by any of the variety of methods disclosed herein. For example, presence or absence of circulating tumor DNA can be identified by detecting the presence or absence of one or more genetic alterations in cell-free DNA in a biological sample isolated from the subject, and identifying the presence of circulating tumor DNA when at least one of the detected genetic alterations in the cell-free DNA is a cancer cell mutation and/or identifying the absence of circulating tumor DNA when a genetic alteration is not detected or at least one of the detected genetic alterations in the cell-free DNA is not a cancer cell mutation. In some embodiments, the step of detecting the presence or absence of a genetic alteration (e.g., one or more genetic alterations) in cell-free DNA is performed using one or more of the methods described herein (e.g., a targeted capture method, a next-generation sequencing method, and an array-based method, or any combinations thereof).

In some embodiments, methods provided herein for determining the efficacy of a therapeutic intervention include detecting the presence or absence of a genetic alteration (e.g., one or more genetic alterations) in circulating tumor DNA present in cell-free DNA, where the cell-free DNA is present in an amount less than about 1500 ng, e.g., less than about 1400 ng, less than about 1300 ng, less than about 1200 ng, less than about 1100 ng, less than about 1000 ng, less than about 900 ng, less than about 800 ng, less than about 700 ng, less than about 600 ng, less than about 500 ng, less than about 400 ng, less than about 300 ng, less than about 200 ng, less than about 150 ng, less than about 100 ng, less than about 95 ng, less than about 90 ng, less than about 85 ng, less than about 80 ng, less than about 75 ng, less than about 70 ng, less than about 65 ng, less than about 60 ng, less than about 55 ng, less than about 50 ng, less than about 45 ng, less than about 40 ng, less than about 35 ng, less than about 30 ng, less than about 25 ng, less than about 20 ng, less than about 15 ng, less than about 10 ng, or less than about 5 ng. In some embodiments, methods provided herein for determining the efficacy of a therapeutic intervention include detecting the presence or absence of a genetic alteration (e.g., one or more genetic alterations) in circulating tumor DNA present in cell-free DNA, where the circulating tumor DNA represents 100% of the cell-free DNA. In some embodiments, methods provided herein for determining the efficacy of a therapeutic intervention include detecting the presence or absence of a genetic alteration (e.g., one or more genetic alterations) in circulating tumor DNA present in cell-free DNA, where the circulating tumor DNA represents less than 100% of the cell-free DNA, e.g. about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, about 0.95%, about 0.90%, about 0.85%, about 0.80%, about 0.75%, about 0.70%, about 0.65%, about 0.60%, about 0.55%, about 0.50%, about 0.45%, about 0.40%, about 0.35%, about 0.30%, about 0.25%, about 0.20%, about 0.15%, about 0.10%, about 0.09%, about 0.08%, about 0.07%, about 0.06%, about 0.05% of the cell-free DNA, or less.

In some embodiments of determining the efficacy of a therapeutic intervention, a cancer cell mutation that is detected by any of the variety of methods disclosed herein is present in a cancer cell present in the subject. For example, a cancer cell mutation listed in Table S7 that is detected using any of the variety of methods disclosed herein can be present in a cancer cell present in the subject. In some embodiments, a cancer cell mutation detected by any of the variety of methods disclosed herein is confirmed to be present in a cancer cell present in the subject through further diagnostic testing (e.g., diagnostic scans, biopsies, molecular-based techniques to confirm the presence of the cancer cell mutation, or any of the other diagnostic testing methods disclosed herein or known in the art).

In some embodiments of determining the efficacy of a therapeutic intervention, a cancer cell mutation that is detected by any of the variety of methods disclosed herein can be different from a blood proliferative disorder mutation or germline alteration (e.g., the cancer cell mutation is not a blood proliferative disorder mutation or germline alteration). For example, a cancer cell mutation that is detected by any of the variety of methods disclosed herein can be different from a blood proliferative disorder mutation in a gene listed in Table S5, or different from a blood proliferative disorder mutation listed in Table S5. Additionally or alternatively, a cancer cell mutation that is detected by any of the variety of methods disclosed herein can be different from a germline alteration in a gene listed in Table S6, or different from a germline alteration listed in Table S6.

In some embodiments, after determining the efficacy of a therapeutic intervention administered to a subject, the subject can be administered a diagnostic test (e.g., any of the diagnostic tests disclosed herein) and/or monitored (e.g., according to any of the monitoring methods, schedules, etc. disclosed herein). In some embodiments, after determining the efficacy of a therapeutic intervention administered to a subject, the subject can be selected for further diagnostic testing (e.g., using any of the diagnostic tests disclosed herein) and/or selected for increased monitored (e.g., according to any of the increased monitoring methods, schedules, etc. disclosed herein). For example, a subject can be administered a therapeutic intervention, which therapeutic intervention is determined to be effective, and the subject can then be administered a diagnostic test and/or selected for further diagnostic testing (e.g., to confirm the effectiveness of the therapeutic intervention). As another example, a subject can be administered a therapeutic intervention, which therapeutic intervention is determined to be effective, and the subject can then be monitored and/or selected for increased monitoring (e.g., to keep watch for the reemergence of another cancer).

In some embodiments of determining the efficacy of a therapeutic intervention, methods provided herein can be used to identify the presence of circulating tumor DNA and/or a cancer cell in a subject at a time period prior to diagnosis of the subject with an early-stage cancer (e.g., when the subject is not known to harbor a cancer cell), after which a therapeutic intervention (e.g., any of the therapeutic interventions described herein) can be administered to the subject. In some embodiments of determining the efficacy of a therapeutic intervention, methods provided herein can be used to determine that a subject has an early-stage cancer before other methods (e.g., conventional diagnostic methods) are capable of determining the presence of cancer. In some embodiments of determining the efficacy of a therapeutic intervention, a therapeutic intervention administered to a subject that is determined to have an early-stage cancer using any of the variety of methods provided herein is determined to be more effective that if the therapeutic intervention were to be administered to a subject at a later time (e.g., after the cancer has progressed beyond early-stage). In some embodiments of determining the efficacy of a therapeutic intervention, a therapeutic intervention administered to a subject determined to have an early-stage cancer can be administered at a lower frequency, duration, and/or dose, and the therapeutic intervention can be determined to be more effective than if the therapeutic intervention were to be administered to a subject at a later time (e.g., after the cancer has progressed beyond early-stage). For example, a therapeutic intervention can be a targeted therapy (e.g. a kinase inhibitor, and antibody, a bispecific antibody, etc.), which targeted therapy is determined to be effective when administered at a lower frequency, duration, and/or dose than if the subject had cancer that was not early-stage (e.g., than if the subject had a late-stage cancer). In some embodiments, a therapeutic intervention is determined to be effective when administered to a subject identified as having an early-stage cancer when the therapeutic intervention is administered at a frequency that is about 2-fold, 3-fold, 4-fold, 5-fold, 6-fold, 7-fold, 8-fold, 9-fold, 10-fold or more less frequent that if the subject had a cancer that was not early-stage. In some embodiments, a therapeutic intervention is determined to be effective when administered to a subject identified as having an early-stage cancer when the therapeutic intervention is administered for a duration that is reduced by about 2-fold, 3-fold, 4-fold, 5-fold, 6-fold, 7-fold, 8-fold, 9-fold, 10-fold or more that if the subject had a cancer that was not early-stage. In some embodiments, a therapeutic intervention is determined to be effective when administered to a subject identified as having an early-stage cancer at a dosage that is about 2-fold, 3-fold, 4-fold, 5-fold, 6-fold, 7-fold, 8-fold, 9-fold, 10-fold or more less that if the subject had a cancer that was not early-stage. In some embodiments, a therapeutic intervention is determined to be effective when it is a surgical intervention that is administered to a subject determined to have an early-stage cancer, wherein the surgical intervention is less invasive and/or lasts for a shorter period of time than if the subject had cancer that was not early-stage (e.g., than if the subject had a late-stage cancer). As one non-limiting example, methods provided herein can be used to determine that a therapeutic intervention is effective when a subject has an early-stage cancer, and surgical resection can be used to remove cancer cells or a tumor from the subject, which surgical resection is determined to be more effective. As another non-limiting example, methods provided herein can be used to determine that a therapeutic intervention is effective when a subject has an early-stage cancer, and a targeted therapy that is specific for the type of cancer, cancer cell, or cancer cell mutation can be administered to the subject. In some embodiments, a therapeutic intervention administered is determined to be effective when the subject has been determined to have an early-stage cancer (e.g. by any of the variety of methods provided herein), and the therapeutic intervention results in the cancer being cured. For example, the therapeutic intervention can be determined to be effective when it results in complete elimination of the detected cancer in the subject.

Determining, Monitoring, and Treating Resistance to a Therapeutic Intervention

Also provided herein are methods for determining that a subject that has developed resistance to a therapeutic intervention (e.g., any of the therapeutic interventions disclosed herein or known in the art), methods for monitoring a subject for the development of resistance to a therapeutic intervention, and methods for treating such subjects with a different therapeutic intervention. For example, a subject that harbors a cancer cell having a first cancer cell mutation can be administered a first therapeutic intervention (e.g., of a kinase inhibitor that specifically targets cancer cells having that cancer cell mutation). During the first therapeutic intervention, the cancer cell can acquire a second cancer cell mutation (e.g., a "resistance mutation"), which second cancer cell mutation renders the cancer cell resistant to the first therapeutic intervention. In some cases, a second therapeutic intervention that is effective against a cancer cell that harbors the second cancer cell mutation is selected and/or administered to the subject. In some embodiments, a second cancer cell mutation can be any of the "resistance mutations" identified in Dogogo-Jack et al., Overcoming On-Target Resistance to Tyrosine Kinase Inhibitors in Lung Cancer, Annu. Rev. Cancer Biol., 1:257-74, 2017, incorporated herein by reference in its entirety.

In some embodiments, methods of determining that a subject that has developed resistance to a therapeutic intervention (e.g., any of the therapeutic interventions disclosed herein or known in the art) include using any of the methods disclosed herein for detecting circulating tumor DNA, a cancer cell mutation, and/or the presence of a cancer cell. In some embodiments, a subject is determined to have developed resistance to a therapeutic intervention when that therapeutic intervention is no longer effective or is less effective than it was when first administered. For example, a subject can be determined to have developed resistance to a therapeutic intervention when the therapeutic intervention is at least 20%, 25%, 30%, 35%, 40% 45%, 50%, 55%, 60%, 65%, 70%, 75%, 80%, 85%, 90%, 95%, or 100%, or any percentage within between, less effective than when the therapeutic intervention was first administered. The effectiveness of a therapeutic intervention, both when it is first administered and during the course of the therapeutic intervention, can be determined by any of a variety of methods and techniques. For example, the size and/or position of the tumor (as determined, e.g., by scanning or imaging technologies), the number of cancer cells, the amount of cell-free DNA, and/or the amount of circulating tumor DNA can be determined and used to assess whether a subject has developed resistance to the therapeutic intervention. Other suitable methods and techniques are known in the art. In some embodiments, after determining that a subject that has developed resistance to a therapeutic intervention, a different therapeutic intervention (e.g., any of the therapeutic interventions disclosed herein or known in the art) is selected and/or administered to the subject.

In some embodiments, methods for monitoring a subject for the development of resistance to a therapeutic intervention (e.g., any of the therapeutic interventions disclosed herein or known in the art) include using any of the methods disclosed herein for detecting circulating tumor DNA, a cancer cell mutation, and/or the presence of a cancer cell. In some embodiments, a subject is monitored for the presence of circulating tumor DNA, a cancer cell mutation, and/or a cancer cell when the subject was previously determined to have different circulating tumor DNA, a different cancer cell mutation, and/or a different cancer cell. For example, the presence of a first type of circulating tumor DNA, a first cancer cell mutation, and/or a first cancer cell can be identified in a subject (e.g., by any of the methods disclosed herein), and the subject can be monitored for the appearance of a second type of circulating tumor DNA, a second cancer cell mutation, and/or a second cancer cell a later time point. In some embodiments, the subject is selected for and/or administered a therapeutic intervention after the first type of circulating tumor DNA, a first cancer cell mutation, and/or a first cancer cell is identified. In some embodiments, the second type of circulating tumor DNA, the second cancer cell mutation, and/or the second cancer cell is identified after the subject being monitored is selected for and/or administered a therapeutic intervention (e.g., any of the therapeutic interventions disclosed herein or known in the art).

In some embodiments, methods for treating a subject that has developed resistance to a therapeutic intervention (e.g., any of the therapeutic interventions disclosed herein or known in the art) include using any of the methods disclosed herein for detecting circulating tumor DNA, a cancer cell mutation, and/or the presence of a cancer cell. In some embodiments, methods for treating a subject that has developed resistance to a therapeutic intervention include detecting a first alteration in a cell-free DNA in a first biological sample isolated from the subject, wherein the step of detecting is performed when the subject is not known to harbor a cancer cell, identifying the presence of circulating tumor DNA in the cell-free DNA of the first biological sample when the first alteration in the cell-free DNA of the first biological sample is a first cancer cell mutation, identifying the presence of a first cancer cell when the presence of circulating tumor DNA is identified in the cell-free DNA of the first biological sample, administering a first therapeutic intervention to the subject when the presence of the first cancer cell is identified, further detecting a second alteration in cell-free DNA from a second biological sample isolated from the subject, identifying the presence of circulating tumor DNA in the cell-free DNA of the second biological sample when the second alteration in the cell-free DNA of the second biological sample is a cancer cell mutation, identifying the presence of a second cancer cell when the presence of circulating tumor DNA is identified in the cell-free DNA of the second biological sample, and administering a second therapeutic intervention (e.g., any of the therapeutic interventions disclosed herein or known in the art) to the subject when the presence of the second cancer cell is identified. In some embodiments, the second cancer cell mutation is different from the first cancer cell mutation. In some embodiments, the second therapeutic intervention is different from the first therapeutic intervention. For example, the first therapeutic intervention can be a surgery (e.g., surgical resection) and the second therapeutic intervention can be a targeted therapy, chemotherapy, or radiation. In some embodiments, both the first and second therapeutic interventions are targeted therapies (e.g., kinase inhibitors), which first and second targeted therapies are effective against different cancer cell mutations. For example, a first therapeutic intervention can be effective against a cancer cell mutation (or a cancer cell that harbors one of a variety of different cancer cell mutations), but is not effective against a different cancer cell mutation; the second targeted therapy can be effective against such a different cancer cell mutation.

In some embodiments of determining that a subject that has developed resistance to a therapeutic intervention, monitoring a subject for the development of resistance to a therapeutic intervention, and/or treating such subjects with a different therapeutic intervention, the presence of circulating tumor DNA, a cancer cell mutation (e.g., any of the variety of cancer cell mutations disclosed herein), and/or the presence of a cancer cell (e.g., a cancer cell from any of the variety of cancers disclosed herein) is determined. For example, the presence of circulating tumor DNA in a subject can be detected by detecting one or more genetic alterations in cell-free DNA in a biological sample isolated from the subject, and identifying the presence of circulating tumor DNA when at least one of the detected genetic alterations in the cell-free DNA is a cancer cell mutation. As another example, the presence of a cancer cell in a subject can be detected by detecting one or more genetic alterations in cell-free DNA in a biological sample isolated from the subject, identifying the presence of circulating tumor DNA when at least one of the detected genetic alterations in the cell-free DNA is a cancer cell mutation, and identifying the presence of the cancer cell when the presence of circulating tumor DNA is identified.

In some embodiments of determining that a subject that has developed resistance to a therapeutic intervention, monitoring a subject for the development of resistance to a therapeutic intervention, and/or treating such subjects with a different therapeutic intervention, the biological sample (e.g., a first biological sample, a second biological sample, or both) is isolated from subject. Any suitable biological sample that contains cell-free DNA can be used in accordance with any of the variety of methods disclosed herein. For example, the biological sample can include blood, plasma, urine, cerebrospinal fluid, saliva, sputum, bronchoalveolar lavage, bile, lymphatic fluid, cyst fluid, stool, ascites, and combinations thereof. Methods of isolating biological samples from a subject are known to those of ordinary skill in the art.

In some embodiments, methods provided herein for determining that a subject that has developed resistance to a therapeutic intervention, for monitoring a subject for the development of resistance to a therapeutic intervention, and/or for treating such subjects with a different therapeutic intervention include detecting a genetic alteration (e.g., one or more genetic alterations) in circulating tumor DNA present in cell-free DNA, where the cell-free DNA is present in an amount less than about 1500 ng, e.g., less than about 1400 ng, less than about 1300 ng, less than about 1200 ng, less than about 1100 ng, less than about 1000 ng, less than about 900 ng, less than about 800 ng, less than about 700 ng, less than about 600 ng, less than about 500 ng, less than about 400 ng, less than about 300 ng, less than about 200 ng, less than about 150 ng, less than about 100 ng, less than about 95 ng, less than about 90 ng, less than about 85 ng, less than about 80 ng, less than about 75 ng, less than about 70 ng, less than about 65 ng, less than about 60 ng, less than about 55 ng, less than about 50 ng, less than about 45 ng, less than about 40 ng, less than about 35 ng, less than about 30 ng, less than about 25 ng, less than about 20 ng, less than about 15 ng, less than about 10 ng, or less than about 5 ng. In some embodiments methods provided herein for determining that a subject that has developed resistance to a therapeutic intervention, for monitoring a subject for the development of resistance to a therapeutic intervention, and/or for treating such subjects with a different therapeutic intervention include detecting a genetic alteration (e.g., one or more genetic alterations) in circulating tumor DNA present in cell-free DNA, where the circulating tumor DNA represents 100% of the cell-free DNA. In some embodiments methods provided herein for determining that a subject that has developed resistance to a therapeutic intervention, for monitoring a subject for the development of resistance to a therapeutic intervention, and/or for treating such subjects with a different therapeutic intervention include detecting a genetic alteration (e.g., one or more genetic alterations) in circulating tumor DNA present in cell-free DNA, where the circulating tumor DNA represents less than 100% of the cell-free DNA, e.g. about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, about 0.95%, about 0.90%, about 0.85%, about 0.80%, about 0.75%, about 0.70%, about 0.65%, about 0.60%, about 0.55%, about 0.50%, about 0.45%, about 0.40%, about 0.35%, about 0.30%, about 0.25%, about 0.20%, about 0.15%, about 0.10%, about 0.09%, about 0.08%, about 0.07%, about 0.06%, about 0.05% of the cell-free DNA, or less.

In some embodiments of determining that a subject that has developed resistance to a therapeutic intervention, a cancer cell mutation that is detected by any of the variety of methods disclosed herein is present in a cancer cell present in the subject. For example, a cancer cell mutation listed in Table S7 that is detected using any of the variety of methods disclosed herein can be present in a cancer cell present in the subject. In some embodiments, a cancer cell mutation detected by any of the variety of methods disclosed herein is confirmed to be present in a cancer cell present in the subject through further diagnostic testing (e.g., diagnostic scans, biopsies, molecular-based techniques to confirm the presence of the cancer cell mutation, or any of the other diagnostic testing methods disclosed herein or known in the art).

In some embodiments of determining that a subject that has developed resistance to a therapeutic intervention, a cancer cell mutation that is detected by any of the variety of methods disclosed herein can be different from a blood proliferative disorder mutation or germline alteration (e.g., the cancer cell mutation is not a blood proliferative disorder mutation or germline alteration). For example, a cancer cell mutation that is detected by any of the variety of methods disclosed herein can be different from a blood proliferative disorder mutation in a gene listed in Table S5, or different from a blood proliferative disorder mutation listed in Table S5. Additionally or alternatively, a cancer cell mutation that is detected by any of the variety of methods disclosed herein can be different from a germline alteration in a gene listed in Table S6, or different from a germline alteration listed in Table S6.

In some embodiments, after a subject that has developed resistance to a therapeutic intervention and after a second therapeutic intervention is administered, the first therapeutic intervention is stopped. In some embodiments, after a subject that has developed resistance to a therapeutic intervention and after a second therapeutic intervention is administered, the first therapeutic intervention and second therapeutic intervention are administered together (e.g., simultaneously or sequentially). In some embodiments, a subject that has developed resistance to a therapeutic intervention exhibits at least a 20%, 25%, 30%, 35%, 40% 45%, 50%, 55%, 60%, 65%, 70%, 75%, 80%, 85%, 90%, 95%, or 100%, or any percentage between, decrease in the effectiveness of the first therapeutic intervention, such that the cancer is treated less effectively (e.g., as determined by detecting or measuring the size and/or position of the tumor (as determined, e.g., by scanning or imaging technologies), the number of cancer cells, the amount of cell-free DNA, and/or the amount of circulating tumor). In some embodiments, a subject can develop resistance to a first therapeutic intervention such that the cancer is treated less effectively with just the first therapeutic intervention, but the subject can be treated more effectively when a second therapeutic intervention (e.g., a therapeutic intervention selected after the subject has developed resistance) is administered. In some embodiments, administration of the second therapeutic intervention results in a treatment that is at least 50%, 55%, 60%, 65%, 70%, 75%, 80%, 85%, 90%, 95%, 100% or more effective than the effectiveness of administration of the first therapeutic intervention (e.g., as determined by detecting or measuring the size and/or position of the tumor (as determined, e.g., by scanning or imaging technologies), the number of cancer cells, the amount of cell-free DNA, and/or the amount of circulating tumor).

Selecting a Subject for Further Diagnostic Testing

Also provided herein are methods for selecting a subject for further diagnostic testing. In some embodiments, methods for selecting a subject for further diagnostic testing include detecting one or more genetic alterations in cell-free DNA in a biological sample isolated from the subject, identifying the presence of circulating tumor DNA when at least one of the detected genetic alterations in the cell-free DNA is a cancer cell mutation, and selecting a subject for further diagnostic testing when the presence of circulating tumor DNA is identified. In some embodiments, the step of detecting is performed when the subject is not known to harbor a cancer cell.

In some embodiments, the biological sample is isolated from subject. Any suitable biological sample that contains cell-free DNA can be used in accordance with any of the variety of methods disclosed herein. For example, the biological sample can include blood, plasma, urine, cerebrospinal fluid, saliva, sputum, broncho-alveolar lavage, bile, lymphatic fluid, cyst fluid, stool, ascites, and combinations thereof. Methods of isolating biological samples from a subject are known to those of ordinary skill in the art.

In some embodiments, the step of detecting a genetic alteration (e.g., one or more genetic alterations) in cell-free DNA is performed using one or more of the methods described herein (e.g., a targeted capture method, a next-generation sequencing method, and an array-based method, or any combinations thereof).

In some embodiments, methods provided herein for selecting a subject for further diagnostic testing include detecting a genetic alteration (e.g., one or more genetic alterations) in circulating tumor DNA present in cell-free DNA, where the cell-free DNA is present in an amount less than about 1500 ng, e.g., less than about 1400 ng, less than about 1300 ng, less than about 1200 ng, less than about 1100 ng, less than about 1000 ng, less than about 900 ng, less than about 800 ng, less than about 700 ng, less than about 600 ng, less than about 500 ng, less than about 400 ng, less than about 300 ng, less than about 200 ng, less than about 150 ng, less than about 100 ng, less than about 95 ng, less than about 90 ng, less than about 85 ng, less than about 80 ng, less than about 75 ng, less than about 70 ng, less than about 65 ng, less than about 60 ng, less than about 55 ng, less than about 50 ng, less than about 45 ng, less than about 40 ng, less than about 35 ng, less than about 30 ng, less than about 25 ng, less than about 20 ng, less than about 15 ng, less than about 10 ng, or less than about 5 ng. In some embodiments, methods provided herein for selecting a subject for further diagnostic testing include detecting a genetic alteration (e.g., one or more genetic alterations) in circulating tumor DNA present in cell-free DNA, where the circulating tumor DNA represents 100% of the cell-free DNA. In some embodiments, methods provided herein for selecting a subject for further diagnostic testing include detecting a genetic alteration (e.g., one or more genetic alterations) in circulating tumor DNA present in cell-free DNA, where the circulating tumor DNA represents less than 100% of the cell-free DNA, e.g. about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, about 0.95%, about 0.90%, about 0.85%, about 0.80%, about 0.75%, about 0.70%, about 0.65%, about 0.60%, about 0.55%, about 0.50%, about 0.45%, about 0.40%, about 0.35%, about 0.30%, about 0.25%, about 0.20%, about 0.15%, about 0.10%, about 0.09%, about 0.08%, about 0.07%, about 0.06%, about 0.05% of the cell-free DNA, or less.

In some embodiments, methods provided herein can be used to select a subject for further diagnostic testing at a time period prior to diagnosis of the subject with an early-stage cancer. For example, methods provided herein for selecting a subject for further diagnostic testing can be used when a subject has not been diagnosed with cancer and/or when a subject is not known to harbor a cancer cell.

In some embodiments, a cancer cell mutation that is detected in a subject that is selected for further diagnostic testing by any of the variety of methods disclosed herein is present in a cancer cell present in the subject. For example, a cancer cell mutation listed in Table S7 that is detected in a subject that is selected for further diagnostic testing using any of the variety of methods disclosed herein can be present in a cancer cell present in the subject.

In some embodiments, a cancer cell mutation that is detected in a subject that is selected for further diagnostic testing by any of the variety of methods disclosed herein can be different from a blood proliferative disorder mutation or germline alteration (e.g., the cancer cell mutation is not a blood proliferative disorder mutation or germline alteration).

For example, a cancer cell mutation that is detected in a subject that is selected for further diagnostic testing by any of the variety of methods disclosed herein can be different from a blood proliferative disorder mutation in a gene listed in Table S5, or different from a blood proliferative disorder mutation listed in Table S5. Additionally or alternatively, a cancer cell mutation that is detected in a subject that is selected for further diagnostic testing by any of the variety of methods disclosed herein can be different from a germline alteration in a gene listed in Table S6, or different from a germline alteration listed in Table S6.

In some embodiments, the diagnostic testing method is a scan. In some embodiments, the scan is a computed tomography (CT), a CT angiography (CTA), a esophagram (a Barium swallom), a Barium enema, a magnetic resonance imaging (MRI), a PET scan, an ultrasound (e.g., an endobronchial ultrasound, an endoscopic ultrasound), an X-ray, a DEXA scan.

In some embodiments, the diagnostic testing method is a physical examination, such as an anoscopy, a bronchoscopy (e.g., an autofluorescence bronchoscopy, a white-light bronchoscopy, a navigational bronchoscopy), a colonoscopy, a digital breast tomosynthesis, an endoscopic retrograde cholangiopancreatography (ERCP), an ensophagogastroduodenoscopy, a mammography, a Pap smear, a pelvic exam, a positron emission tomography and computed tomography (PET-CT) scan.

In some embodiments, the diagnostic testing method is a biopsy (e.g., a bone marrow aspiration, a tissue biopsy). In some embodiments, the biopsy is performed by fine needle aspiration or by surgical excision. In some embodiments, the diagnostic testing methods further includes obtaining a biological sample (e.g., a tissue sample, a urine sample, a blood sample, a check swab, a saliva sample, a mucosal sample (e.g., sputum, bronchial secretion), a nipple aspirate, a secretion or an excretion). In some embodiments, the diagnostic testing methods includes determining exosomal proteins (e.g., an exosomal surface protein (e.g., CD24, CD147, PCA-3)) (Soung et al. (2017) Cancers 9(1):pii:E8). In some embodiments, the diagnostic testing method is an oncotype DX® test (Baehner (2016) Ecancermedicalscience 10:675).

In some embodiments, the diagnostic testing method includes determining the level of a known biomarker (e.g., CA-125, prostate specific antigen (PSA)). For example, a high amount of CA-125 is found in subject's blood who has ovarian cancer, endometrial cancer, fallopian tube cancer, pancreatic cancer, stomach cancer, esophageal cancer, colon cancer, liver cancer, breast cancer, or lung cancer. The term "biomarker" as used herein refers to "a biological molecule found in blood, other bodily fluids, or tissues that is a sign of a normal or abnormal process, or of a condition or disease", e.g., as defined by the National Cancer Institute. (www.cancer.gov/publications/dictionaries/cancer-terms?CdrID=45618). A biomarker can include a nucleic acid (e.g., a DNA molecule, a RNA molecule (e.g., a microRNA, a long non-coding RNA (lncRNA) or other non-coding RNA), a peptide, a protein or fragment thereof).

In some embodiments, the biomarker is FLT3, NPM1, CEBPA, PRAM1, ALK, BRAF, KRAS, EGFR, Kit, NRAS, JAK2, KRAS, HPV virus, ERBB2, BCR-ABL, BRCA1, BRCA2, CEA, AFP, and/or LDH. See e.g., Easton et al. (1995) Am. J. Hum. Genet. 56: 265-271, Hall et al. (1990) Science 250: 1684-1689, Lin et al. (2008) Ann. Intern. Med. 149: 192-199, Allegra et al. (2009) (2009) J. Clin. Oncol. 27: 2091-2096, Paik et al. (2004) N. Engl. J. Med. 351: 2817-2826, Bang et al. (2010) Lancet 376: 687-697, Piccart-Gebhart et al. (2005) N. Engl. J. Med. 353: 1659-1672, Romond et al. (2005) N. Engl. J. Med. 353: 1673-1684, Locker et al. (2006) J. Clin. Oncol. 24: 5313-5327, Giligan et al. (2010) J. Clin. Oncol. 28: 3388-3404, Harris et al. (2007) J. Clin. Oncol. 25: 5287-5312; Henry and Hayes (2012) Mol. Oncol. 6: 140-146. In some embodiments, the biomarker is a biomarker for detection of breast cancer in a subject, such as MUC-1, CEA, p53, urokinase plasminogen activator, BRCA1, BRCA2, and/or HER2 (Gam (2012) World J. Exp. Med. 2(5): 86-91). In some embodiments, the biomarker is a biomarker for detection of lung cancer in a subject, such as KRAS, EGFR, ALK, MET, and/or ROS1 (Mao (2002) Oncogene 21: 6960-6969; Korpanty et al. (2014) Front Oncol. 4: 204). In some embodiments, the biomarker is a biomarker for detection of ovarian cancer in a subject, such as HPV, CA-125, HE4, CEA, VCAM-1, KLK6/7, GST1, PRSS8, FOLR1, ALDH1 (Nolen and Lokshin (2012) Future Oncol. 8(1): 55-71; Sarojini et al. (2012) J. Oncol. 2012:709049). In some embodiments, the biomarker is a biomarker for detection of colorectal cancer in a subject, such as MLH1, MSH2, MSH6, PMS2, KRAS, and BRAF (Gonzalez-Pons and Cruz-Correa (2015) Biomed. Res. Int. 2015: 149014; Alvarez-Chaver et al. (2014) World J. Gastroenterol. 20(14): 3804-3824). In some embodiments, the diagnostic testing method determines the presence and/or expression level of a nucleic acid (e.g., microRNA (Sethi et al. (2011) J. Carcinog. Mutag. S1-005), RNA, a SNP (Hosein et al. (2013) Lab. Invest doi: 10.1038/labinvest.2013.54; Falzoi et al. (2010) Pharmacogenomics 11: 559-571), methylation status (Castelo-Branco et al. (2013) Lancet Oncol 14: 534-542), a hotspot cancer mutation (Yousem et al. (2013) Chest 143: 1679-1684)). Non-limiting examples of methods of detecting a nucleic acid in a sample include: PCR, RT-PCR, sequencing (e.g., next generation sequencing methods, deep sequencing), a DNA microarray, a microRNA microarray, a SNP microarray, fluorescent in situ hybridization (FISH), restriction fragment length polymorphism (RFLP), gel electrophoresis, Northern blot analysis, Southern blot analysis, chromogenic in situ hybridizatuib (CISH), chromatin immunoprecipitation (ChIP), SNP genotyping, and DNA methylation assay. See, e.g., Meldrum et al. (2011) Clin. Biochem. Rev. 32(4): 177-195; Sidranksy (1997) Science 278(5340): 1054-9.

In some embodiments, the diagnostic testing method includes determining the presence of a protein biomarker in a sample (e.g., a plasma biomarker (Mirus et al. (2015) Clin. Cancer Res. 21(7): 1764-1771)). Non-limiting examples of methods of determining the presence of a protein biomarker include: western blot analysis, immunohistochemistry (IHC), immunofluorescence, mass spectrometry (MS) (e.g., matrix assisted laser desorption/ionization (MALDI)-MS, surface enhanced laser desorption/ionization time-of-flight (SELDI-TOF)-MS), enzyme-linked immunosorbent assay (ELISA), flow cytometry, proximity assay (e.g., VeraTag proximity assay (Shi et al. (2009) Diagnostic molecular pathology: the American journal of surgical pathology, part B: 18: 11-21, Huang et al. (2010) AM. J. Clin. Pathol. 134: 303-11)), a protein microarray (e.g., an antibody microarray (Ingvarsson et al. (2008) Proteomics 8: 2211-9, Woodbury et al. (2002) J. Proteome Res. 1: 233-237), an IHC-based microarray (Stromberg et al. (2007) Proteomics 7: 2142-50), a microarray ELISA (Schroder et al. (2010) Mol. Cell. Proteomics 9: 1271-80). In some embodiments, the method of determining the presence of a protein biomarker is a functional assay. In some embodiments, the functional assay is a kinase assay (Ghosh et al. (2010) Biosensors & Bioelectronics 26: 424-31, Mizutani et al. (2010) Clin. Cancer Res. 16: 3964-75, Lee et al. (2012) Biomed. Microdevices 14: 247-57), a protease assay (Lowe et al. (2012) ACS nano. 6: 851-7, Fujiwara et al. (2006) Breast cancer 13: 272-8, Darragh et al. (2010) Cancer Res 70: 1505-12). See, e.g., Powers and Palecek (2015) J. Heathc Eng. 3(4): 503-534, for a review of protein analytical assays for diagnosing cancer patients.

In some embodiments, the diagnostic testing method includes determining the presence of a circulating tumor cell. In some embodiments, the diagnostic testing method includes determining the complete blood cell count (i.e. the percentage and types of immune cells). In some embodiments, the diagnostic testing method is a fecal occult blood test.

In some embodiments, a subject that has been selected for further diagnostic testing can also be selected for increased monitoring. As will be recognized by those of skill in the art, once the presence of a cancer cell has been identified (e.g., by any of the variety of methods disclosed herein), it may be beneficial for the subject to undergo both further diagnostic testing (e.g., to determine the size and/or exact location of the tumor harboring the cancer cell) and increased monitoring (e.g., to assess the progression of the tumor or cancer in the subject and/or to assess the development of additional cancer cell mutations). For example, a subject selected for further diagnostic testing can also be selected for increased monitoring, in which the subject is administered a diagnostic test at a frequency of twice daily, daily, bi-weekly, weekly, bi-monthly, monthly, quarterly, semi-annually, annually, or any at frequency therein. In some embodiments, a subject selected for further diagnostic testing can also be selected for increased monitoring, in which the subject is administered one or more additional diagnostic tests compared to a subject that has not been selected for further diagnostic testing and increased monitoring.

In some embodiments, a therapeutic intervention is administered to the subject that is selected for further diagnostic testing after a cancer cell mutation is detected. Any of the therapeutic interventions disclosed herein or known in the art can be administered. For example, a subject that has been selected for further diagnostic testing can be further tested, and a therapeutic intervention can be administered if the presence of the cancer cell is confirmed. Additionally or alternatively, a subject that has been selected for further diagnostic testing can be administered a therapeutic intervention, and tested further as the therapeutic intervention progresses. In some embodiments, after a subject that has been selected for further diagnostic testing has been administered a therapeutic intervention, the further diagnostic testing will reveal one or more additional cancer cell mutations. In some embodiments, such one or more additional cancer cell mutations will provide cause to administer a different therapeutic intervention (e.g., a resistance mutation may arise during the therapeutic intervention, which resistance mutant is resistance to the original therapeutic intervention).

Selecting a Subject for Increased Monitoring

Also provided herein are methods for selecting a subject for increased monitoring. In some embodiments, methods for selecting a subject for increased monitoring include detecting one or more genetic alterations in cell-free DNA in a biological sample isolated from the subject, identifying the presence of circulating tumor DNA when at least one of the detected genetic alterations in the cell-free DNA is a cancer cell mutation, and selecting a subject for increased monitoring when the presence of circulating tumor DNA is identified. In some embodiments, the step of detecting is performed when the subject is not known to harbor a cancer cell.

In some embodiments, the biological sample is isolated from subject. Any suitable biological sample that contains cell-free DNA can be used in accordance with any of the variety of methods disclosed herein. For example, the biological sample can include blood, plasma, urine, cerebrospinal fluid, saliva, sputum, broncho-alveolar lavage, bile, lymphatic fluid, cyst fluid, stool, ascites, and combinations thereof. Methods of isolating biological samples from a subject are known to those of ordinary skill in the art.

In some embodiments, the step of detecting a genetic alteration (e.g., one or more genetic alterations) in cell-free DNA is performed using one or more of the methods described herein (e.g., a targeted capture method, a next-generation sequencing method, and an array-based method, or any combinations thereof).

In some embodiments, methods provided herein for selecting a subject for increased monitoring include detecting a genetic alteration (e.g., one or more genetic alterations) in circulating tumor DNA present in cell-free DNA, where the cell-free DNA is present in an amount less than about 1500 ng, e.g., less than about 1400 ng, less than about 1300 ng, less than about 1200 ng, less than about 1100 ng, less than about 1000 ng, less than about 900 ng, less than about 800 ng, less than about 700 ng, less than about 600 ng, less than about 500 ng, less than about 400 ng, less than about 300 ng, less than about 200 ng, less than about 150 ng, less than about 100 ng, less than about 95 ng, less than about 90 ng, less than about 85 ng, less than about 80 ng, less than about 75 ng, less than about 70 ng, less than about 65 ng, less than about 60 ng, less than about 55 ng, less than about 50 ng, less than about 45 ng, less than about 40 ng, less than about 35 ng, less than about 30 ng, less than about 25 ng, less than about 20 ng, less than about 15 ng, less than about 10 ng, or less than about 5 ng. In some embodiments, methods provided herein for selecting a subject for increased monitoring include detecting a genetic alteration (e.g., one or more genetic alterations) in circulating tumor DNA present in cell-free DNA, where the circulating tumor DNA represents 100% of the cell-free DNA. In some embodiments, methods provided herein for selecting a subject for increased monitoring include detecting a genetic alteration (e.g., one or more genetic alterations) in circulating tumor DNA present in cell-free DNA, where the circulating tumor DNA represents less than 100% of the cell-free DNA, e.g. about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, about 0.95%, about 0.90%, about 0.85%, about 0.80%, about 0.75%, about 0.70%, about 0.65%, about 0.60%, about 0.55%, about 0.50%, about 0.45%, about 0.40%, about 0.35%, about 0.30%, about 0.25%, about 0.20%, about 0.15%, about 0.10%, about 0.09%, about 0.08%, about 0.07%, about 0.06%, about 0.05% of the cell-free DNA, or less.

In some embodiments, methods provided herein can be used to select a subject for increased monitoring at a time period prior to diagnosis of the subject with an early-stage cancer. For example, methods provided herein for selecting a subject for increased monitoring can be used when a subject has not been diagnosed with cancer and/or when a subject is not known to harbor a cancer cell.

In some embodiments, a cancer cell mutation that is detected in a subject that is selected for increased monitoring by any of the variety of methods disclosed herein is present in a cancer cell present in the subject. For example, a cancer cell mutation listed in Table S7 that is detected in a subject that is selected for increased monitoring using any of the variety of methods disclosed herein can be present in a cancer cell present in the subject.

In some embodiments, a cancer cell mutation that is detected in a subject that is selected for increased monitoring by any of the variety of methods disclosed herein can be different from a blood proliferative disorder mutation or germline alteration (e.g., the cancer cell mutation is not a blood proliferative disorder mutation or germline alteration). For example, a cancer cell mutation that is detected in a subject that is selected for increased monitoring by any of the variety of methods disclosed herein can be different from a blood proliferative disorder mutation in a gene listed in Table S5, or different from a blood proliferative disorder mutation listed in Table S5. Additionally or alternatively, a cancer cell mutation that is detected in a subject that is selected for increased monitoring by any of the variety of methods disclosed herein can be different from a germline alteration in a gene listed in Table S6, or different from a germline alteration listed in Table S6.

In some embodiments, a subject selected for increased monitoring can be administered a diagnostic test (e.g., any of the diagnostic tests disclosed herein) at an increased frequency compared to a subject that has not been selected for increased monitoring. For example, a subject selected for increased monitoring can be administered a diagnostic test at a frequency of twice daily, daily, bi-weekly, weekly, bi-monthly, monthly, quarterly, semi-annually, annually, or any at frequency therein. In some embodiments, a subject selected for increased monitoring can be administered a one or more additional diagnostic tests compared to a subject that has not been selected for increased monitoring. For example, a subject selected for increased monitoring can be administered two diagnostic tests, whereas a subject that has not been selected for increased monitoring is administered only a single diagnostic test (or no diagnostic tests).

In some embodiments, a subject that has been selected for increased monitoring can also be selected for further diagnostic testing. As will be recognized by those of skill in the art, once the presence of a cancer cell has been identified (e.g., by any of the variety of methods disclosed herein), it may be beneficial for the subject to undergo both increased monitoring (e.g., to assess the progression of the tumor or cancer in the subject and/or to assess the development of additional cancer cell mutations), and further diagnostic testing (e.g., to determine the size and/or exact location of the tumor harboring the cancer cell).

In some embodiments, a therapeutic intervention is administered to the subject that is selected for increased monitoring after a cancer cell mutation is detected. Any of the therapeutic interventions disclosed herein or known in the art can be administered. For example, a subject that has been selected for increased monitoring can be further monitored, and a therapeutic intervention can be administered if the presence of the cancer cell is maintained throughout the increased monitoring period. Additionally or alternatively, a subject that has been selected for increased monitoring can be administered a therapeutic intervention, and further monitored as the therapeutic intervention progresses. In some embodiments, after a subject that has been selected for increased monitoring has been administered a therapeutic intervention, the increased monitoring will reveal one or more additional cancer cell mutations. In some embodiments, such one or more additional cancer cell mutations will provide cause to administer a different therapeutic intervention (e.g., a resistance mutation may arise in a cancer cell during the therapeutic intervention, which cancer cell harboring the resistance mutation is resistance to the original therapeutic intervention).

Selecting a Subject for Therapeutic Intervention

Also provided herein are methods for selecting a subject for therapeutic intervention (e.g., any of the therapeutic interventions disclosed herein). In some embodiments, methods for selecting a subject for therapeutic intervention include detecting one or more genetic alterations in cell-free DNA in a biological sample isolated from the subject, identifying the presence of circulating tumor DNA when at least one of the detected genetic alterations in the cell-free DNA is a cancer cell mutation, and selecting a subject for therapeutic intervention when the presence of circulating tumor DNA is identified. In some embodiments, the step of detecting is performed when the subject is not known to harbor a cancer cell.

In some embodiments, the biological sample is isolated from subject. Any suitable biological sample that contains cell-free DNA can be used in accordance with any of the variety of methods disclosed herein. For example, the biological sample can include blood, plasma, urine, cerebro-spinal fluid, saliva, sputum, broncho-alveolar lavage, bile, lymphatic fluid, cyst fluid, stool, ascites, and combinations thereof. Methods of isolating biological samples from a subject are known to those of ordinary skill in the art.

In some embodiments, the step of detecting a genetic alteration (e.g., one or more genetic alterations) in cell-free DNA is performed using one or more of the methods described herein (e.g., a targeted capture method, a next-generation sequencing method, and an array-based method, or any combinations thereof).

In some embodiments, methods provided herein for selecting a subject for therapeutic intervention include detecting a genetic alteration (e.g., one or more genetic alterations) in circulating tumor DNA present in cell-free DNA, where the cell-free DNA is present in an amount less than about 1500 ng, e.g., less than about 1400 ng, less than about 1300 ng, less than about 1200 ng, less than about 1100 ng, less than about 1000 ng, less than about 900 ng, less than about 800 ng, less than about 700 ng, less than about 600 ng, less than about 500 ng, less than about 400 ng, less than about 300 ng, less than about 200 ng, less than about 150 ng, less than about 100 ng, less than about 95 ng, less than about 90 ng, less than about 85 ng, less than about 80 ng, less than about 75 ng, less than about 70 ng, less than about 65 ng, less than about 60 ng, less than about 55 ng, less than about 50 ng, less than about 45 ng, less than about 40 ng, less than about 35 ng, less than about 30 ng, less than about 25 ng, less than about 20 ng, less than about 15 ng, less than about 10 ng, or less than about 5 ng. In some embodiments, methods provided herein for selecting a subject for therapeutic intervention include detecting a genetic alteration (e.g., one or more genetic alterations) in circulating tumor DNA present in cell-free DNA, where the circulating tumor DNA represents 100% of the cell-free DNA. In some embodiments, methods provided herein for selecting a subject for therapeutic intervention include detecting a genetic alteration (e.g., one or more genetic alterations) in circulating tumor DNA present in cell-free DNA, where the circulating tumor DNA represents less than 100% of the cell-free DNA, e.g. about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, about 0.95%, about 0.90%, about 0.85%, about 0.80%, about 0.75%, about 0.70%, about 0.65%, about 0.60%, about 0.55%, about 0.50%, about 0.45%, about 0.40%, about 0.35%, about 0.30%, about 0.25%, about 0.20%, about 0.15%, about 0.10%, about 0.09%, about 0.08%, about 0.07%, about 0.06%, about 0.05% of the cell-free DNA, or less.

In some embodiments, methods provided herein can be used to select a subject for therapeutic intervention at a time period prior to diagnosis of the subject with an early-stage cancer. For example, methods provided herein for selecting a subject for therapeutic intervention can be used when a subject has not been diagnosed with cancer and/or when a subject is not known to harbor a cancer cell.

In some embodiments, a cancer cell mutation that is detected in a subject that is selected for therapeutic intervention by any of the variety of methods disclosed herein is present in a cancer cell present in the subject. For example, a cancer cell mutation listed in Table S7 that is detected in a subject that is selected for therapeutic intervention using any of the variety of methods disclosed herein can be present in a cancer cell present in the subject.

In some embodiments, a cancer cell mutation that is detected in a subject that is selected for therapeutic intervention by any of the variety of methods disclosed herein can be different from a blood proliferative disorder mutation or germline alteration (e.g., the cancer cell mutation is not a blood proliferative disorder mutation or germline alteration). For example, a cancer cell mutation that is detected in a subject that is selected for therapeutic intervention by any of the variety of methods disclosed herein can be different from a blood proliferative disorder mutation in a gene listed in Table S5, or different from a blood proliferative disorder mutation listed in Table S5. Additionally or alternatively, a cancer cell mutation that is detected in a subject that is selected for therapeutic intervention by any of the variety of methods disclosed herein can be different from a germline alteration in a gene listed in Table S6, or different from a germline alteration listed in Table S6.

In some embodiments, a subject selected for therapeutic intervention can be selected for further diagnostic testing. In some embodiments, a subject selected for therapeutic intervention can be administered a diagnostic test (e.g., any of the diagnostic tests disclosed herein). In some embodiments, a subject selected for therapeutic intervention can be selected for increased monitoring. For example, a subject selected a therapeutic intervention and for increased monitoring can be administered a diagnostic test at a frequency of twice daily, daily, bi-weekly, weekly, bi-monthly, monthly, quarterly, semi-annually, annually, or any at frequency therein. In some embodiments, a subject selected for therapeutic intervention and increased monitoring can be administered a one or more additional diagnostic tests compared to a subject that has been selected for therapeutic intervention, but not been selected for increased monitoring. For example, a subject selected for therapeutic intervention and increased monitoring can be administered two diagnostic tests, whereas a subject that has only been selected for therapeutic intervention is administered only a single diagnostic test (or no diagnostic tests).

In some embodiments, a therapeutic intervention is administered to the subject that is selected for therapeutic intervention after a cancer cell mutation is detected. Any of the therapeutic interventions disclosed herein or known in the art can be administered. A subject that has been selected for therapeutic intervention can be monitored further, and a therapeutic intervention can be administered if the presence of the cancer cell is maintained throughout the increased monitoring period. Additionally or alternatively, a subject that has been selected for therapeutic intervention can be administered a therapeutic intervention, and monitored further as the therapeutic intervention progresses. In some embodiments, after a subject that has been selected for therapeutic intervention has been administered a therapeutic intervention, the increased monitoring will reveal one or more additional cancer cell mutations. In some embodiments, such one or more additional cancer cell mutations will provide cause to select the subject for a different therapeutic intervention and/or to administer a different therapeutic intervention (e.g., a resistance mutation may arise during the therapeutic intervention, which resistance mutant is resistance to the original therapeutic intervention).

Selecting a Therapeutic Intervention for a Subject

Also provided herein are methods for selecting a therapeutic intervention (e.g., any of the therapeutic interventions disclosed herein) for a subject. In some embodiments, methods for selecting a therapeutic intervention for a subject include detecting one or more genetic alterations in cell-free DNA in a biological sample isolated from the subject, identifying the presence of circulating tumor DNA when at least one of the detected genetic alterations in the cell-free DNA is a cancer cell mutation, and selecting a therapeutic intervention for a subject when the presence of circulating tumor DNA is identified. In some embodiments, the step of detecting is performed when the subject is not known to harbor a cancer cell.

In some embodiments, the biological sample is isolated from subject. Any suitable biological sample that contains cell-free DNA can be used in accordance with any of the variety of methods disclosed herein. For example, the biological sample can include blood, plasma, urine, cerebrospinal fluid, saliva, sputum, broncho-alveolar lavage, bile, lymphatic fluid, cyst fluid, stool, ascites, and combinations thereof. Methods of isolating biological samples from a subject are known to those of ordinary skill in the art.

In some embodiments, the step of detecting a genetic alteration (e.g., one or more genetic alterations) in cell-free DNA is performed using one or more of the methods described herein (e.g., a targeted capture method, a next-generation sequencing method, and an array-based method, or any combinations thereof).

In some embodiments, methods provided herein for selecting a therapeutic intervention for a subject include detecting a genetic alteration (e.g., one or more genetic alterations) in circulating tumor DNA present in cell-free DNA, where the cell-free DNA is present in an amount less than about 1500 ng, e.g., less than about 1400 ng, less than about 1300 ng, less than about 1200 ng, less than about 1100 ng, less than about 1000 ng, less than about 900 ng, less than about 800 ng, less than about 700 ng, less than about 600 ng, less than about 500 ng, less than about 400 ng, less than about 300 ng, less than about 200 ng, less than about 150 ng, less than about 100 ng, less than about 95 ng, less than about 90 ng, less than about 85 ng, less than about 80 ng, less than about 75 ng, less than about 70 ng, less than about 65 ng, less than about 60 ng, less than about 55 ng, less than about 50 ng, less than about 45 ng, less than about 40 ng, less than about 35 ng, less than about 30 ng, less than about 25 ng, less than about 20 ng, less than about 15 ng, less than about 10 ng, or less than about 5 ng. In some embodiments, methods provided herein for selecting a therapeutic intervention for a subject include detecting a genetic alteration (e.g., one or more genetic alterations) in circulating tumor DNA present in cell-free DNA, where the circulating tumor DNA represents less than about where the circulating tumor DNA represents 100% of the cell-free DNA. In some embodiments, methods provided herein for selecting a therapeutic intervention for a subject include detecting a genetic alteration (e.g., one or more genetic alterations) in circulating tumor DNA present in cell-free DNA, where the circulating tumor DNA represents less than about where the circulating tumor DNA represents less than 100% of the cell-free DNA, e.g. about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, about 0.95%, about 0.90%, about 0.85%, about 0.80%, about 0.75%, about 0.70%, about 0.65%, about 0.60%, about 0.55%, about 0.50%, about 0.45%, about 0.40%, about 0.35%, about 0.30%, about 0.25%, about 0.20%, about 0.15%, about 0.10%, about 0.09%, about 0.08%, about 0.07%, about 0.06%, about 0.05% of the cell-free DNA, or less.

In some embodiments, methods provided herein can be used to select a therapeutic intervention for a subject at a time period prior to diagnosis of the subject with an early-stage cancer. For example, methods provided herein for selecting a therapeutic intervention for a subject can be used when a subject has not been diagnosed with cancer and/or when a subject is not known to harbor a cancer cell.

In some embodiments, a cancer cell mutation that is detected in a subject for which a therapeutic intervention has been selected by any of the variety of methods disclosed herein is present in a cancer cell present in the subject. For example, a cancer cell mutation listed in Table S7 that is detected in a subject for which a therapeutic intervention has been selected using any of the variety of methods disclosed herein can be present in a cancer cell present in the subject.

In some embodiments, a cancer cell mutation that is detected in a subject for which a therapeutic intervention has been selected by any of the variety of methods disclosed herein can be different from a blood proliferative disorder mutation or germline alteration (e.g., the cancer cell mutation is not a blood proliferative disorder mutation or germline alteration). For example, a cancer cell mutation that is detected in a subject for which a therapeutic intervention has been selected by any of the variety of methods disclosed herein can be different from a blood proliferative disorder mutation in a gene listed in Table S5, or different from a blood proliferative disorder mutation listed in Table S5. Additionally or alternatively, a cancer cell mutation that is detected in a subject for which a therapeutic intervention has been selected by any of the variety of methods disclosed herein can be different from a germline alteration in a gene listed in Table S6, or different from a germline alteration listed in Table S6.

In some embodiments, a subject for which a therapeutic intervention has been selected can be selected for further diagnostic testing. In some embodiments, a subject for which a therapeutic intervention has been selected can be administered a diagnostic test (e.g., any of the diagnostic tests disclosed herein). In some embodiments, a subject for which a therapeutic intervention has been selected can also be selected for increased monitoring. For example, a subject for which a therapeutic intervention has been selected and for which increased monitoring has been selected can be administered a diagnostic test at a frequency of twice daily, daily, bi-weekly, weekly, bi-monthly, monthly, quarterly, semi-annually, annually, or any at frequency therein. In some embodiments, a subject for which a therapeutic intervention and increased monitoring has been selected can be administered a one or more additional diagnostic tests compared to a subject that has been selected for therapeutic intervention, but not been selected for increased monitoring. For example, a subject for which a therapeutic intervention and increased monitoring has been selected can be administered two diagnostic tests, whereas a subject that has only been selected for therapeutic intervention is administered only a single diagnostic test (or no diagnostic tests).

In some embodiments, a therapeutic intervention is administered to the subject for which a therapeutic intervention has been selected after a cancer cell mutation is detected. Any of the therapeutic interventions disclosed herein or known in the art can be administered. A subject for which a therapeutic intervention has been selected can be monitored further, and a therapeutic intervention can be administered if the presence of the cancer cell is maintained throughout the increased monitoring period. Additionally or alternatively, a subject for which a therapeutic intervention has been selected can be administered a therapeutic intervention, and monitored further as the therapeutic intervention progresses. In some embodiments, after a subject for which a therapeutic intervention has been selected has been administered a therapeutic intervention, the increased monitoring will reveal one or more additional cancer cell mutations. In some embodiments, such one or more additional cancer cell mutations will provide cause to select a different therapeutic intervention for the subject and/or to administer a different therapeutic intervention (e.g., a resistance mutation may arise during the therapeutic intervention, which resistance mutant is resistance to the original therapeutic intervention).

Identifying the Presence of a Cancer Cell in a Subject by Detecting Cell-Free DNA and/or Circulating Tumor DNA Levels In some embodiments, methods for identifying the presence of a cancer cell in a subject include detecting the level of cell-free DNA in a subject, the level of circulating tumor DNA, or both, comparing the detected level of cell-free DNA and/or circulating tumor DNA in the subject to a reference level of cell-free DNA and/or circulating tumor DNA, and determining the presence of the cancer cell in the subject when the detected level of cell-free DNA and/or circulating tumor DNA in the subject is higher than the reference level of cell-free DNA and/or circulating tumor DNA. In some embodiments, the step of detecting is performed when the subject is not known to harbor a cancer cell. In some embodiments, the cancer cell that is detected can be from any cancer disclosed herein including, without limitation, colorectal cancer, lung cancer, breast cancer, or ovarian cancer.

In some embodiments, the detected level of cell-free DNA and/or circulating tumor DNA in the subject identified as harboring a cancer cell is about 2-fold, 3-fold, 4-fold, 5-fold, 6-fold, 7-fold, 8-fold, 9-fold, 10-fold higher or more than a reference level of cell-free DNA and/or circulating tumor DNA. A reference level of cell-free DNA and/or circulating tumor DNA can be any level of cell-free DNA and/or circulating tumor DNA that is not correlated or associated with the presence of a cancer cell in the subject. For example, a reference level of cell-free DNA and/or circulating tumor DNA can be a level of cell-free DNA and/or circulating tumor DNA that is present in a subject before the subject develops cancer. As another example, a reference level of cell-free DNA and/or circulating tumor DNA can be a level of cell-free DNA and/or circulating tumor DNA that is present in a subject at a time period prior to the identification of the subject as harboring a cancer cell. For example, a reference level of cell-free DNA and/or circulating tumor DNA can be a level of cell-free DNA and/or circulating tumor DNA that is present in a subject about 1 month, 2 months, 3 months, 4 months, 5 months, 6 months, 1 year, 2 years, 3 years, 4 years, 5 years, 10 years, or more (or any time period between these time periods) to the identification of the subject as harboring a cancer cell. As another example, a reference level of cell-free DNA and/or circulating tumor DNA can be a level of cell-free DNA and/or circulating tumor DNA that is present in a reference subject that does not harbor a cancer cell.

In some embodiments, the biological sample is isolated from subject. Any suitable biological sample that contains cell-free DNA and/or circulating tumor DNA can be used in accordance with any of the variety of methods disclosed herein. For example, the biological sample can include blood, plasma, urine, cerebrospinal fluid, saliva, sputum, broncho-alveolar lavage, bile, lymphatic fluid, cyst fluid, stool, ascites, and combinations thereof. Methods of isolating biological samples from a subject are known to those of ordinary skill in the art.

In some embodiments, methods provided herein that include detecting the level of cell-free DNA and/or circulating tumor DNA in a subject and comparing that level to a reference level of cell-free DNA and/or circulating tumor DNA can be used to detect the presence of a cancer cell in a subject at a time period prior to diagnosis of the subject with an early-stage cancer. For example, methods provided herein that include detecting the level of cell-free DNA and/or circulating tumor DNA in a subject and comparing that level to a reference level of cell-free DNA and/or circulating tumor DNA can be used when a subject has not been diagnosed with cancer and/or when a subject is not known to harbor a cancer cell. In some embodiments, a therapeutic intervention is administered to the subject after the presence of a cancer cell mutation is identified. Any of the therapeutic interventions disclosed herein or known in the art can be administered.

In some embodiments, methods provided herein that include detecting the level of cell-free DNA and/or circulating tumor DNA in a subject and comparing that level to a reference level of cell-free DNA and/or circulating tumor DNA to identify the presence of a cancer cell in a subject can be used to determine that the subject exhibits a poor prognosis (e.g., a poor prognosis relative to a reference subject that does not harbor a cancer cell). In some embodiments, a poor prognosis can be shorter progression-free survival, lower overall survival, or both.

In some embodiments, methods provided herein that include detecting the level of cell-free DNA and/or circulating tumor DNA in a subject and comparing that level to a reference level of cell-free DNA and/or circulating tumor DNA can be used to identify the presence of a cancer cell in a subject at a time period prior to diagnosis of the subject with an early-stage cancer (e.g., when the subject is not known to harbor a cancer cell), after which a therapeutic intervention (e.g., any of the therapeutic interventions described herein) can be administered to the subject. In some embodiments, methods provided herein that include detecting the level of cell-free DNA and/or circulating tumor DNA in a subject and comparing that level to a reference level of cell-free DNA and/or circulating tumor DNA can be used to determine that a subject has an early-stage cancer before other methods (e.g., conventional diagnostic methods) are capable of determining the presence of cancer. In some embodiments, a therapeutic intervention administered to a subject that is determined to have an early-stage cancer using any of the variety of methods provided herein is more effective that if the therapeutic intervention were to be administered to a subject at a later time (e.g., after the cancer has progressed beyond early-stage). In some embodiments, a therapeutic intervention administered to a subject determined to have an early-stage cancer can be administered at a lower frequency, duration, and/or dose. For example, a therapeutic intervention can be a targeted therapy (e.g. a kinase inhibitor, and antibody, a bispecific antibody, etc.), which targeted therapy is administered at a lower frequency, duration, and/or dose than if the subject had cancer that was not early-stage (e.g., than if the subject had a late-stage cancer). In some embodiments, a therapeutic intervention is administered to a subject identified as having an early-stage cancer at a frequency that is about 2-fold, 3-fold, 4-fold, 5-fold, 6-fold, 7-fold, 8-fold, 9-fold, 10-fold or more less frequent that if the subject had a cancer that was not early-stage. In some embodiments, a therapeutic intervention is administered to a subject identified as having an early-stage cancer for a duration that is reduced by about 2-fold, 3-fold, 4-fold, 5-fold, 6-fold, 7-fold, 8-fold, 9-fold, 10-fold or more that if the subject had a cancer that was not early-stage. In some embodiments, a therapeutic intervention is administered to a subject identified as having an early-stage cancer at a dosage that is about 2-fold, 3-fold, 4-fold, 5-fold, 6-fold, 7-fold, 8-fold, 9-fold, 10-fold or more less that if the subject had a cancer that was not early-stage. In some embodiments, a therapeutic intervention administered to a subject determined to have an early-stage cancer can be a surgical intervention, and the surgical intervention can be less invasive and/or last for a shorter period of time than if the subject had cancer that was not early-stage (e.g., than if the subject had a late-stage cancer). As one non-limiting example, methods provided herein can be used to determine that a subject has an early-stage cancer, and surgical resection can be used to remove cancer cells or a tumor from the subject. As another non-limiting example, methods provided herein can be used to determine that a subject has an early-stage cancer, and a targeted therapy that is specific for the type of cancer, cancer cell, or cancer cell mutation can be administered to the subject. In some embodiments, a therapeutic intervention administered after the subject has been determined to have an early-stage cancer (e.g. by any of the variety of methods provided herein) results in the cancer being cured. For example, the therapeutic intervention can result in complete elimination of the detected cancer in the subject.

Detecting a Blood Cell Proliferation Disorder in a Subject

Also provided herein are methods for detecting a blood cell proliferation mutation (e.g., any of the blood cell proliferation mutations described herein) in a subject. In some embodiments, methods for detecting a blood cell proliferation mutation in a subject include detecting one or more genetic alterations in cell-free DNA in a biological sample isolated from the subject, and identifying the presence of the blood cell proliferation mutation in the subject when at least one of the detected genetic alterations in the cell-free DNA is a blood cell proliferation mutation. In some embodiments, the step of detecting is performed when the subject is not known to harbor a blood cell proliferation disorder, a blood cell proliferation mutation, or both.

Also provided herein are methods for detecting a blood cell proliferation disorder (e.g., any of the blood cell proliferation disorders described herein) in a subject. In some embodiments, methods for detecting a blood cell proliferation mutation in a subject include detecting one or more genetic alterations in cell-free DNA in a biological sample isolated from the subject, identifying the presence of the blood cell proliferation mutation in the subject when at least one of the detected genetic alterations in the cell-free DNA is a blood cell proliferation mutation, and identifying the subject as having a blood cell proliferation disorder when the presence of the blood cell proliferation mutation is identified. In some embodiments, the step of detecting is performed when the subject is not known to harbor a blood cell proliferation disorder, a blood cell proliferation mutation, or both.

In some embodiments, the biological sample is isolated from subject. Any suitable biological sample that contains cell-free DNA can be used in accordance with any of the variety of methods disclosed herein. For example, the biological sample can include blood, plasma, urine, cerebrospinal fluid, saliva, sputum, broncho-alveolar lavage, bile, lymphatic fluid, cyst fluid, stool, ascites, and combinations thereof. Methods of isolating biological samples from a subject are known to those of ordinary skill in the art.

In some embodiments, the step of detecting a blood cell proliferation mutation, a blood cell proliferation disorder, or both in a subject includes detecting a genetic alteration (e.g., one or more genetic alterations) in cell-free DNA, wherein detecting a genetic alteration is performed using one or more of the methods described herein (e.g., a targeted capture method, a next-generation sequencing method, and an array-based method, or any combinations thereof).

In some embodiments, methods provided herein can be used to identify the presence of a blood cell proliferation mutation, a blood cell proliferation disorder, or both in a subject by detecting a genetic alteration (e.g., one or more genetic alterations) in cell-free DNA, where the cell-free DNA is present in an amount less than about 1500 ng, e.g., less than about 1400 ng, less than about 1300 ng, less than about 1200 ng, less than about 1100 ng, less than about 1000 ng, less than about 900 ng, less than about 800 ng, less than about 700 ng, less than about 600 ng, less than about 500 ng, less than about 400 ng, less than about 300 ng, less than about 200 ng, less than about 150 ng, less than about 100 ng, less than about 95 ng, less than about 90 ng, less than about 85 ng, less than about 80 ng, less than about 75 ng, less than about 70 ng, less than about 65 ng, less than about 60 ng, less than about 55 ng, less than about 50 ng, less than about 45 ng, less than about 40 ng, less than about 35 ng, less than about 30 ng, less than about 25 ng, less than about 20 ng, less than about 15 ng, less than about 10 ng, or less than about 5 ng.

In some embodiments, methods provided herein can be used to detect the presence of a blood cell proliferation mutation, a blood cell proliferation disorder, or both in a subject at a time period prior to diagnosis of the subject with a blood cell disorder. In some embodiments, a blood cell proliferation mutation that is identified in a subject by any of the variety of methods disclosed herein is a blood cell proliferation mutation present in a gene listed in Table S5. In some embodiments, a blood cell proliferation mutation that is identified in a subject by any of the variety of methods disclosed herein is a blood cell proliferation mutation listed in Table S5. In some embodiments, when a blood cell proliferation mutation is identified in a subject by any of the variety of methods disclosed herein, the presence of the blood cell proliferation disorder in the subject is confirmed through subsequent diagnostic testing (e.g., diagnostic scans, biopsies, molecular-based techniques to confirm the presence of the blood cell proliferation mutation, etc.).

In some embodiments, a cell harboring a blood cell proliferation mutation in a subject (e.g., a pre-leukemic cell) that is identified by any of the variety of methods disclosed herein does not include a cancer cell mutation or germline alteration. For example, a cell harboring a blood cell proliferation mutation that is identified by any of the variety of methods disclosed herein can include a blood cell proliferation mutation that is different from a cancer cell mutation in a gene listed in Table S7, or different from a cancer cell mutation listed in Table S7. Additionally or alternatively, a cell harboring a blood cell proliferation mutation that is identified by any of the variety of methods disclosed herein can include a cell harboring a blood cell proliferation mutation that is different from a germline alteration in a gene listed in Table S6, or different from a germline alteration listed in Table S6.

In some embodiments, after a subject is identified as having a blood cell proliferation mutation by any of the variety of methods disclosed herein, the subject is selected for increased monitoring. For example, the subject can be selected for increased monitoring to watch for the development of a blood cell proliferation disorder (e.g. leukemia or lymphoma).

In some embodiments, after a subject is identified as having a blood cell proliferation disorder by any of the variety of methods disclosed herein, the subject is administered a blood cell proliferation treatment. Blood cell proliferation treatments include, without limitation, chemotherapy or targeted therapies. In some embodiments, a subject is identified as having an early-stage blood cell proliferation disorder by any of the variety of methods disclosed herein (e.g., prior to the time conventional detection methods are capable of identifying the blood cell proliferation disorder). In some embodiments, after a subject is identified as having an early-stage blood cell proliferation disorder, the subject is administered a blood cell proliferation treatment. In some embodiments, a blood cell proliferation treatment is more effective than if the subject did not have an early-stage blood cell proliferation disorder (e.g., than if the subject had a late-stage blood cell proliferation disorder). In some embodiments, a blood cell proliferation treatment administered to a subject identified as having an early-stage blood cell proliferation disorder cures the blood cell proliferation disorder. For example, the blood cell proliferation treatment can result in complete elimination of the detected blood cell proliferation disorder in the subject.

Detecting a Germline Alteration in a Subject

Also provided herein are methods for detecting a germline alteration (e.g., any of the germline alterations disclosed herein) in a subject. In some embodiments, methods for detecting a germline alteration in a subject include detecting one or more genetic alterations in cell-free DNA in a biological sample isolated from the subject, and identifying the presence of the germline alteration in the subject when at least one of the detected genetic alterations in the cell-free DNA is a germline alteration. In some embodiments, the step of detecting is performed when the subject is not known to harbor a germline alteration.

Also provided herein are methods for detecting a disorder related to a germline alteration in a subject. In some embodiments, methods for detecting a disorder related to a germline alteration in a subject include detecting one or more genetic alterations in cell-free DNA in a biological sample isolated from the subject, identifying the presence of the germline alteration in the subject when at least one of the detected genetic alterations in the cell-free DNA is a germline alteration, and identifying the subject as having a disorder related to a germline alteration when the presence of the germline alteration is identified. In some embodiments, the step of detecting is performed when the subject is not known to harbor germline alteration.

In some embodiments, the biological sample is isolated from subject. Any suitable biological sample that contains cell-free DNA can be used in accordance with any of the variety of methods disclosed herein. For example, the biological sample can include blood, plasma, urine, cerebrospinal fluid, saliva, sputum, broncho-alveolar lavage, bile, lymphatic fluid, cyst fluid, stool, ascites, and combinations thereof. Methods of isolating biological samples from a subject are known to those of ordinary skill in the art.

In some embodiments, the step of detecting a germline alteration in a subject includes detecting a genetic alteration (e.g., one or more genetic alterations) in cell-free DNA, wherein detecting a genetic alteration is performed using one or more of the methods described herein (e.g., a targeted capture method, a next-generation sequencing method, and an array-based method, or any combinations thereof).

In some embodiments, methods provided herein can be used to identify the presence of a germline alteration in a subject by detecting a genetic alteration (e.g., one or more genetic alterations) in cell-free DNA, where the cell-free DNA is present in an amount less than about 1500 ng, e.g., less than about 1400 ng, less than about 1300 ng, less than about 1200 ng, less than about 1100 ng, less than about 1000 ng, less than about 900 ng, less than about 800 ng, less than about 700 ng, less than about 600 ng, less than about 500 ng, less than about 400 ng, less than about 300 ng, less than about 200 ng, less than about 150 ng, less than about 100 ng, less than about 95 ng, less than about 90 ng, less than about 85 ng, less than about 80 ng, less than about 75 ng, less than about 70 ng, less than about 65 ng, less than about 60 ng, less than about 55 ng, less than about 50 ng, less than about 45 ng, less than about 40 ng, less than about 35 ng, less than about 30 ng, less than about 25 ng, less than about 20 ng, less than about 15 ng, less than about 10 ng, or less than about 5 ng.

In some embodiments, methods provided herein can be used to detect the presence of a germline alteration in a subject at a time period prior to diagnosis of the subject as having the germline alteration. In some embodiments, a germline alteration that is identified in a subject by any of the variety of methods disclosed herein is a germline alteration present in a gene listed in Table S6. In some embodiments, a germline alteration that is identified in a subject by any of the variety of methods disclosed herein is a germline alteration listed in Table S6. In some embodiments, when a germline alteration is identified in a subject by any of the variety of methods disclosed herein, the presence of the germline alteration in the subject is confirmed through subsequent diagnostic testing (e.g., diagnostic scans, biopsies, molecular-based techniques to confirm the presence of the blood cell proliferation mutation, etc.).

In some embodiments, a cell harboring a germline alteration in a subject that is identified by any of the variety of methods disclosed herein does not include a cancer cell mutation or blood cell proliferation mutation. For example, a cell harboring a germline alteration that is identified by any of the variety of methods disclosed herein can include a germline alteration that is different from a cancer cell mutation in a gene listed in Table S7, or different from a cancer cell mutation listed in Table S7. Additionally or alternatively, a cell harboring a germline alteration that is identified by any of the variety of methods disclosed herein can include a cell harboring a germline alteration that is different from a blood cell proliferation mutation in a gene listed in Table S5, or different from a blood cell proliferation mutation listed in Table S5.

In some embodiments, a subject identified as having a germline alteration (e.g., a cell harboring a germline alteration) is selected for increased monitoring. In some embodiments, a subject identified as having a germline alteration (e.g., a cell harboring a germline alteration) is monitored for the development of cancer. In some embodiments, a subject identified as having a germline alteration (e.g., a cell harboring a germline alteration) is monitored for loss of heterozygosity at the locus containing the germline alteration.

Distinguishing Subtypes of Cell-Free DNA

Also provided herein are methods for distinguishing in a subject subtypes of cell-free DNA having a genetic alteration. In some embodiments, methods for distinguishing in a subject subtypes of cell-free DNA having a genetic alteration include detecting one or more genetic alterations in cell-free DNA in a biological sample isolated from the subject, and (i) identifying the presence of circulating tumor DNA, the presence of a cancer cell mutation, and/or the presence of a cancer cell when at least one of the detected genetic alterations in the cell-free DNA is a cancer cell mutation, (ii) identifying the presence of a blood cell proliferation mutation and/or the presence of a blood cell proliferation disorder in the subject when at least one of the detected genetic alterations in the cell-free DNA is a blood cell proliferation mutation, or (iii) identifying the presence of a germline alteration in the subject when at least one of the detected genetic alterations in the cell-free DNA is a germline alteration. In some embodiments, the subject is not known to harbor a cancer cell, a cancer cell mutation, a cell associated with a bloodline proliferation disorder, a bloodline proliferation disorder mutation, and/or a germline alteration. In some embodiments, the subject is identified as harboring a cancer cell when presence of circulating tumor DNA is identified. In some embodiments, the subject is identified as having a blood cell proliferation disorder when presence of a blood cell proliferation mutation is identified.

In some embodiments, the biological sample is isolated from subject. Any suitable biological sample that contains cell-free DNA can be used in accordance with any of the variety of methods disclosed herein. For example, the biological sample can include blood, plasma, urine, cerebrospinal fluid, saliva, sputum, broncho-alveolar lavage, bile, lymphatic fluid, cyst fluid, stool, ascites, and combinations thereof. Methods of isolating biological samples from a subject are known to those of ordinary skill in the art.

In some embodiments, the step of detecting a cancer cell mutation, a blood cell proliferation mutation, and/or a germline alteration in a subject includes detecting a genetic alteration (e.g., one or more genetic alterations) in cell-free DNA, wherein detecting a genetic alteration is performed using one or more of the methods described herein (e.g., a targeted capture method, a next-generation sequencing method, and an array-based method, or any combinations thereof).

In some embodiments, methods provided herein can be used for distinguishing in a subject subtypes of cell-free DNA having a genetic alteration by detecting a genetic alteration (e.g., one or more genetic alterations) in cell-free DNA, where the cell-free DNA is present in an amount less than about 1500 ng, e.g., less than about 1400 ng, less than about 1300 ng, less than about 1200 ng, less than about 1100 ng, less than about 1000 ng, less than about 900 ng, less than about 800 ng, less than about 700 ng, less than about 600 ng, less than about 500 ng, less than about 400 ng, less than about 300 ng, less than about 200 ng, less than about 150 ng, less than about 100 ng, less than about 95 ng, less than about 90 ng, less than about 85 ng, less than about 80 ng, less than about 75 ng, less than about 70 ng, less than about 65 ng, less than about 60 ng, less than about 55 ng, less than about 50 ng, less than about 45 ng, less than about 40 ng, less than about 35 ng, less than about 30 ng, less than about 25 ng, less than about 20 ng, less than about 15 ng, less than about 10 ng, or less than about 5 ng.

In some embodiments, a cancer cell mutation that is detected by any of the variety of methods disclosed herein for distinguishing in a subject subtypes of cell-free DNA having a genetic alteration can be different from a blood proliferative disorder mutation or germline alteration (e.g., the cancer cell mutation is not a blood proliferative disorder mutation or germline alteration). For example, a cancer cell mutation that is detected by any of the variety of methods disclosed herein for distinguishing in a subject subtypes of cell-free DNA having a genetic alteration can be different from a blood proliferative disorder mutation in a gene listed in Table S5, or different from a blood proliferative disorder mutation listed in Table S5. Additionally or alternatively, a cancer cell mutation that is detected by any of the variety of methods disclosed herein for distinguishing in a subject subtypes of cell-free DNA having a genetic alteration can be different from a germline alteration in a gene listed in Table S6, or different from a germline alteration listed in Table S6.

In some embodiments, a blood cell proliferation mutation that is detected by any of the variety of methods disclosed herein for distinguishing in a subject subtypes of cell-free DNA having a genetic alteration can be different from a cancer cell mutation or germline alteration (e.g., the blood cell proliferation mutation is not a cancer cell mutation or germline alteration). For example, a blood cell proliferation mutation that is detected by any of the variety of methods disclosed herein for distinguishing in a subject subtypes of cell-free DNA having a genetic alteration can be different from a cancer cell mutation in a gene listed in Table S7, or different from a cancer cell mutation listed in Table S7. Additionally or alternatively, a cancer cell mutation that is detected by any of the variety of methods disclosed herein for distinguishing in a subject subtypes of cell-free DNA having a genetic alteration can be different from a germline alteration in a gene listed in Table S6, or different from a germline alteration listed in Table S6.

In some embodiments, a germline alteration that is detected by any of the variety of methods disclosed herein for distinguishing in a subject subtypes of cell-free DNA having a genetic alteration can be different from a blood proliferative disorder mutation or cancer cell mutation (e.g., the germline alteration is not a blood proliferative disorder mutation or cancer cell mutation). For example, a germline alteration that is detected by any of the variety of methods disclosed herein for distinguishing in a subject subtypes of cell-free DNA having a genetic alteration can be different from a blood proliferative disorder mutation in a gene listed in Table S5, or different from a blood proliferative disorder mutation listed in Table S5. Additionally or alternatively, a germline alteration that is detected by any of the variety of methods disclosed herein for distinguishing in a subject subtypes of cell-free DNA having a genetic alteration can be different from a cancer cell mutation in a gene listed in Table S7, or different from a cancer cell mutation listed in Table S7.

Detecting Genetic Alterations

In some embodiments, the step of detecting a genetic alteration (e.g., one or more genetic alterations) in cell-free DNA is performed using a targeted capture method, a next-generation sequencing method, and an array-based method, or any combinations thereof. In some embodiments, the step of detecting a genetic alteration is performed using TEC-Seq, or a variation of TEC-Seq. The outline of performing the TEC-Seq method is shown in FIG. 1. For example, the step of detecting a genetic alteration can include the following steps: extracting cell-free DNA from blood, ligating a low complexity pool of dual index barcode adapters to the cell-free DNA to generate a plurality of barcode adapter-ligated cell-free DNA segments, capturing the plurality of barcode adapter-ligated cell-free DNA segments, sequencing the plurality of captured barcode adapter-ligated cell-free DNA segments, aligning the sequenced plurality of captured barcode adapter-ligated cell-free DNA segments to a reference genome, and identifying sequence alterations using aligned sequences of multiple distinct molecules containing identical redundant changes.

In some embodiments, the step of detecting a genetic alteration (e.g., one or more genetic alterations) in cell-free DNA is performed using sequencing technology (e.g., a next-generation). A variety of sequencing technologies are known in the art. For example, a variety of technologies for detection and characterization of circulating tumor DNA in cell-free DNA is described in Haber and Velculescu, Blood-Based Analyses of Cancer: Circulating Tumor Cells and Circulating Tumor DNA, Cancer Discov., Jun.; 4(6):650-61. doi: 10.1158/2159-8290.CD-13-1014, 2014, incorporated herein by reference in its entirety. Non-limiting examples of such techniques include SafeSeqs (Kinde et. al, Detection and quantification of rare mutations with massively parallel sequencing, Proc Natl Acad Sci USA; 108, 9530-5, 2011), OnTarget (Forshew et al., Noninvasive identification and monitoring of cancer mutations by targeted deep sequencing of plasma DNA, Sci Transl Med; 4:136ra68, 2012), and TamSeq (Thompson et al., Winnowing DNA for rare sequences: highly specific sequence and methylation based enrichment. PLoS ONE, 7:e31597, 2012), each of which is incorporated herein by reference in its entirety. In some embodiments, the step of detecting a genetic alteration (e.g., one or more genetic alterations) in cell-free DNA is performed using droplet digital PCR (ddPCR), a method that is known to be highly sensitive for mutation detection. In some embodiments, the step of detecting a genetic alteration (e.g., one or more genetic alterations) in cell-free DNA is performed using other sequencing technologies, including but not limited to, chain-termination techniques, shotgun techniques, sequencing-by-synthesis methods, methods that utilize microfluidics, other capture technologies, or any of the other sequencing techniques known in the art that are useful for detection of small amounts of DNA in a sample (e.g., circulating tumor DNA in a cell-free DNA sample).

In some embodiments, the step of detecting a genetic alteration (e.g., one or more genetic alterations) in cell-free DNA is performed using array-based methods. For example, the step of detecting a genetic alteration (e.g., one or more genetic alterations) in cell-free DNA is performed using a DNA microarray. In some embodiments, a DNA microarray can detect one more of a plurality of cancer cell mutations. In some embodiments, a DNA microarray can detect one or more of the cancer cell mutations listed in Table S7. In some embodiments, a DNA microarray can detect each of the cancer cell mutations listed in Table S7. In some embodiments, cell-free DNA is amplified prior to detecting the genetic alteration.

Non-limiting examples of array-based methods that can be used in any of the methods described herein, include: a complementary DNA (cDNA) microarray (Kumar et al. (2012) J. Pharm. Bioallied Sci. 4(1): 21-26; Laere et al. (2009) Methods Mol. Biol. 512: 71-98; Mackay et al. (2003) Oncogene 22: 2680-2688; Alizadeh et al. (1996) Nat. Genet. 14: 457-460), an oligonucleotide microarray (Kim et al. (2006) Carcinogenesis 27(3): 392-404; Lodes et al. (2009) PLoS One 4(7): e6229), a bacterial artificial chromosome (BAC) clone chip (Chung et al. (2004) Genome Res. 14(1): 188-196; Thomas et al. (2005) Genome Res. 15(12): 1831-1837), a single-nucleotide polymorphism (SNP) microarray (Mao et al. (2007) Curr. Genomics 8(4): 219-228; Jasmine et al. (2012) PLoS One 7(2): e31968), a microarray-based comparative genomic hybridization array (array-CGH) (Beers and Nederlof (2006) Breast Cancer Res. 8(3): 210; Pinkel et al. (2005) Nat. Genetics 37: S11-S17; Michels et al. (2007) Genet. Med. 9: 574-584), a molecular inversion probe (MIP) assay (Wang et al. (2012) Cancer Genet 205 (7-8): 341-55; Lin et al. (2010) BMC Genomics 11: 712). In some embodiments, the cDNA microarray is an Affymetrix microarray (Irizarry (2003) Nucleic Acids Res 31:e15; Dalma-Weiszhausz et al. (2006) Methods Enzymol. 410: 3-28), a NimbleGen microarray (Wei et al. (2008) Nucleic Acids Res 36(9): 2926-2938; Albert et al. (2007) Nat. Methods 4: 903-905), an Agilent microarray (Hughes et al. (2001) Nat. Biotechnol. 19(4): 342-347), or a BeadArray array (Liu et al. (2017) Biosens Bioelectron 92: 596-601). In some embodiments, the oligonucleotide microarray is a DNA tiling array (Mockler and Ecker (2005) Genomics 85(1): 1-15; Bertone et al. (2006) Genome Res 16(2): 271-281). Other suitable array-based methods are known in the art.

Detecting Early-Stage Cancer

In some embodiments, methods provided herein can be used when a subject has not been diagnosed with cancer. In some embodiments, methods provided herein can be used when a subject is not known to harbor a cancer cell. In some embodiments, a subject has not been diagnosed with cancer and/or is not known to harbor a cancer cell when the subject has not been diagnosed with cancer, has not been diagnosed with a late-stage cancer, has not been diagnosed with a stage IV cancer, has not been diagnosed with a stage III cancer, has not been diagnosed with a stage II cancer, has not been diagnosed with a stage I cancer, has not had a biopsy to confirm abnormal cellular growth and/or the presence of a tumor, and/or has not undergone a diagnostic scan to detect a cancer (e.g., a PET scan or an MRI). In some embodiments, a subject not having been diagnosed with cancer and/or not known to harbor a cancer cell has not been treated with a therapeutic intervention (e.g., has not been administered a chemotherapeutic agent and/or has not undergone surgical resection of a cancer). In some embodiments, methods provided herein can be used to detect an early-stage cancer in a subject when the subject has not been diagnosed with cancer and/or is not known to harbor a cancer cell. In some embodiments, the presence of a cancer cell is detected at a time period prior to diagnosis of the subject with an early-stage cancer.

Therapeutic Interventions

Also provided herein are therapeutic interventions for treating subjects identified as having early-stage cancers using one or more methods disclosed herein. In some embodiments, any of the variety of methods provided herein can be used to identify a subject as having an early-stage cancer, and the subject can be treated with a therapeutic intervention to reduce or eliminate the cancer. Exemplary therapeutic interventions include, without limitation, adoptive T cell therapy (e.g., chimeric antigen receptors and/or T cells having wild-type or modified T cell receptors), radiation therapy, surgery (e.g., surgical resection), and administration of one or more chemotherapeutic agents, administration of immune checkpoint inhibitors, targeted therapies such as kinase inhibitors (e.g., kinase inhibitors that target a particular genetic lesion, such as a translocation or mutation), signal transduction inhibitors, bispecific antibodies, and/or monoclonal antibodies. Such therapeutic interventions can be administered alone or in combination.

In some embodiments, the therapeutic intervention can include an immune checkpoint inhibitor. Non-limiting examples of immune checkpoint inhibitors include nivolumab (Opdivo), pembrolizumab (Keytruda), atezolizumab (tecentriq), avelumab (bavencio), durvalumab (imfinzi), ipilimumab (yervoy). See, e.g., Pardoll (2012) Nat. Rev Cancer 12: 252-264; Sun et al. (2017) Eur Rev Med Pharmacol Sci 21(6): 1198-1205; Hamanishi et al. (2015) J. Clin. Oncol. 33(34): 4015-22; Brahmer et al. (2012) N Engl J Med 366(26): 2455-65; Ricciuti et al. (2017) J. Thorac Oncol. 12(5): e51-e55; Ellis et al. (2017) Clin Lung Cancer pii: S1525-7304(17)30043-8; Zou and Awad (2017) Ann Oncol 28(4): 685-687; Sorscher (2017) N Engl J Med 376(10: 996-7; Hui et al. (2017) Ann Oncol 28(4): 874-881; Vansteenkiste et al. (2017) Expert Opin Biol Ther 17(6): 781-789; Hellmann et al. (2017) Lancet Oncol. 18(1): 31-41; Chen (2017) J. Chin Med Assoc 80(1): 7-14.

In some embodiments, the therapeutic intervention is adoptive T cell therapy (e.g., chimeric antigen receptors and/or T cells having wild-type or modified T cell receptors). See, e.g., Rosenberg and Restifo (2015) Science 348(6230): 62-68; Chang and Chen (2017) Trends Mol Med 23(5): 430-450; Yee and Lizee (2016) Cancer J. 23(2): 144-148; Chen et al. (2016) Oncoimmunology 6(2): e1273302; US 2016/0194404; US 2014/0050788; US 2014/0271635; U.S. Pat. No. 9,233,125; incorporated by reference in their entirety herein.

Non-limiting examples of chemotherapeutic agents include: amsacrine, azacitidine, axathioprine, bevacizumab (or an antigen-binding fragment thereof), bleomycin, busulfan, carboplatin, capecitabine, chlorambucil, cisplatin, cyclophosphamide, cytarabine, dacarbazine, daunorubicin, docetaxel, doxifluridine, doxorubicin, epirubicin, erlotinib hydrochlorides, etoposide, fiudarabine, floxuridine, fludarabine, fluorouracil, gemcitabine, hydroxyurea, idarubicin, ifosfamide, irinotecan, lomustine, mechlorethamine, melphalan, mercaptopurine, methotrxate, mitomycin, mitoxantrone, oxaliplatin, paclitaxel, pemetrexed, procarbazine, all-trans retinoic acid, streptozocin, tafluposide, temozolomide, teniposide, tioguanine, topotecan, uramustine, valrubicin, vinblastine, vincristine, vindesine, vinorelbine, and combinations thereof. Additional examples of anti-cancer therapies are known in the art; see, e.g. the guidelines for therapy from the American Society of Clinical Oncology (ASCO), European Society for Medical Oncology (ESMO), or National Comprehensive Cancer Network (NCCN).

In some embodiments, identifying a subject as having an early-stage cancer through the use of any of the variety of methods provided herein permits the use of a therapeutic intervention that would otherwise not be available to the subject (e.g., if the cancer were not diagnosed until it was late-stage). For example, surgical resection is often in insufficient to fully treat a cancer once it has progressed beyond the early stage. In some embodiments, after a subject is identified as having an early-stage cancer through the use of any of the variety of methods provided herein, the cancer is treated via surgical resection such that the cancer is more effectively treated than if the cancer had progressed past early stage.

In some embodiments, after a subject is identified as having an early-stage cancer through the use of any of the variety of methods provided herein, the cancer is treated by administration of a therapeutic intervention such that the cancer is more effectively treated than if the cancer had progressed past early stage. In some embodiments, after a subject is identified as having an early-stage cancer through the use of any of the variety of methods provided herein, the cancer is treated by administration of a therapeutic intervention such that the subject experiences fewer or less intensive side effects than if the cancer had progressed past early stage. For example, by treating a cancer at an early stage, a lower amount or a less frequent dosing schedule of the therapeutic intervention may be administered. In some cases, a therapeutic intervention is formulated for administration in solid or liquid form including, without limitation, sterile solutions, suspensions, sustained-release formulations, tablets, capsules, pills, powders, and granules.

In some embodiments, the therapeutic intervention can result in an early onset of remission of a cancer in a subject. In some embodiments, the therapeutic intervention can result in an increase in the time of remission of a cancer in a subject. In some embodiments, the therapeutic intervention can result in an increase in the time of survival of a subject. In some embodiments, the therapeutic intervention can result in decreasing the size of a solid primary tumor in a subject. In some embodiments, the t therapeutic intervention can result in decreasing the volume of a solid primary tumor in a subject. In some embodiments, the therapeutic intervention can result in decreasing the size of a metastasis in a subject. In some embodiments, the therapeutic intervention can result in decreasing the volume of a metastasis in a subject. In some embodiments, the therapeutic intervention can result in decreasing the tumor burden in a subject.

In some embodiments, the therapeutic intervention can result in improving the prognosis of a subject. In some embodiments, the therapeutic intervention can result in decreasing the risk of developing a metastasis in a subject. In some embodiments, the therapeutic intervention can result in decreasing the risk of developing an additional metastasis in a subject. In some embodiments, the therapeutic intervention can result in decreasing cancer cell migration in a subject. In some embodiments, the therapeutic intervention can result in decreasing cancer cell invasion in a subject. In some embodiments, the therapeutic intervention can result in a decrease in the time of hospitalization of a subject. In some embodiments, the therapeutic intervention can result in a decrease of the presence of cancer stem cells within a tumor in a subject.

In some embodiments, the therapeutic intervention can result in an increase in immune cell infiltration within the tumor microenvironment in a subject. In some embodiments, the therapeutic intervention can result in altering the immune cell composition within the tumor microenvironment of a tumor in a subject. In some embodiments, the therapeutic intervention can result in modulating a previously-immunosuppressive tumor microenvironment into an immunogenic, inflammatory tumor microenvironment. In some embodiments, the therapeutic intervention can result in a reversal of the immunosuppressive tumor microenvironment in a subject.

In some embodiments, the therapeutic intervention can halt tumor progression in a subject. In some embodiments, the therapeutic intervention can delay tumor progression in a subject. In some embodiments, the therapeutic intervention can inhibit tumor progression in a subject. In some embodiments, the therapeutic intervention can inhibit immune checkpoint pathways of a tumor in a subject. In some embodiments, the therapeutic intervention can immuno-modulate the tumor microenvironment of a tumor in a subject. In some embodiments, the therapeutic intervention can immuno-modulate the tumor macroenvironment of a tumor in a subject.

In some embodiments of any of the methods described herein, the subject can be administered a single or multiple doses (e.g., two, three, four, five, six, seven, eight, nine, or ten doses) of any of the therapeutic interventions described herein.

In some embodiments of any of the methods described herein, the method can further include administering one or more therapeutic interventions. As used herein, the terms "in combination" or "combination therapy" describe any concurrent or parallel treatment with at least two distinct therapeutic agents, e.g., administration of any of at least two therapeutic interventions. In some embodiments of any of the methods described herein, the one or more therapeutic interventions are administered sequentially or simultaneously to the subject after the cancer cell has been detected. For example, the one or more therapeutic interventions can include chemotherapeutic agents, anti-angiogenic agents, apoptosis-inducing agents, surgical resection, and radiotherapy. In some embodiments, combined therapy is an epigenetic therapy (e.g., any of the epigenetic therapies described herein) and an immunotherapy (e.g., any of the immunotherapies described herein). In some embodiments, the combined therapy is 5-AZA and an immune checkpoint inhibitor (e.g., anti-PD 1 and/or anti-CTLA-4 inhibitor) (Kim (2014) PNAS 111(32): 11774-1179; Wang (2015) Cancer Immunol. Res. 3(9): 1030-1041; Juergens et al. (2011) Cancer Discov 1(7): 598-607).

Cancers

In some embodiments, methods provided herein can be used to detect cancer (e.g., a cancer cell). In some embodiments, methods provided herein can be used to detect cancer at an early stage. In some embodiments, method provided herein can be used to detect cancer when the subject has not been diagnosed with cancer and/or is not known to harbor a cancer cell. In some embodiments, methods provided herein can be used to detect the presence of a cancer cell mutation (e.g., in cell-free DNA), which cancer cell mutation is indicative that the subject harbors a cancer cell.

Cancer types that can be detected include, without limitation, lung cancer (e.g., small cell lung carcinoma or non-small cell lung carcinoma), papillary thyroid cancer, medullary thyroid cancer, differentiated thyroid cancer, recurrent thyroid cancer, refractory differentiated thyroid cancer, lung adenocarcinoma, bronchioles lung cell carcinoma, multiple endocrine neoplasia type 2A or 2B (MEN2A or MEN2B, respectively), pheochromocytoma, parathyroid hyperplasia, breast cancer, colorectal cancer (e.g., metastatic colorectal cancer), papillary renal cell carcinoma, ganglioneuromatosis of the gastroenteric mucosa, inflammatory myofibroblastic tumor, or cervical cancer, acute lymphoblastic leukemia (ALL), acute myeloid leukemia (AML), cancer in adolescents, adrenal cancer, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, colon cancer, colorectal cancer, craniopharyngioma, cutaneous T-cell lymphoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, myelogenous leukemia, myeloid leukemia, multiple myeloma, myeloproliferative neoplasms, nasal cavity and paranasal sinus cancer, nasopharyngeal cancer, neuroblastoma, non-Hodgkin's lymphoma, non-small cell lung cancer, oral cancer, oral cavity cancer, lip cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pheochromosytoma, pituitary cancer, plasma cell neoplasm, pleuropulmonary blastoma, pregnancy and breast cancer, primary central nervous system lymphoma, primary peritoneal cancer, prostate cancer, rectal cancer, renal cell cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and ureter, unknown primary carcinoma, urethral cancer, uterine cancer, uterine sarcoma, vaginal cancer, vulvar cancer, Waldenstrom Macroglobulinemia, and Wilms' tumor.

In some embodiments, methods provided herein can be used to detect the presence of a cancer and/or cancer cell from a cancer, wherein the cancer is colorectal cancer, ovarian cancer, lung cancer, or breast cancer. Various embodiments of such cancers, as therapeutic interventions appropriate to treat such cancers, are described* herein.

Colorectal Cancer

In some embodiments wherein a colorectal cancer cell has been detected in the subject, the subject may have hereditary colorectal cancer. In some embodiments, the subject has polyposis (e.g., familial adenomatous polyposis (FAP) or attenuated FAP (AFAP) (Half et al. (2009) Orphanet J Rare Dis. 4:22; Knudsen et al. (2003) Fam Cancer 2:43-55). In some embodiments, the subject has a mutation in an adenomatosis polyposis coli (APC) gene and/or a mutY DNA glycosylase (MYH) gene (Theodoratou et al. (2010) Br. J. Cancer 103: 1875-1884). In some embodiments, the subject has hereditary nonpolyposis colorectal cancer (HNPCC; also known as Lynch Syndrome) (Marra et al. (1995) J. Natl. Cancer Inst 87: 1114-1135). In some embodiments, the subject has a mutation in a DNA mismatch repair gene (e.g., mutL homolog 1 (MLH1), mutS homolog 2 (MSH2), mutS homolog 6 (MSH6) and/or PMS1 homolog 2 (PMS2)). In some embodiments, the subject has a mutation in an epithelial cell adhesion molecule (EPCAM) gene. In some embodiments, the subject has a mutation in an axin-related protein 2 (AXIN2) gene (Lammi et al. (2004) Am. J. Hum. Genet. 74: 1043-1050). In some embodiments wherein a colorectal cancer cell has been detected in the subject, the subject has oligopolyposis, juvenile polyposis syndrome, Cowden syndromw, Peutz-Jeghers syndrome (Giardiello et al. (2006) Clin. Gastroenterol. Hepatol. 4:408-415), or serrated polyposis syndrome (Torlakovic et al. (1996) Gastroenterology 110: 748-755). In some embodiments, the subject has hereditary mixed polyposis syndrome (Whitelaw et al. (1997) Gastroenterology 112: 327-334; Tomlinson et al. (1999) Gastronenterology 116: 789-795).

In some embodiments wherein a colorectal cancer cell has been detected in the subject, the subject has at least one mutation in a gene selected from the group consisting of: adenomatosis polyposis coli (APC), mutY DNA glycosylase (MYH), mutL homolog 1 (MLH1), mutS homolog 2 (MSH2), mutS homolog 6 (MSH6), PMS1 homolog 2 (PMS2), epithelial cell adhesion molecule (EPCAM), DNA polymerase epsilon (POLE), DNA polymerase delta 1 (POLD1), nth like DNA glycosylase 1 (NTHL1), bone morphogenetic protein receptor type 1A (BMPRIA), SMAD family member 4 (SMAD4), phosphatase and tensin homolog (PTEN), serine/threonine kinase 11 (LKB1, STK11), transforming growth factor beta receptor 2 (TGFβRII), phosphatidylinositol-4,5-biphosphate-3-kinase catalytic subunit alpha (PIK3CA), tumor protein p53 (TP53), epidermal growth factor receptor (EGFR), B-raf proto-oncogene (BRAF), phosphatidylinositol-4,5-biphosphate-3-kinase (PI3K), A-T rich interaction domain 1A (ARID1A), sex determining region Y-bod 9 (SOX9), erb-b2 receptor tyrosine kinase 2 (ERBB2), insulin like growth factor 2 (IGF2), APC membrane recruitment protein (FAM123B; AMER1), neuron navigator 2 (NAV2), vacuolar protein sorting 72 homolog (TCFL1; VPS72), N-Ras proto-oncogene (NRAS), and combinations thereof. See, e.g., Armaghany et al. (2012) Gastrointest. Cancer Res. 5(1): 19-27; Bulow et al. (2004) Gut 53: 381-386; Zeichner et al. (2012) Clin. Med. Insights Oncol. 6: 315-323; The Cancer Genomic Atlas Network (2012) Nature 487: 330-337; Kemp et al. (2004) Hum. Mol. Genet. 13(suppl_2: R177-R185; Zouhairi et al. (2011) Gastrointest Cancer Res 4(1): 15-21.

In some embodiments, the subject has a genetic mutation that can result in activation of a proto-oncogene (e.g., KRAS). In some embodiments, the subject has a genetic mutation that can result in inactivation of a tumor suppressor gene (e.g., 1, 2, 3, 4, 5, 6, at least 1, at least 2 or at least 3 tumor suppressor genes). In some embodiments, at least three tumor suppressor genes are inactivated (e.g., APC, TP53, and loss of heterozygosity of long arm of chromosome 18). In some embodiments, the subject has a genetic mutation in a gene involved in the APC/Wnt/β-catenin pathway. In some embodiments, the genetic mutation is a nonsense mutation or a frameshift mutation, thereby resulting in a truncated protein. In some embodiments, the genetic mutation causes microsatellite instability, epigenetic instability and/or aberrant CpG methylation.

In some embodiments wherein a colorectal cancer cell has been detected in the subject, the subject is administered a therapeutic intervention that specifically targets the genetic modifications present in the subject's colorectal cancer. In some embodiments, the subject is administered an anti- EGFR monoclonal antibody (e.g., cetuximab or panitumumab) (Cunningham et al. (2004) N. Engl. J. Med. 351(4): 337-345).

In some embodiments, the therapeutic invention is an antiangiogenic agent. In some embodiments, the antiangiogenic agent is bevacizumab (Avastin) (Hurwitz et al. (2004) N. Engl. J. Med. 350: 2335-2342). In some embodiments, the antiangiogenic agent is a VEGF inhibitor (e.g., aflibercept (Tang et al. (2008) J. Clin. Oncol 26 (May 20 suppl; abstr 4027); vatalanib (PTK/ZK222584; Hecht et al. (2005) ASCO Annual Meeting Proceedings J. Clin. Oncol. 23: 16S (abstr. LBA3)); sunitinib (Saltz et al. (2007) J. Clin. Oncol. 25: 4793-4799); AZD2171 (Rosen et al. (2007) J. Clin. Oncol. 25: 2369-76); AMG 706 (Drevis et al. (2007) 25: 3045-2054)). In some embodiments, bevacizumb is administered with a chemotherapy treatment (see, e.g., Hurwitz et al. (2004) N. Engl. J. Med. 350: 2335-2342; Gruenberger et al. (2008) J. Clin. Oncol. 26: 1830-1835). Non-limiting examples of chemotherapy treatments that can be used in a subject with colorectal cancer include: 5-FU, leucovorin, oxaliplatin (Eloxatin), capecitabine, celecoxib and sulindac. In some embodiments, a combination of chemotherapeutic agents is used, e.g., FOLFOX (5-FU, leucovorin and oxaliplatin), FOLFIRI (leucovorin, 5-FU and irinotecan (Camptosar), CapeOx (capecitabine (Xeloda) and oxaliplatin). In some embodiments, the therapeutic intervention is a mammalian target of rapamycin (mTOR) inhibitor (e.g., a rapamycin analog (Kesmodel et al. (2007) Gastrointestinal Cancers Symposium (abstr 234)); RAD-001 (Tabernero et al. (2008) J. Clin. Oncol. 26: 1603-1610). In some embodiments, the therapeutic intervention is a protein kinase C antagonist (e.g., enzastaurin (Camidge et al. (2008) Anti-cancer Drugs 19:77-84, Resta et al. (2008) J. Clin. Oncol. 26 (May 20 suppl) (abstr 3529)). In some embodiments, the therapeutic intervention is an inhibitor of nonreceptor tyrosine kinase Src (e.g., AZ0530 (Tabernero et al. (2007) J. Clin. Oncol. 25: 18S (abstr 3520))). In some embodiments, the therapeutic intervention is an inhibitor of kinesin spindle protein (KSP) (e.g., ispinesib (SB-715992) (Chu et al. (2004) J. Clin. Oncol. 22:14S (abstr 2078), Burris et al. (2004) J. Clin. Oncol. 22: 128 (abstr 2004))).

In some embodiments, the therapeutic intervention is surgery (e.g., polypectomy, partial colectomy, colectomy or diverting colostomy). In some embodiments, adjuvant chemotherapy is further administered to the subject after surgery (e.g., polypectomy or partial colectomy). In some embodiments, the therapeutic intervention is a prophylactic surgery (e.g., colectomy). In some embodiments, a cancer may be removed by ablation or embolization.

Ovarian Cancer

In some embodiments wherein an ovarian cancer cell has been detected in the subject, the subject may have hereditary ovarian cancer (Petrucelli et al. (2010) Gen. Med 12:245-259). In some embodiments, the subject has another genetic condition that may cause ovarian cancer (e.g., Lynch syndrome, Peutz-Jeghers syndrome, nevoid basal cell carcinoma syndrome (NBCCS; also known as Gorlin syndrome), Li-Fraumeni syndrome or Ataxia-Telangiecstasia (Cancer.Net). In some embodiments, the subject may have an invasive epithelial ovarian cancer, an epithelial tumor of low malignant potential (also known as an atypical proliferating tumor or a borderline tumor), a germ cell tumor of the ovary (e.g. a malignant germ cell tumor, a dysgerminoma, an immature teratoma) or a stromal tumor of the ovary.

In some embodiments, the subject's ovarian cancer was caused by a somatic mutation in a gene. In some embodiments, the subject has a mutation in a gene selected from the group consisting of: tumor protein p53 (TP53), breast cancer 1 (BRCA1), breast cancer 2 (BRCA2), mutL homolog 1 (MLH1), mutS homolog 2 (MSH2), AKT serine/threonine kinase 1 (AKT1), BRAC1 associated ring domain 1 (BARD1), BRAC1 interacting protein C-terminal helicase 1 (BRIP1), epithelial cadherin 1 (CDH1), checkpoint kinase 2 (CHEK2), catenin beta 1 (CTNNB1), MRE11 homolog (MRE11), mutS homolog 6 (MSH6), nibrin (NBN), opiod binding protein/cell adhesion molecule like (OPCML), partner and localizer of BRCA2 (PALB2), phosphatidylinositol-4,5-biphosphate-3-kinase catalytic subunit alpha (PIK3CA), PMS1 homolog 2 (PMS2), parkin RBR E3 ubiquitin protein ligase (PRKN), RAD50 double strand break repair protein (RAD50), RAD51 recombinase (RAD51), serine/threonine kinase 11 (LKB1, STK11), neurofibromin (NF1), retinoblastoma 1 (RB1), cyclin dependent kinase 12 (CDK12), and combinations thereof. See, e.g., Kurman et al. (2011) Hum. Pathol. 42(7): 918-31; Nakayama et al. (2006) Cancer Biol. Ther. 5(7): 779-785; Singer et al. (2003) J. Natl Cancer Inst 95(6): 484-6; Kuo et al. (2009) Am. J. Pathol. 174(5): 1597-601; Gemignani et al. (2003) Gynecol. Oncol. 90(2): 378-81; Levine et al. (2005) Clin. Cancer Res. 11(8): 2875-8; Wang et al. (2005) Hum. Mutat. 25(3): 322; Landen et al. (2008) J. Clin. Oncol. 26(6): 995-1005; Ramus et al. (2015) j Natl Cancer Inst 107(11).

In some embodiments the therapeutic intervention is chemotherapy (e.g., any of the platinum-based chemotherapeutic agents described herein (e.g., cisplatin, carboplatin), or a taxane (e.g., placitaxel (Taxol®) or docetaxel (Taxotere®). In some embodiments, the chemotherapeutic agent is an albumin-bound paclitaxel (nap-paclitaxel, Abraxane®), altretamine (Hexalen®), capecitabine (Xeloda®), cyclophosphamide (Cytoxan®), etoposide(VP-16), gemcitabine (Gemzar®), ifosfamide (Ifex®), irinotecan (CPT-11, Camptosar®), liposomal doxorubicin (Doxil®), melphalan, pemetrexed (Alimta®), topotecan, or vinorelbine (Navelbine®). In some embodiments, the therapeutic intervention is a combination of chemotherapeutic agents (e.g., paclitaxel, ifosfamide, and cisplatin; vinblastine, ifosfamide and cisplatin; etoposide, ifosfamide and cisplatin).

In some embodiments, the therapeutic intervention is an epigenetic therapy (see, e.g., Smith et al. (2017) Gynecol. Oncol. Rep. 20: 81-86). In some embodiments, the epigenetic therapy is a DNA methyltransferase (DNMT) inhibitor (e.g., 5-azacytidine (5-AZA), decitabine (5-aza-2'-deoxycytidine) (Fu et al. (2011) Cancer 117(8): 1661-1669; Falchook et al. (2013) Investig. New Drugs 31(5): 1192-1200; Matei et al. (2012) Cancer Res. 72(9): 2197-2205). In some embodiments, the DNMT1 inhibitor is NY-ESO-1 (Odunsi et al. (2014) Cancer Immunol. Res. 2(1): 37-49). In some embodiments, the epigenetic therapy is a histone deacetylase (HDAC) inhibitor. In some embodiments, the HDAC inhibitor is vorinostat (Modesitt (2008) 109(2): 182-186) or belinostat (Mackay et al. (2010) Eur. J. Cancer 46(9): 1573-1579). In some embodiments, the HDAC inhibitor is given in combination with a chemotherapeutic agent (e.g., carboplatin (paraplatin), cisplatin, paclitaxel or docetaxel (taxotere)) (Mendivil (2013) Int. J. Gynecol. Cancer 23(3): 533-539; Dizon (2012) Gynecol. Oncol. 125(2): 367-371; Dizon (2012) Int J. Gynecol. Cancer 23(3): 533-539).

In some embodiments, the therapeutic intervention is an anti-angiogenic agent (e.g., bevacizumab).

In some embodiments, the therapeutic intervention is a poly (ADP-ribose) polymerase (PARP)-1 and/or PARP-2 inhibitor. In some embodiments, the PARP-1 and PARP-2 inhibitor is niraparib (zejula) (Scott (2017) Drugs doiL 10.1007/s40265-017-0752). In some embodiments, the PARP inhibitor is olaparib (lynparza) or rucaparib (rubraca).

In some embodiments, the therapeutic intervention is a hormone (e.g., a luteinizing-hormone-releasing hormone (LHRH) agonist). In some embodiments, the LHRH agonist is goserelin (Zoladex®) or leuprolide (Lupron®). In some embodiments, the therapeutic intervention is an anti-estrogen compound (e.g., tamoxifen). In some embodiments, the therapeutic intervention is an aromatase inhibitor (e.g., letrozole (Femara®), anastrozole (Arimidex®) or exemestane (Aromasin®).

In some embodiments, the therapeutic intervention is surgery (e.g., debulking of the tumor mass, a hysterectomy, a bilateral salpingo-oophorectomy, an omentectomy). The term "debulking" refers to surgical removal of almost the entire tumor ("optimally debulked"). In some embodiments, debulking can include removing a portion of the bladder, the spleen, the gallbladder, the stomach, the liver, and/or pancreas. In some embodiments, adjuvant chemotherapy is further administered to the subject after surgery (e.g., debulking of the tumor mass, a hysterectomy, a bilateral salpingo-oophorectomy, an omentectomy). In some embodiments, adjuvant chemotherapy is administered intra-abdominally (intraperitoneally). In some embodiments, the therapeutic intervention is a prophylactic surgery (e.g., a hysterectomy). In some embodiments, a paracentesis is performed to remove ascites.

In some embodiments, the therapeutic intervention is radiation therapy. In some embodiments, the radiation therapy is external beam radiation therapy, brachytherapy or a use of radioactive phosphorus.

Lung Cancer

In some embodiments wherein a lung cancer cell has been detected in the subject, the subject may have hereditary lung cancer (Gazdar et al. (2014) J. Thorac. Oncol. 9(4): 456-63). In some embodiments, the subject has non-small cell-lung cancer (NSCLC) or small cell lung cancer (SCLC).

In some embodiments, the subject's lung cancer was caused by a somatic mutation in a gene. In some embodiments, the subject has a mutation in a gene selected from the group consisting of: ARID1A, AKT, anaplastic lymphoma kinase (ALK), BRAF, cyclin dependent kinase inhibitor 2 (CDKN2A), discoidin domain receptor tyrosine kinase 2 (DDR2), epidermal growth factor receptor (EGFR), fibroblast growth factor receptor 1 (FGFR1), HER2/ERBB2, kelch like ECH associated protein 1 (KEAP1) (Singh et al. (2006) PLoS Med 3: e420), KRAS proto-oncogene (KRAS), MAP kinase/ERK kinase 1 (MEK1), MET proto-oncogene (MET), MAX gene associated (MGA), myelocytomatosis oncogene (MYC), NF1, NRAS, neutrophophic receptor tyrosine kinase 1 (NTRK1), PTEN, PIK3CA, RB1, RNA binding motif protein 10 (RBM10), ret proto-oncogene (RET), Ras like without CAAX 1 (RIT1) (Berger et al. (2014) Oncogene), Ros proto-oncogene (ROS1), STE domain containing 2 (SETD2), SWI/SNF related matrix associated actin dependent regulator of chromatin, subfamily A, member 4 (SMARCA4) (Medina et al. (2008) Hum. Mutat. 29: 617-622), (SOX2) (Rudin et al. (2012) Nature Genet. 44: 1111-1116), LKB1 (STK11) (Sanchez-Cespedees et al. (2002) Cancer Res. 62: 3659-3662), TP53 (Takahashi et al. (1989) Science 246: 491-494), U2 small nuclear RNA auxillary factor 1 (U2AF1), and combinations thereof. See e.g., The Cancer Genome Atlas Research Network (2014) Nature 511: 543-550; Ding et al. (2008) Nature 1069-1075; The Cancer Genome Atlas Research Network (2012) Nature 489: 519-525; Seo et al. (2012) Genome Res. 22: 2109-2119; El-Telbany and Ma (2012) Genes Cancer 3(7-8): 467-480; Marks et al. (2008) Cancer Res. 68: 5524-5528; De Braud et al. (2014) J. Clin. Oncol. 32: 2502; Rothschild (2015) Cancers 7: 930949.

In some embodiments, a copy number variation or an oncogenic chromosomal gene rearrangement (e.g., oncogenic chromosomal translocation) is detected in a lung cancer cell. Non-limiting examples of oncogenic chromosomal translocation found in lung cancer include: EML4-ALK, TFG-ALK, KIF5B-ALK, KLC1-ALK, PTPN3-ALK, TPR-ALK, HIP1-ALK, STRN-ALK, DCTN1-ALK, SQSTM1-ALK, BIRC6-ALK, RET-PTC1, KIF4B-RET, CCDC6-RET and NCOA4-RET. See, e.g., Iyevleva et al. (2015) Cancer Lett. 362(1): 116-121; Wang et al. (2012) J. Clin Oncol. 30: 4352-9

In some embodiments, the therapeutic intervention is an anti-angiogenic agent (e.g., bevacizumab (avastin), ramucirumab (cyramza)).

In some embodiments, the therapeutic intervention is a targeted drug therapy. In some embodiments, the targeted drug therapy is an EGFR inhibitor (e.g., erlotinib (tarceva), afatinib (gilotrif), gefitinib (iressa), necitumumab (portrazza), cetuximab, osimertinib (AZD9291, Tagrisso), rociletinib (CO-1686), HM61713 (BI 1482694), ASP8273, EGF816, PF-06747775). See, e.g., Wang et al. (2016) J. Hematol Oncol 9:34; Cross et al. (2014) Cancer Discov. 4(9): 1046-61; Walter et al. (2013) Cancer Discov 3(12): 1404-15; Park et al. (2015) ASCO Meeting Abstract 33(15): 8084; Sequist et al. (2015) 372(18): 1700-9; Lee et al. (2014) Cancer Res 74(19Supplement):LB-100; Sakagami et al. (2014) Cancer Res 74(19 Supplement): 1728; Goto et al. (2015) ASCO Meeting Abstract 33(15_Suppl):8014; Jia et al. (2016) Cancer Res 76: 1591-602.

In some embodiments, the targeted drug therapy is an ALK inhibitor (e.g., crizotinib (xalkori), ceritinib (zykadia, LDK378), alectinib (alecensa, RO5424802; CH5424802), brigatinib (alunbrig, AP26113), lorlatinib (PF-06463922), TSR-011, RXDX-101 (NMS-E628), X-396, CEP-37440). See, e.g., Tartarone et al. (2017) Med. Oncol. 34(6): 110; Galkin et al. (2007) PNAS 104(1): 270-275; Friboulet et al. (2014) Cancer Discov. 4(6): 662-73; Chen et al. (2013) 56(14): 5673-5674; Shaw et al. (2014) N. Engl. J. Med. 370(13): 1189-1197; Sakamoto et al. (2011) Cancer Cell 19(5): 679-690; Squillace et al. (2013) Cancer Res. 73(8_suppl_: 5655; Mori et al. (2014) 13(2): 329-340; Patnaik et al. (2013) J. Clin. Oncol. 31 (15 suppl); Weiss et al. (2013) J Thorac Oncol. 8(suppl2): S618; Ardini et al. (2009) Mol. Cancer Ther. 8(12suppl): A244; Horn et al. (2014) J. Clin. Oncol. 32(15suppl); Cheng et al. (2012) Mol. Cancer Ther. 11(3): 670-679; Zhang et al. (2011) Cancer Res. 70(8suppl): LB-298; Awad and Shaw (2014) Clin. Adv. Hematol. Oncol. 12(7): 429-439.

In some embodiments, the targeted drug therapy is a heat shock protein 90 inhibitor (e.g, AUY922, ganetspib, AT13387). See, e.g., Pillai et al. (2014) Curr Opin Oncol. 26(2): 159-164; Normant et al. (2011) Oncogene 30(22): 2581-2586; Sequist et al. (2010) J. Clin. Oncol. 28(33): 4953-4960; Sang et al. (2013) Cancer Discov. 3(4): 430-443; Felip et al. (2012) Ann Oncol 23(suppl9); Miyajima et al. (2013) Cancer Res. 73(23): 7022-7033.

In some embodiments, the targeted drug therapy is a RET inhibitor (e.g., cabozantinib (XL184), vandetanib, alectinib, sorafenib, sunitinib, ponatinib) See, e.g., Drilon et al. (2013) Cancer Discov 3:6305; Gautschi et al. (2013) J. Thorac Oncol 8: e43-4; Kodama et al. (2014) Mol. Cancer Ther. 13: 2910-8; Lin et al. (2016) J. Thoracic Oncol. 11(11): 2027-2032; Rosell and Karachaliou (2016) Lancet 17(12): 1623-1625; Falchook et al. (2016) J. Clin Oncol. 34(15): e141-

144; Shaw et al. (2013) Nat Rev Cancer 13: 772-787; Gozgit et al. (2013) Cancer Res 73 (Suppl. 1): 2084.

In some embodiments, the targeted drug therapy is a BRAF inhibitor (e.g., dabrafenib, vemurafenib). See, e.g., Planchard et al. (2013) J. Clin. Oncol. 31:8009; Gautschi et al. (2013) Lung Cancer 82: 365-367; Schmid et al. (2015) Lung Cancer 87: 85-87.

In some embodiments, the targeted drug therapy is a MET inhibitor (e.g., onartuzumab, ficlatuzumab, rilotumumab, tivantinib, crizotinib). See, e.g., Spigel et al. (2014) J. Clin. Oncol. 32: 8000; Patnail et al. (2014) Br. J. Cancer 111: 272-280; Gordon et al. (2010): Clin. Cancer Res. 16: 699-710; Sequist et al. (2011) J. Clin. Oncol. 29: 3307-3315; Zou et al. (2007) Cancer Res. 67: 4408-4417; Ou et al. (2011) J. Thorac. Oncol. 6: 942-946.

In some embodiments, the therapeutic intervention is administration of an immunotherapy. See, e.g., Smasundaram and Burns (2017) J. Hematol. Oncol. 10:87. In some embodiments, the immunotherapy is an anti-PD-1 agent (e.g., nivolumab) (Brahmer et al. (2012) N. Engl. J. Med. 366(26): 2455-2465; Gettinger et al. (2016) J. Clin. Oncol. 34(25)), pembrolizumab (Keytruda) (Garon et al. (2015) N. Engl. J. Med. 372(21): 2018-2028), durvalumab), nivolumab (opdivo)). In some embodiments, the immunotherapy is an anti-PD-L1 agent (e.g., atezolizumab (Fehrenbacher et al. (2016) Lancet 387(10030): 1837-1846, Rittmeyer et al. (2017) Lancet 389(10066): 255-265); atezolizumab (Tecentriq)). In some embodiments, the immunotherapy is an anti-CTLA-4 agent (e.g., ipilimumab or tremlimumab). In some embodiments, the immunotherapy is a combination therapy of an anti-PD-1 agent and an anti-CTLA-4 agent (e.g., nivolumab and ipilimumab (Herbset et al. (2015) 21(7): 1514-1524), pembrolizumab and ipilimumab (Gubens et al. (2016) ASCO Meeting Abstracts 34(15_suppl):9027), durvalumab and tremlimumab (NCT02542293. Study of 1st line therapy study of MEDI4736 with tremelimumab versus SoC in non-small-cell lung cancer (NSCLC) (NEPTUNE)).

In some embodiments, the immunotherapy is given in combination with a chemotherapeutic agent (e.g., Rizvi et al. (2016) J. Clin. Oncol. 34(25): 2969-79; Hall et al. (2016) ASCO Meeting Abstracts. 34(15_suppl):TPS9104).

In some embodiments, the therapeutic intervention is chemotherapy (e.g., cisplatin, carboplatin, paclitaxel, albumin-bound paclitaxel, docetaxel, gemcitabine, vinorelbine, irinotecan, etoposide, vinblastine or pemetrexed (alimta)). In some embodiments, the therapeutic intervention is a combination of at least two chemotherapeutic agents.

In some embodiments, the therapeutic intervention is surgery (e.g., a wedge resection (i.e. removal of a small section of diseased lung and a margin of healthy tissue); a segmental resection (segmentectomy) (i.e. removal of a larger portion of lung, but not an entire lobe); a lobectomy (i.e. removal of an entire lobe of one lung); a pneumonectomy (i.e. removal of an entire lung)), or a sleeve resection. The extent of surgical removal will depend on the stage of lung cancer and overall prognosis. In some embodiments, surgery is carried out by video-assisted thoracic surgery (VATS). In some embodiments, the therapeutic intervention is radiofrequency ablation (RFA).

In some embodiments, the therapeutic intervention is radiation therapy. In some embodiments, the radiation therapy is external beam radiation therapy (e.g., three-dimensional conformal radiation therapy (3D-CRT), intensity modulated radiation therapy (IMRT), stereotactic body radiation therapy (SBRT), brachytherapy or a use of radioactive phosphorus.

In some embodiments, the therapeutic intervention further comprises palliative care. In some embodiments, palliative care includes removal of pleural effusion by thoracentesis, pleurodesis or catheter placement. In some embodiments, palliative care includes removal of pericardial effusion by pericardiocentesis, a pericardial window. In some embodiments, the therapeutic intervention is photodynamic therapy (PDT), laser therapy or stent placement.

Breast Cancer

In some embodiments wherein an ovarian cancer cell has been detected in the subject, the subject may have hereditary breast cancer (Peters et al. (2017) Gynecol Oncol pii: S0090-8258(17)30794-1). In some embodiments, the subject may have triple negative breast cancer (estrogen receptor negative, progesterone receptor negative and HE2-negative), hormone receptor positive (estrogen and/or progesterone receptor positive) breast cancer, hormone receptor negative (estrogen and/or progesterone receptor negative) breast cancer, HER2 positive breast cancer, HER2 negative breast cancer, inflammatory breast cancer or metastatic breast cancer.

In some embodiments wherein a breast cancer cell has been detected in the subject, the subject has at least one mutation in a gene selected from the group consisting of: BRCA1, BRCA2, ATM, CHD1, CHEK2, PALB2, STK11, TP53, HER2 (ERBB2), CDK4/6, AKT1, GATA binding protein 3 (GATA3), RB1, lysine methyltransferase 2C (MLL3), mitogen-activated protein kinase 1 (MAP3K1), CDKN1B, T-box3(TBX3), runt related transcription factor 1 (RUNX1), core binding factor beta (CBFB), phosphoinositide-3-kinase regulatory subunit 1 (PIK3R1), protein tyrosine phosphatase non-receptor type 22 (PTPN22), protein tyrosine phosphatase receptor type D (PTPRD), NF1, splicing factor 3b subunit 1 (SF3B1), cyclin D3 (CCND3), T-box 5 (TBX5), CCCTC-binding factor (CTCF), forkhead box A1 (FOXA1), PI3KCA, PTEN, mitogen-activated protein kinase 4 (MAP2K4), and combinations thereof. See, e.g., Nik-Zainal et al. (2016) Nature 534: 47-54; Bergamaschi et al. (2008) J. Pathol. 214: 357-367; Pleasance et al. (2010) Nature 463: 191-196; The Cancer Genome Atlas Network (2012) Nature 490:61-70; Usary et al. (2004) Oncogene 23: 7669-7678; Bachman et al. (2004) Cancer Biol. Ther. 3: 772-775; Saal et al. (2008) Nature Genet 40: 102-107; Troester et al. (2006) BMC Cancer 6: 276; Chandriani et al. (2009) PLoS One 4: e6693; Matsuda et al. (2017) Breast Cancer Res Treat 163(2): 263-272.

In some embodiments, the targeted drug therapy is a HER2 inhibitor (e.g., trastuzumab (Herceptin), pertuzumab (perjeta); ado-trastuzumab emtansine (T-DM1; Kadcyla); lapatinib (Tykerb), neratinib). See, e.g., Baselga et al. (2012) N Engl J Med 366: 109-119; Konecny et al. (2006) Cancer Res 66: 1630-1639, Xia et al. (2007) Cancer Res. 67: 1170-1175; Gomez et al. (2008) J Clin Oncol 26: 2999-30005; Wong et al. (2009) Clin. Cancer Res. 15: 2552-2558; Agus et al. (2002) Cancer Cell 2: 127-137; Lewis Philips et al. (2008) Cancer Res 68: 9280-9290.

In some embodiments, the targeted drug therapy is a cyclin-dependent kinase inhibitor (e.g., a CDK4/6 inhibitor (e.g., palbociclib (Ibrance®), ribociclin(Kisqali®), abemaciclib) (Turner et al. (2015) N Engl J Med 373: 209-219; Finn et al. (2016) N Eng J Med 375: 1925-1936; Ehab and Elbaz (2016) Breast Cancer 8: 83-91; Xu et al. (2017) J Hematol. Oncol. 10(1): 97; Corona et al. (2017) Cri Rev Oncol Hematol 112: 208-214; Barroso-Sousa et al. (2016) Breast Care 11(3): 167-173)).

In some embodiments, the targeted drug therapy is a PARP inhibitor (e.g., olaparib (AZD2281), veliparib (ABT- 888), niraparib (MK-4827), talazoparib (BMN-673), rucaparib (AG-14699), CEP-9722) See, e.g., Audeh et al. (2010) Lancet 376: 245-251; Fong et al. (2009) N Engl J Med 361: 123-134; Livrahi and Garber (2015) BMC Medicine 13: 188; Kaufamn et al. (2015) J Clin. Oncol. 33: 244-250; Gelmon et al. (2011) Lancet Oncol. 12: 852-61; Isakoff et al. (2011) Cancer Res 71:P3-16-05; Sandhu et al. (2013) Lancet Oncol 14:882-92; Tutt et al. (2010) Lancet 376: 235-44; Somlo et al. (2013) J. Clin. Oncol. 31: 1024; Shen et al. (2013) CLin. Cancer Res. 19(18): 5003-15; Awada et al. (2016) Anticancer Drugs 27(4): 342-8.

In some embodiments, the targeted drug therapy is a mTOR inhibitor (e.g., everolimus (afinitor)). See, e.g., Gong et al. (2017) Oncotarget doi: 10.18632/oncotarget.16336; Louseberg et al. (2017) Breast Cancer 10: 239-252; Hare and Harvey (2017) Am J Cancer Res 7(3): 383-404.

In some embodiments, the targeted drug therapy is a heat shock protein 90 inhibitor (e.g., tanespimycin) (Modi et al. (2008) J. Clin Oncol. 26: s1027; Miller et al. (2007) J. Clin. Oncol. 25:s1115; Schulz et al. (2012) J Exp Med 209(2): 275-89).

In some embodiments, the targeted drug therapy further includes a bone-modifying drug (e.g., a bisphosphonate or denosumab (Xgeva)). See, e.g., Ethier et al. (2017) Curr Oncol Rep 19(3): 15; Abdel-Rahman (2016) Expert Rev Anticancer Ther 16(8): 885-91.

In some embodiments, the therapeutic intervention is a hormone (e.g., a luteinizing-hormone-releasing hormone (LHRH) agonist). In some embodiments, the LHRH agonist is goserelin (Zoladex®) or leuprolide (Lupron®). In some embodiments, the therapeutic intervention is an anti-estrogen compound (e.g., tamoxifen, fulvestrant (faslodex)). In some embodiments, the therapeutic intervention is an aromatase inhibitor (e.g., letrozole (Femara®), anastrozole (Arimidex®) or exemestane (Aromasin®).

In some embodiments, the therapeutic intervention is surgery (e.g., a lumpectomy, a single mastectomy, a double mastectomy, a total mastectomy, a modified radical mastectomy, a sentinel lymph node biopsy, an axillary lymph node dissection; breast-conserving surgery). The extent of surgical removal will depend on the stage of breast cancer and overall prognosis.

In some embodiments, the therapeutic intervention is radiation therapy. In some embodiments, the radiation therapy is partial breast irradiation or intensity-modulated radiation therapy.

In some embodiments, the therapeutic intervention is chemotherapy (e.g., capecitabine (xeloda), carboplatin (paraplatin), cisplatin (platinol), cyclophosphamide (neosar), docetaxel (docefrez, taxotere), doxorubicin (Adriamycin), pegylated liposomal doxorubicin (doxil), epirubicin (ellence), fluorouracil (5-FU, adrucil), gemcitabine (gemzar), methotrexate, paclitaxel (taxol), protein-bound paclitaxel (abraxane), vinorelbine (navelbine), eribulin (halaven), or ixabepilone (ixempra)). In some embodiments, the therapeutic intervention is a combination of at least two chemotherapeutic agents (e.g., doxorubicin and cyclophosphamide (AC); epirubicin and cyclophosphamide (EC); cyclophosphamide, doxorubicin and 5-FU (CAF); cyclophosphamide, epirubicin and 5-FU (CEF); cyclophosphamide, methotrexate and 5-FU (CMF); epirubicin and cyclophosphamide (EC); docetaxel, doxorubicin and cyclophosphamide (TAC); docetaxel and cyclophosphamide (TC).

REFERENCES (IDENTIFIED BY NUMBERS WITHIN PARENTHESES THROUGHOUT THE SPECIFICATION)

1. L. A. Torre et al., Global cancer statistics, 2012. *CA Cancer J Clin* 65, 87 (March, 2015).
2. W. H. Organization, Guide to Cancer Early Diagnosis. *Guide to Cancer Early Diagnosis*, (2017).
3. R. Mazzucchelli, P. Colanzi, R. Pomante, G. Muzzonigro, R. Montironi, Prostate tissue and serum markers. *Advances in clinical pathology: the official journal of Adriatic Society of Pathology* 4, 111 (July, 2000).
4. A. Ruibal Morell, CEA serum levels in non-neoplastic disease. *The International journal of biological markers* 7, 160 (July-September, 1992).
5. C. Galli, D. Basso, M. Plebani, CA 19-9: handle with care. *Clinical chemistry and laboratory medicine* 51, 1369 (July, 2013).
6. K. A. Sikaris, CA125—a test with a change of heart. *Heart, lung & circulation* 20, 634 (October, 2011).
7. H. J. Wanebo et al., Preoperative carcinoembryonic antigen level as a prognostic indicator in colorectal cancer. *N Engl J Med* 299, 448 (Aug. 31, 1978).
8. J. S. Lin et al., in *Screening for Colorectal Cancer. A Systematic Review for the U.S. Preventive Services Task Force*. (Rockville (Md.), 2016).
9. A. G. Zauber, The impact of screening on colorectal cancer mortality and incidence: has it really made a difference? *Dig Dis Sci* 60, 681 (March, 2015).
10. P. Mandel, P. Metais. *Comptes rendus des seances de la Societe de biologie et de ses filiales* 142, 241 (February, 1948).
11. M. Stroun, P. Anker, J. Lyautey, C. Lederrey, P. A. Maurice, Isolation and characterization of DNA from the plasma of cancer patients. *European journal of cancer & clinical oncology* 23, 707 (June, 1987).
12. S. A. Leon, B. Shapiro, D. M. Sklaroff, M. J. Yaros, Free DNA in the serum of cancer patients and the effect of therapy. *Cancer Res* 37, 646 (March, 1977).
13. C. Bettegowda et al., Detection of circulating tumor DNA in early- and late-stage human malignancies. *Sci Transl Med* 6, 224ra24 (Feb. 19, 2014).
14. R. J. Leary et al., Detection of chromosomal alterations in the circulation of cancer patients with whole-genome sequencing. *Sci Transl Med* 4, 162ra154 (Nov. 28, 2012).
15. M. Sausen et al., Clinical implications of genomic alterations in the tumour and circulation of pancreatic cancer patients. *Nat Commun* 6, 7686 (2015).
16. S. J. Dawson et al., Analysis of circulating tumor DNA to monitor metastatic breast cancer. *N Engl J Med* 368, 1199 (Mar. 28, 2013).
17. T. Forshew et al., Noninvasive identification and monitoring of cancer mutations by targeted deep sequencing of plasma DNA. *Sci Transl Med* 4, 136ra68 (May 30, 2012).
18. M. Murtaza et al., Non-invasive analysis of acquired resistance to cancer therapy by sequencing of plasma DNA. *Nature* 497, 108 (May 2, 2013).
19. A. M. Newman et al., An ultrasensitive method for quantitating circulating tumor DNA with broad patient coverage. *Nat Med* 20, 548 (May, 2014).
20. S. T. Kim et al., Prospective blinded study of somatic mutation detection in cell-free DNA utilizing a targeted 54-gene next generation sequencing panel in metastatic solid tumor patients. *Oncotarget* 6, 40360 (Nov. 24, 2015).

21. A. M. Newman et al., Integrated digital error suppression for improved detection of circulating tumor DNA. *Nat Biotechnol* 34, 547 (May, 2016).
22. S. Jones et al., Personalized genomic analyses for cancer mutation discovery and interpretation. *Sci Transl Med* 7, 283ra53 (Apr. 15, 2015).
23. S. A. Forbes et al., COSMIC (the Catalogue of Somatic Mutations in Cancer): a resource to investigate acquired mutations in human cancer. *Nucleic Acids Res* 38, D652 (January, 2010).
24. M. Xie et al., Age-related mutations associated with clonal hematopoietic expansion and malignancies. *Nat Med* 20, 1472 (December, 2014).
25. T. McKerrell et al., Leukemia-associated somatic mutations drive distinct patterns of age-related clonal hemopoiesis. *Cell Rep* 10, 1239 (Mar. 3, 2015).
26. G. Genovese et al., Clonal hematopoiesis and blood-cancer risk inferred from blood DNA sequence. *N Engl J Med* 371, 2477 (Dec. 25, 2014).
27. T. Sjoblom et al., The consensus coding sequences of human breast and colorectal cancers. *Science* 314, 268 (Oct. 13, 2006).
28. C. H. Wilson, R. E. McIntyre, M. J. Arends, D. J. Adams, The activating mutation R201C in GNAS promotes intestinal tumourigenesis in Apc(Min/+) mice through activation of Wnt and ERK1/2 MAPK pathways. *Oncogene* 29, 4567 (Aug. 12, 2010).
29. G. Y. Locker et al., ASCO 2006 update of recommendations for the use of tumor markers in gastrointestinal cancer. *J Clin Oncol* 24, 5313 (Nov. 20, 2006).
30. D. A. Haber, V. E. Velculescu, Blood-based analyses of cancer: circulating tumor cells and circulating tumor DNA. *Cancer discovery* 4, 650 (June, 2014).
31. M. W. Snyder, M. Kircher, A. J. Hill, R. M. Daza, J. Shendure, Cell-free DNA Comprises an In Vivo Nucleosome Footprint that Informs Its Tissues-Of-Origin. *Cell* 164, 57 (Jan. 14, 2016).
32. E. Toes-Zoutendijk et al., Real-Time Monitoring of Results During First Year of Dutch Colorectal Cancer Screening Program and Optimization by Altering Fecal Immunochemical Test Cut-Off Levels. *Gastroenterology* 152, 767 (March, 2017).
33. S. Fisher et al., A scalable, fully automated process for construction of sequence-ready human exome targeted capture libraries. *Genome Biol* 12, R1 (2011).
34. M. Sausen et al., Integrated genomic analyses identify ARID1A and ARID1B alterations in the childhood cancer neuroblastoma. *Nat Genet* 45, 12 (January, 2013).

The invention will be further described in the following examples, which do not limit the scope of the invention described in the claims.

EXAMPLES

Example 1—Targeted Error Correction Sequencing

A methodology for comprehensive analysis of sequence alterations in driver genes that are commonly mutated in colorectal, lung, ovarian, breast and other cancers was developed. Similar to targeted analyses of cancer tissues (22), genes were first selected that were broadly mutated in these tumors, and analyses were focused on either the entire coding regions or the most highly mutated exons of these genes. An analysis of the frequency of these alterations in databases of somatic mutations in cancer (e.g. COSMIC) (23) revealed that over three quarters of patients would be expected to have at least one mutation in 55 genes among the intended cancers as well as other common tumor types (Table 1, Table S1). It was hypothesized that a larger panel of genes would increase the probability of detecting at least one gene alteration in the plasma from a cancer patient. Because alterations in the blood have previously been reported in healthy individuals (24-26), characteristic sequence positions in three cancer related genes in the 55 gene panel as well as three additional genes (Table S1) that were known to be somatically altered in clonal hematopoietic expansion, myelodysplasia or other hematological malignancies were also examined.

TABLE 1

Cancer cases containing alterations in driver genes

| Tissue Type | Cases in COSMIC | Detectable Cases* | Detectable Fraction |
|---|---|---|---|
| Breast | 1,002 | 719 | 72% |
| Colorectal | 1,248 | 1,071 | 86% |
| Lung | 1,198 | 932 | 78% |
| Ovarian | 647 | 524 | 81% |

*Detectable cases indicate those with at least one alteration from the cancer driver genes analyzed (Table S1).

A custom capture and sequencing approach called targeted error correction sequencing (TEC-Seq) was developed to allow sensitive and specific detection of low abundance sequence alterations using next generation sequencing (FIG. 1). This methodology is based on targeted capture of multiple regions of the genome and deep sequencing (~30,000×) of DNA fragments. The 58 genes analyzed in this study comprised 80,930 captured bases. Specific steps were performed for analysis of rare DNA molecules and for elimination of potential amplification, sequencing, and contamination errors. These included (1) optimized library generation and capture for conversion of cell-free DNA for subsequent analyses, (2) maximizing representation of unique cell-free DNA molecules analyzed, (3) redundant sequencing, where multiple identical DNA molecules are generated and sequenced, (4) removal of mapping and sequencing artifacts, (5) unique identification of individual patient libraries, and (6) identification of tumor-specific alterations in established cancer genes (see Example 6—Materials and Methods for additional details).

Figure 7:
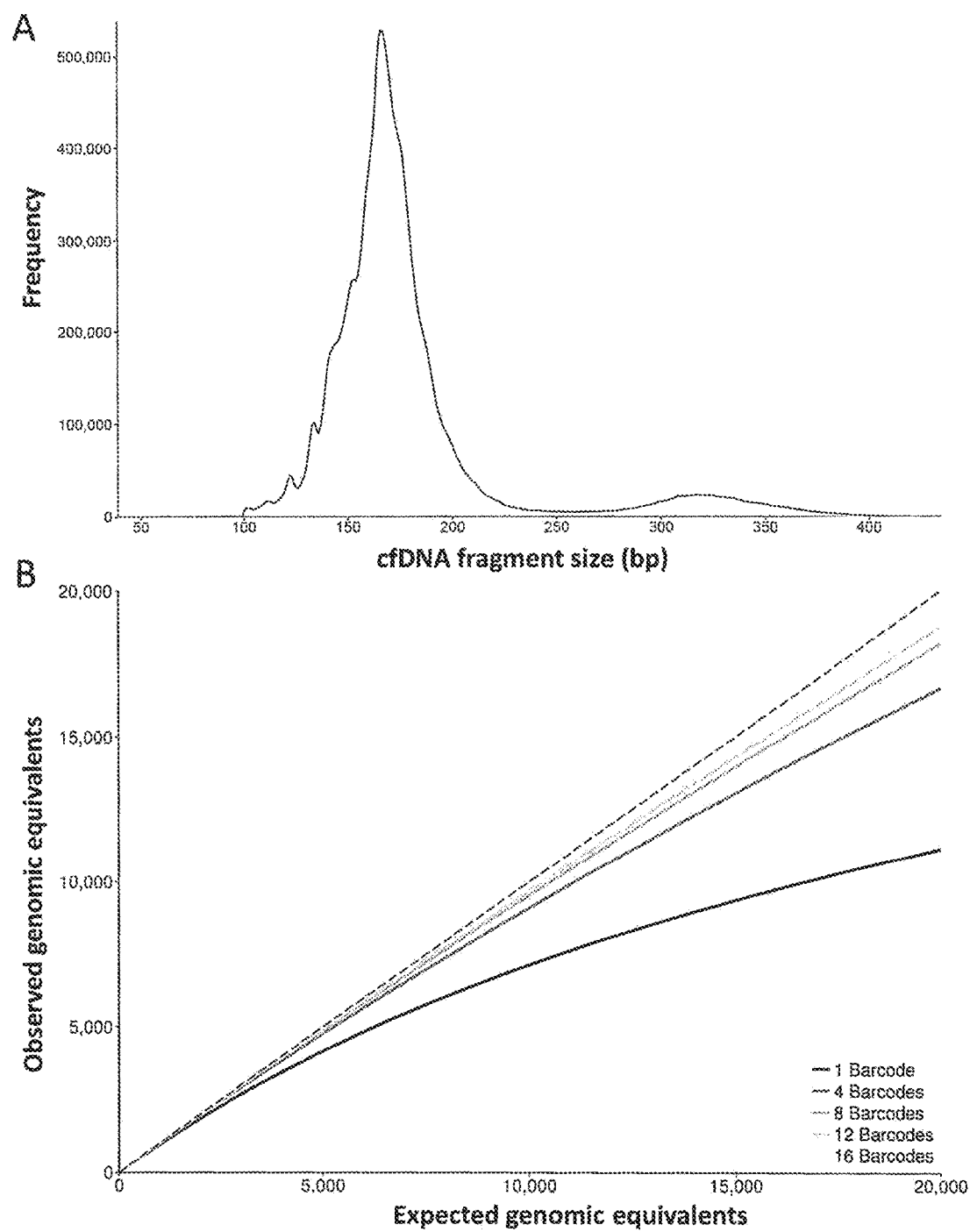
FIG. 7. Simulations using limited exogenous barcodes. Monte Carlo simulations were performed to evaluate the effect of varying the quantity of exogenous barcodes on the number of genomic equivalents that can be distinguished through next-generation sequencing as compared to the expected number of genomic equivalents. (A) Representative distribution of cfDNA fragment sizes observed from sequencing data often colorectal cancer patients. (B) Using a sliding number of expected genomic equivalents (F), we sampled F fragment lengths from the distribution in (A) with replacement. Sample fragments were then randomly assigned start and end positions relative to an arbitrary base (x). Exogenous barcodes were randomly assigned to each fragment for simulation of 1, 4, 8, 12, and 16 barcodes. These analyses indicate that a limited number of exogenous barcodes with endogenous barcodes improves the number of genome equivalents that can be analyzed at the sequencing depths typically utilized.

Conceptually, the number of genome equivalents analyzed provides a lower limit of detection for any genomic analysis. A high sensitivity approach would aim to maximize the number of unique molecules assessed while allowing for a broad and facile analysis in a range that is above the actual number of fragments present in a biologic sample. Methodologies for extraction and conversion of cell-free DNA to genomic libraries were optimized. To extend the complexity of endogenous barcodes, a limited set of sequence indices as "exogenous barcodes" were introduced in the initial steps of library generation. Monte Carlo simulations with a relatively small number of exogenous barcodes (e.g., 4-16) suggested that these, in combination with endogenous barcodes, would be sufficient to distinguish among different cell-free DNA molecules in the plasma from a typical blood draw (FIG. 7). Limiting the number of barcodes has the advantages of reducing misassignment among barcodes through sequencing errors and reducing primer dimers that can be formed during library formation.

Figure 8:
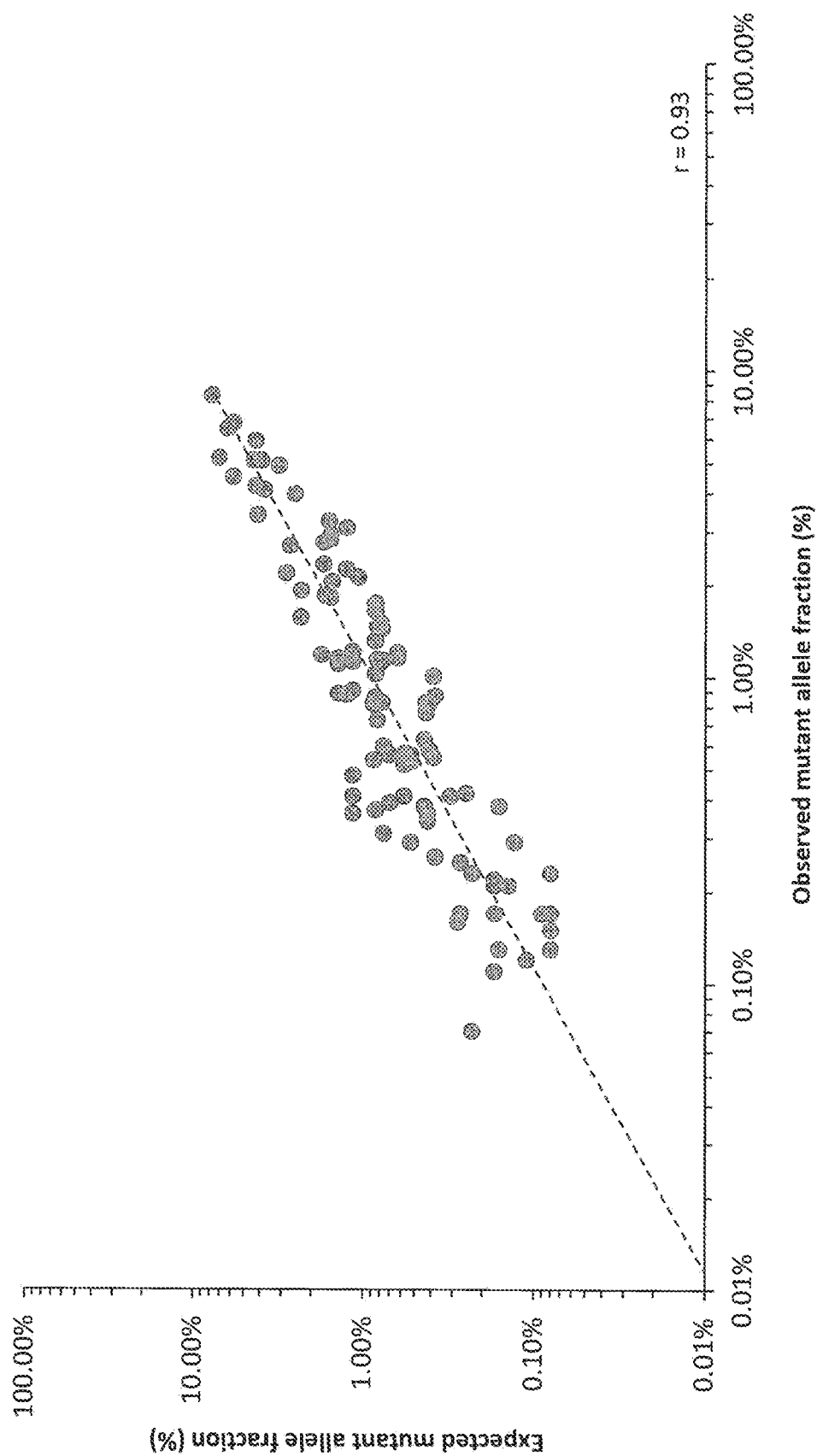
FIG. 8. Validation of TEC-Seq approach. Correlation between observed and expected mutant allele fractions from mutant pools of tumor cell line DNA mixed with varying dilutions of genomic DNA. (Pearson correlation: r=0.93, 95% CI=0.90-0.95, p<0.0001, r2=0.87.)

The characteristics of the TEC-Seq approach for detecting known tumor-specific alterations from a mixture of DNA from tumor cell lines at different dilutions with unrelated wild-type DNA were evaluated. Libraries with eight exogenous barcodes were sequenced with an average of ~33,000 sequence reads at each position among the 58 genes analyzed (Table S2). Alterations were considered to be detected if they were present in all copies of multiple sequences of each DNA molecule with identical endogenous and exogenous barcodes and were not removed by additional error filtering steps. Both hot-spot alterations (at positions previously observed to be frequently altered in cancer patients) and other alterations were considered. Alterations present in common germline variant databases or in 25% or greater of reads were considered germline and removed from further analysis unless the mutations were identical to known hot-spot alterations or represented a truncating mutation in common tumor suppressor genes (see Example 6—Materials and Methods for additional details). These analyses permitted a limit of detection of 0.05% mutant sequences in hot-spot positions and 0.10% in other positions, with a high degree of concordance to the expected fraction of mutant molecules (r=0.93, P<0.0001, Pearson correlation; FIG. 8, Table S2).

Example 2—Evaluation of Plasma from Healthy Individuals

Figure 2:
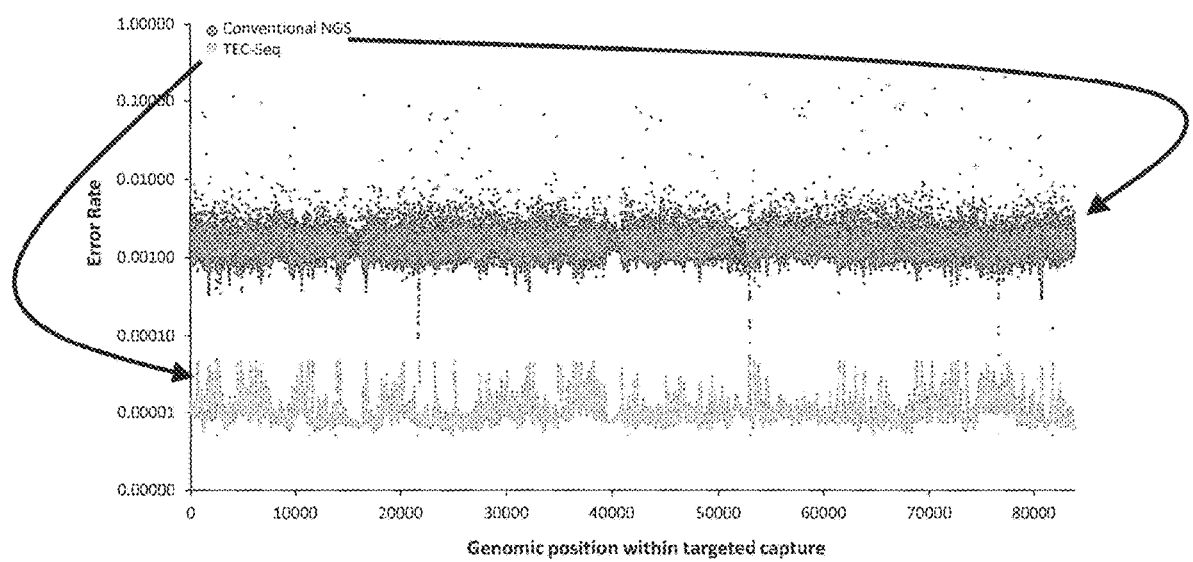
FIG. 2. TEC-Seq error correction. Sequencing error rates of conventional next generation sequencing and TEC-Seq are indicated at each base analyzed of the captured regions of interest (P<0.0001, paired t test). Error rates are determined by identifying the number of alterations at each base (or rounding up to one alteration per base if no error was identified) divided by the total distinct coverage at each base among the 44 healthy individuals analyzed.

TEC-Seq was used to examine plasma specimens from 44 healthy individuals (Tables S3 and S4). These individuals were not known to have cancer and provided their blood samples as part of a routine cancer screening visit (colonoscopy or Papanicolaou test). Samples were processed within two hours from collection, and centrifuged twice at high speed to ensure that cells and cellular debris were removed and that only cell-free DNA was analyzed. From the ~4 ml of plasma obtained from each individual, TEC-seq libraries were generated and sequenced to a ~30,000-fold coverage. Through these analyses, no mutations were observed in the cancer driver genes analyzed in the panel. The TEC-Seq analyses led to a significant reduction in sequencing error rate (FIG. 2).

Analysis of the six genes related to hematopoietic proliferation identified six individuals with a single mutation in their plasma samples, while a seventh had two detectable alterations (16% of patients analyzed, Table S5). All of the alterations were identified in DNA Methyltransferase 3 Alpha (DNMT3A), a gene that is known to be clonally altered in pre-leukemic conditions and myelodysplasia (24-26). Three of the mutations were predicted to result in the R882C change previously observed in clonal hematopoiesis, but other alterations have not been previously reported. These mutations were identified at mutant allele fractions of 0.16% to 5.3%, substantially lower than previous observations in blood cells of healthy individuals (24-26). These analyses suggest a higher fraction of asymptomatic individuals harbor such somatic alterations than had been previously reported through cellular analyses of these genes in the blood.

Example 3—Analysis of Plasma from Patients with Cancers

Figure 3:
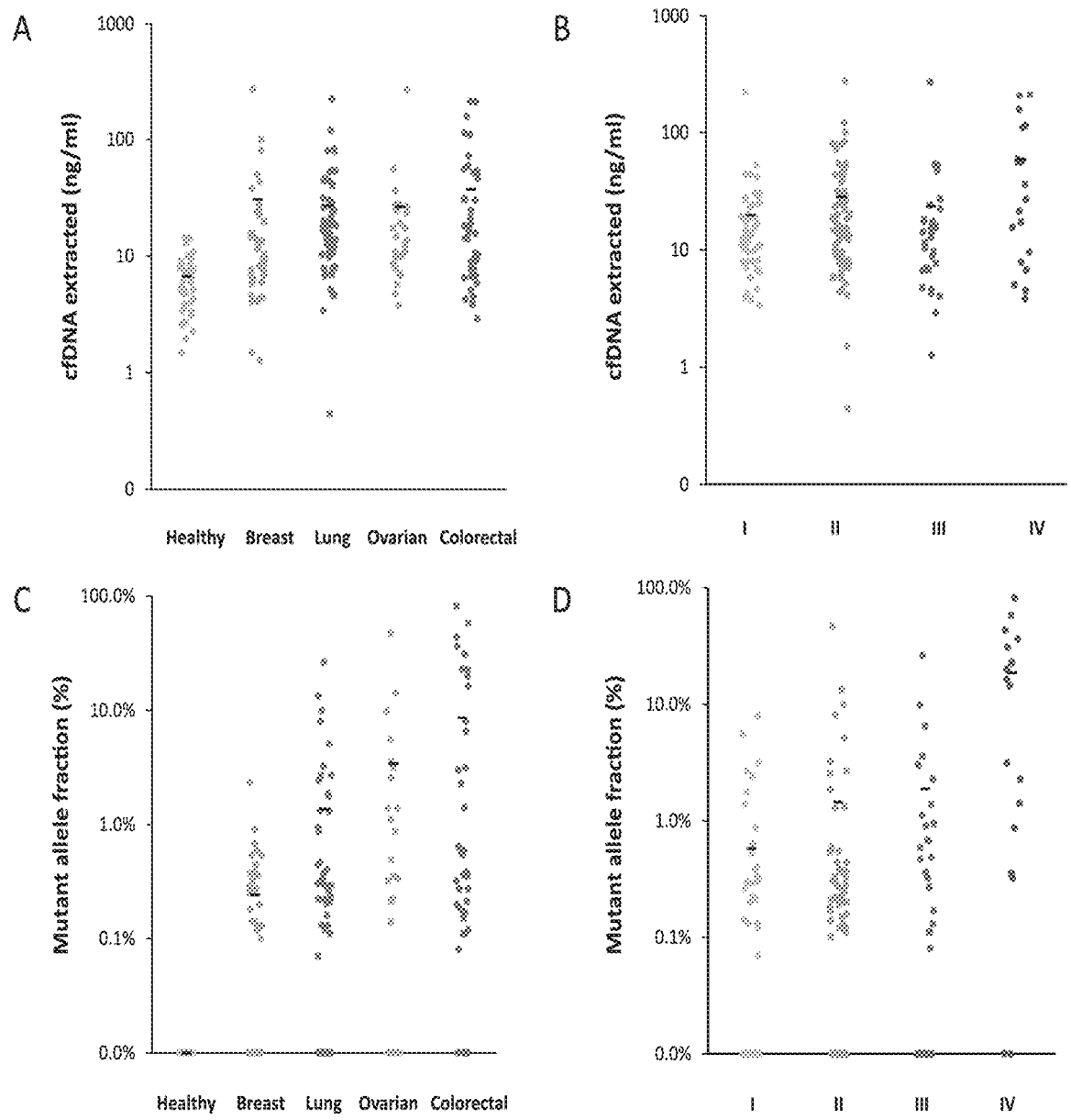
FIG. 3. Levels of cell-free DNA and circulating tumor DNA in healthy individuals and patients with cancer. Amount of cell-free DNA extracted from patients analyzed (ng/ml) (A) and from cancer patients of different stages (B). Mutant allele fraction (%) of circulating tumor DNA detected per patient analyzed (C) and from cancer patients of different stages (D). Means for each group are represented by the black bar in the column analyzed. In patients where multiple alterations are detected, the highest value is indicated. Clinical characteristics of patients and stages are indicated in Table S3.

Plasma samples from 194 patients with breast cancer (n=46), colorectal cancer (n=42), lung cancer (n=64), and ovarian cancer (n=42) were analyzed. Of the 194 cases, 153 had matched tumor and normal samples available. The cohort consisted of untreated patients having localized to metastatic disease, with the majority of patients diagnosed at stage I and II (Table S3). It was found that the concentration of cell-free DNA in plasma from cancer patients was ~29 ng/ml, significantly higher than that observed in healthy individuals (average of 7 ng/ml, P=0.001, unpaired t test, FIG. 3A). In the colorectal cancer cohort, where a larger number of later stage patients were analyzed, it was found that samples from patients with metastatic disease had higher concentration of cell-free DNA than from those with earlier stages (average of 66 ng/ml for stage IV patients versus 21 ng/ml for stage I-III, P<0.05, unpaired t test; FIG. 3B).

Figure 4:
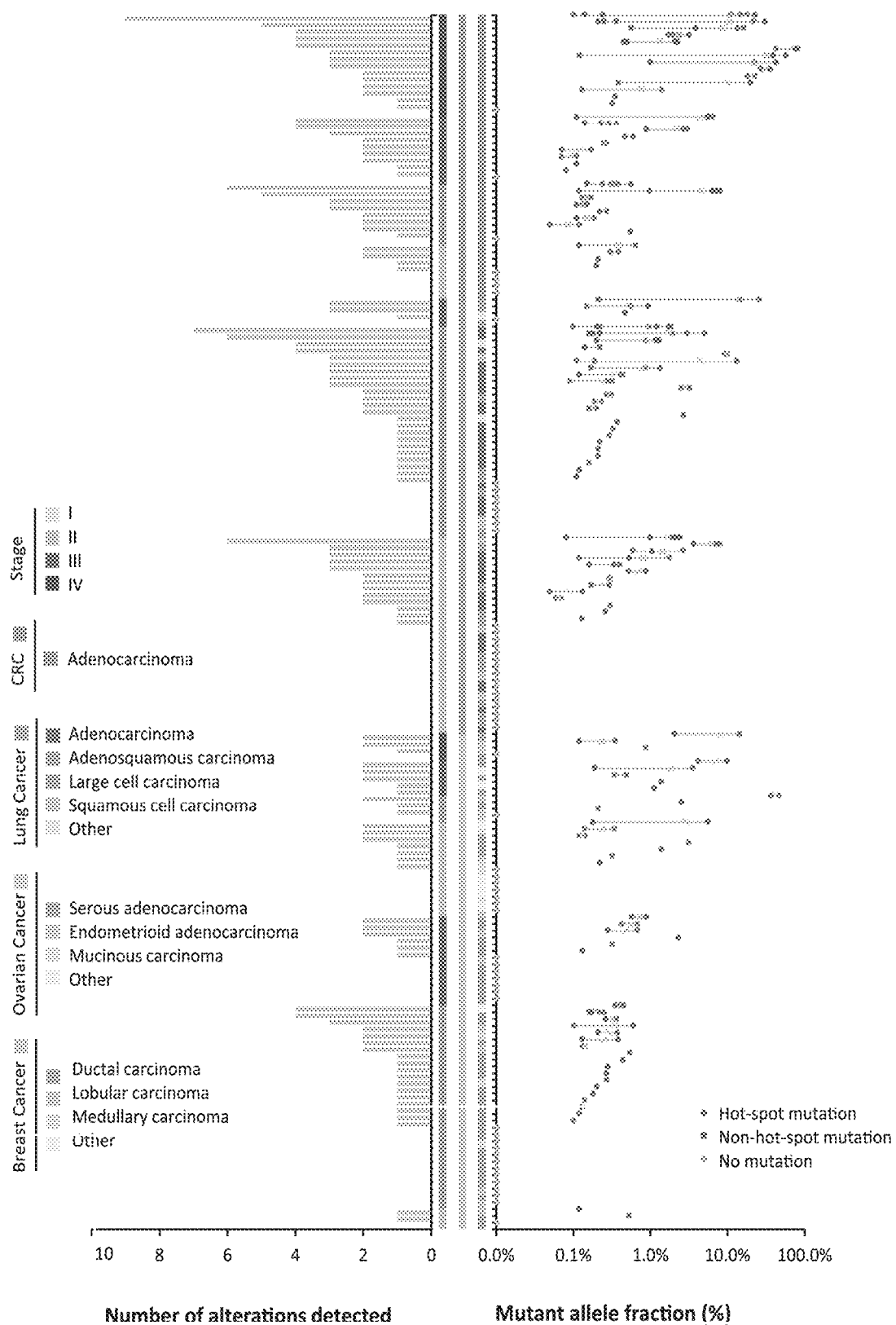
FIG. 4. Circulating tumor DNA in patients with breast, colorectal, lung, and ovarian cancer. Patients (n=194) are each represented by a tick-mark. Left: Bar chart shows the number of alterations detected for each case. Center: Stage, cancer type, and histopathological subtype are represented in colored vertical bars. Right: Mutant allele fractions of each alteration detected per patient are indicated with an 'x' at the mean. Alterations are colored based on hot-spot status and whether any alterations were detected in the case.
Figure 9:
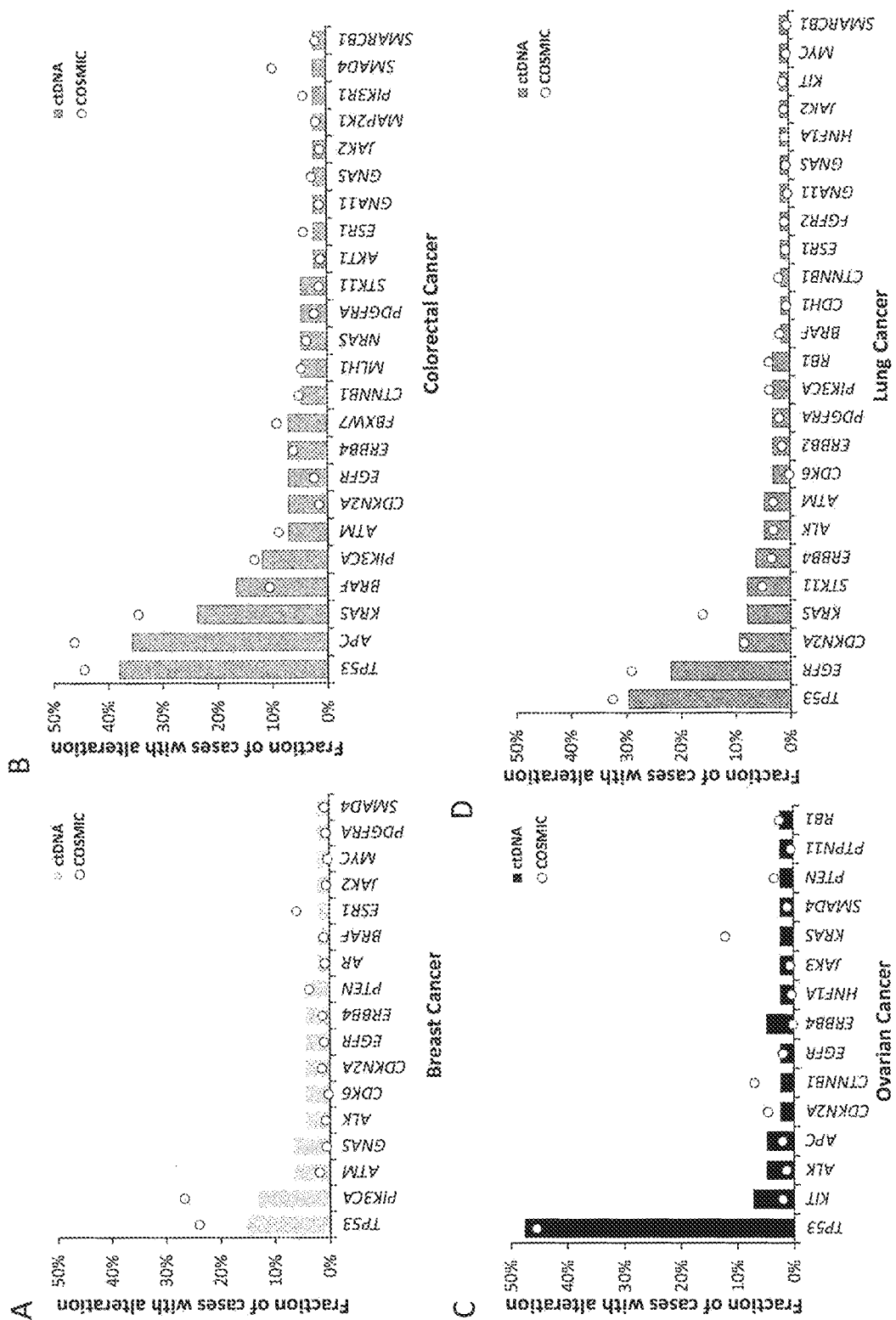
FIG. 9. Mutation frequencies in cancer genes. Bar charts depict the fraction of patients with an alteration in a cancer driver gene observed in the plasma using TEC-Seq for breast (A), colorectal (B), ovarian (C), and lung (D) cancer cohorts. The fraction of cancer cases reported in the COSMIC database with an alteration in the same genes is shown in the overlaid dot plot. The fraction of patients in our study and in the COSMIC database with an alteration in the genes of interest was similar for 76 out of 81 genes analyzed (P>0.05 for 76 of 81 genes, Fisher's exact test).

Cell-free DNA from these patients was examined using the TEC-Seq approach. Of the 194 patients analyzed, over three quarters of colorectal cancer patients, two thirds of ovarian cancer patients, and the majority of lung and breast cancer patients had detectable alterations in driver genes (Table 2, FIG. 4). Seventy-nine of these 127 detected cases had at least one alteration in a gene hot-spot position (FIG. 4). Over three quarters of patients with advanced disease (stage III and IV) and 62% of patients with localized disease (stage I and II) were detected among all tumor types (Table 2). Circulating tumor DNA levels varied among cancer types, with breast cancer having the lowest mutant allele fraction (p<0.05, unpaired t test, FIGS. 3C and 4). Similar to observations of cell-free DNA, levels of circulating tumor DNA were higher in metastatic disease compared to earlier stage disease among all cancer types (P<0.0001, unpaired t test, FIGS. 3D and 4). The affected genes and distribution of alterations for each tumor type were similar to common driver gene alterations that have previously been reported in these cancers (FIG. 9). On average 2.1 alterations, including 0.9 changes at hot-spot positions, were observed in each patient with detectable circulating tumor DNA, with lung cancer and CRCs having a higher number of alterations per case (FIG. 4). These observations highlight the benefit of analyzing a broader panel of driver genes to increase the possibility of detecting tumor-specific alterations in the plasma.

TABLE 2

Cancer patients detected using TEC-Seq

| Cancer Type | Patients (n) | Patients with ctDNA Alterations (n) | Fraction of patients with ctDNA Alterations (%) |
|---|---|---|---|
| Colorectal | | | |
| I | 8 | 4 | 50% |
| II | 9 | 8 | 89% |
| III | 10 | 9 | 90% |
| IV | 15 | 14 | 93% |
| I-IV | 42 | 35 | 83% |
| Lung | | | |
| I | 29 | 13 | 45% |
| II | 31 | 22 | 71% |
| III | 4 | 3 | 75% |
| IV | 6 | 5 | 83% |
| I-IV | 70 | 43 | 61% |
| Ovarian | | | |
| I | 24 | 16 | 67% |
| II | 4 | 3 | 75% |
| III | 8 | 6 | 75% |
| IV | 6 | 5 | 83% |
| I-IV | 42 | 30 | 71% |
| Breast | | | |
| I | 3 | 2 | 67% |
| II | 30 | 17 | 57% |
| III | 13 | 6 | 46% |
| IV | 0 | NA | NA |
| I-IV | 46 | 25 | 54% |

TABLE 2-continued

Cancer patients detected using TEC-Seq

| Cancer Type | Patients (n) | Patients with ctDNA Alterations (n) | Fraction of patients with ctDNA Alterations (%) |
|---|---|---|---|
| All | | | |
| I, II | 138 | 85 | 62% |
| III, IV | 62 | 48 | 77% |
| I-IV | 200 | 133 | 67% |

Example 4—Comparison of Mutations in Plasma with Those in Matched Tumor and Blood Cells Of the 194 patients in the study, 153 cases had matched tumor and normal tissues that were analyzed using an independent targeted next-generation sequencing approach (Tables S3 and S4). These cases were examined to determine whether the mutations identified in the plasma were tumor-specific or may have originated during blood cell expansion. The plasma analyses performed using TEC-Seq were analyzed separately, and did not rely on any knowledge of alterations identified through these parallel tissue analyses.

86 changes from 194 patients were detected in the circulation at allele fractions>25%. These were considered to be likely germline variants as described previously. Analysis of 65 of these variants in the available corresponding blood cells identified all of these changes to be germline (Table S6). These observations suggested that cell-free DNA can be used to accurately identify germline changes in the context of tumor derived and blood cell proliferation alterations, and similarly that this approach can be used to distinguish these changes from somatic alterations.

Similar to observations in healthy individuals, alterations in DNMT3A and five other genes involved in blood cell proliferation were identified in the plasma of cancer patients (Table S5). The fraction of patients with detectable changes in these genes correlated with age, as previously observed (p<0.001, unpaired t test) (24-26). Unlike tumor-specific alterations, the levels of blood cell proliferation alterations in cell-free DNA were similar among healthy individuals as well as patients with cancer, regardless of stage. Analysis of matched white blood cells from individuals with alterations in these genes identified the corresponding mutation in a majority of cases, consistent with the notion that the alterations in cell-free DNA originated from these cells (Table S5).

Figure 5:
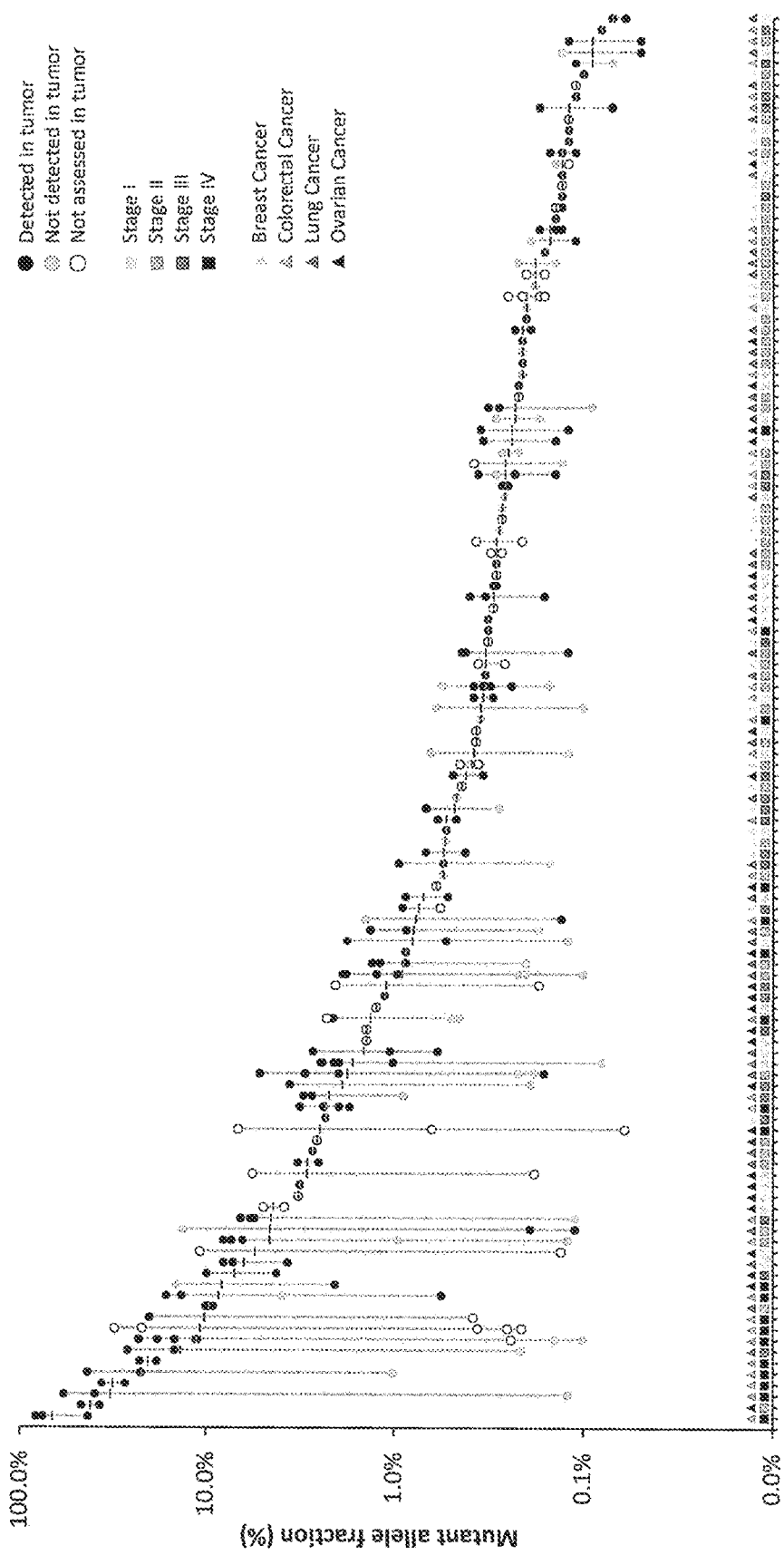
FIG. 5. Concordance between alterations in plasma and tissue. Mutant allele fractions observed in the plasma are indicated for each alteration identified with a black bar at the mean. Presence of alterations in matched tumor specimens are indicated with green dots, whereas non-concordant alterations are indicated in orange and those not assessed in gray. Stage and cancer type for each patient are plotted in the two horizontal tracks at the bottom of the figure.

After accounting for blood cell proliferation and germline alterations, 312 candidate tumor-specific changes were identified in the plasma samples in 127 of the 194 patients analyzed. 216 of these alterations were further evaluated in 100 patients where matched tumor tissue and blood cells were available. 155 of the 216 (72%) alterations were identical in both plasma and tumor samples (FIG. 5). Among stage III and IV patients, 65 of 84 variants were concordant (77%), while for early stage patients, 90 of 132 alterations were concordant (68%). In line with these observations, 70 of the 75 alterations (93%) with a mutant allele fraction of >1% in the plasma were detected in the tumor tissue of the same individual. Overall, 82 of the 100 patients (82%) had at least one alteration observed in the circulation that was identical to that in the tumor specimen.

Figure 10:
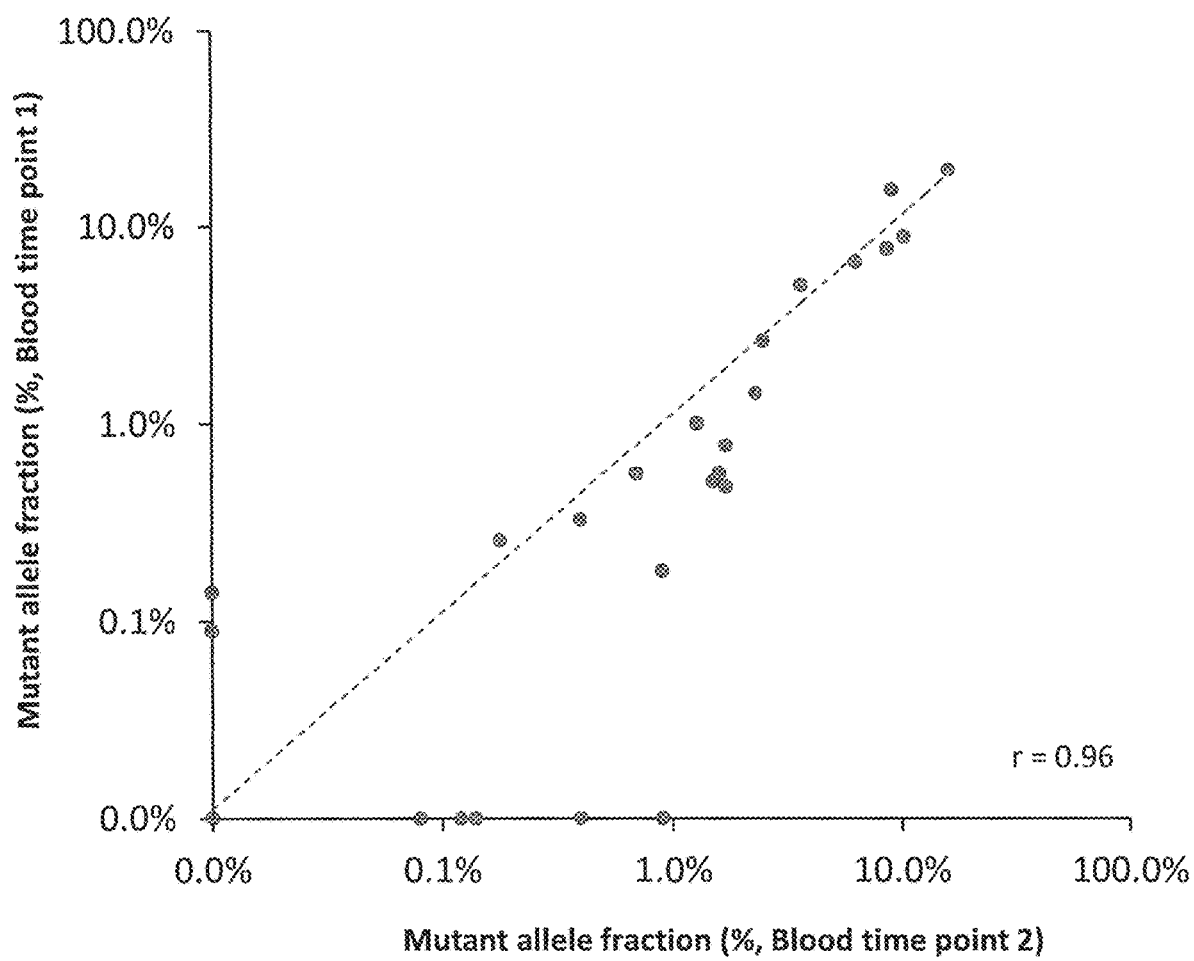
FIG. 10. Circulating tumor DNA levels in serial blood draws. Mutant allele fractions for alterations identified in two serial blood draws from six patients are indicated for each time point (Pearson r=0.96, 95% CI=0.92-0.98, p<0.0001, r2=0.93).

To evaluate reproducibility of the approach between separate blood draws in the same patients, six late stage patients with lung cancer were assessed where blood was obtained early during the course of treatment. These patients were undergoing treatment, but were observed to have progressive or stable disease. Despite the difference in time between the blood draws, it was found that 90% of the alterations observed in the second blood draw were present at the time of the first blood draw (17 of 19 alterations), with one patient having no alterations in both time points (FIG. 10). All alterations present with a mutant allele fraction>=1% were observed in both time points.

Figure 11:
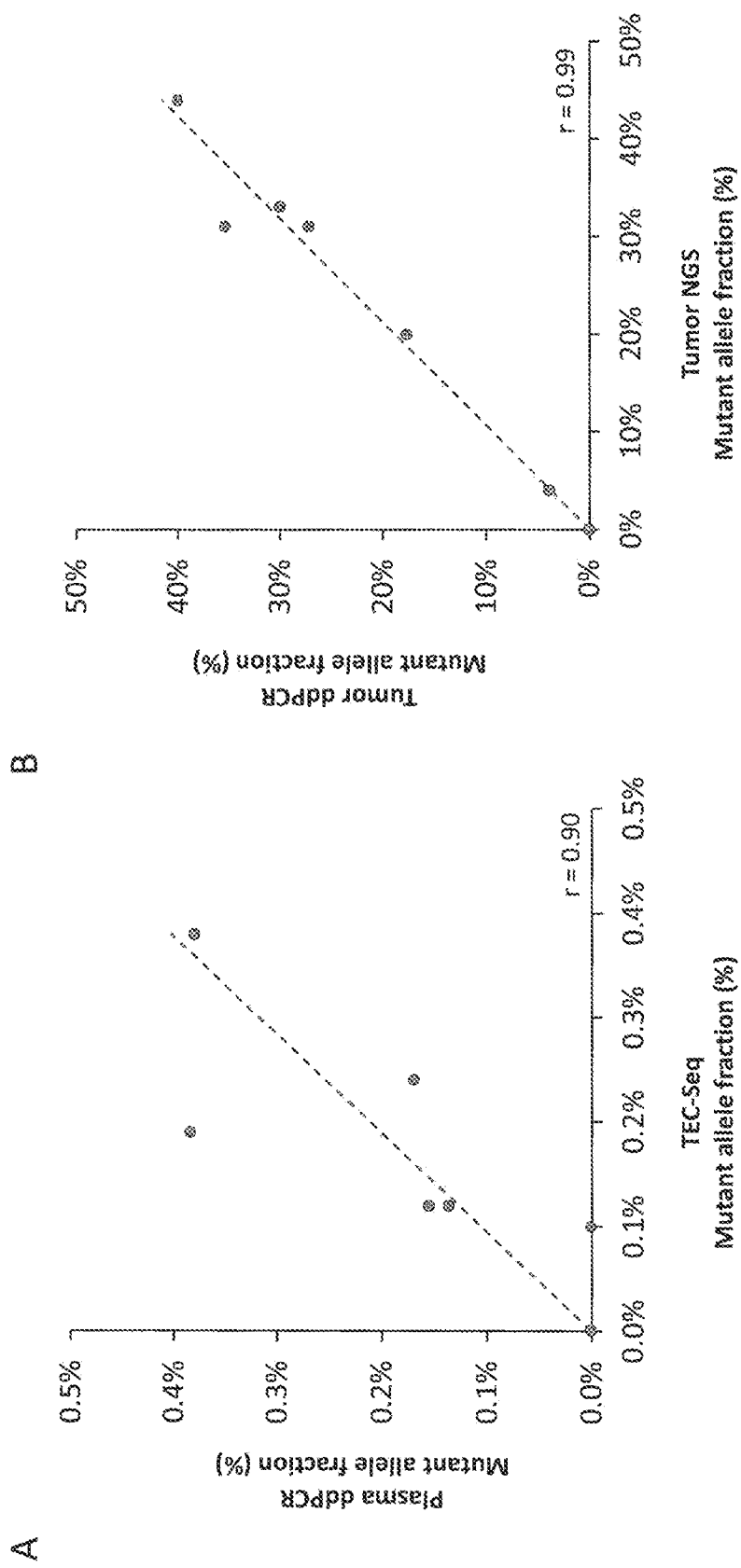
FIG. 11. Comparison of circulating tumor DNA levels between TEC-Seq and ddPCR. Correlation of independent detection of alterations in cell-free DNA using ddPCR and TEC-Seq (A. Pearson r=0.90, 95% CI=0.72-0.96, p<0.0001, r2=0.81) and in tumor tissue using ddPCR and conventional NGS (B. Pearson r=0.99, 95% CI=0.95-1.00, p<0.0001, r2=0.98).

A subset of CRC patients was evaluated to determine whether the observations detected in the plasma could be independently confirmed using droplet digital PCR (ddPCR), a method that is known to be highly sensitive for mutation detection. Six driver alterations detected in the plasma were examined, two that were also detected in matched tumors and four that were absent. Five of the six driver alterations were detected in the plasma by ddPCR at levels similar to those observed by TEC-Seq (FIG. 11A). Those not detected in tumors by targeted sequencing were similarly not identified through ddPCR approaches. Ten mutations that corresponded to the most common changes in KRAS, PIK3CA and BRAF that were detected in these tumors but were not present in the plasma of these patients were further evaluated. While it was confirmed that these alterations were in the tumors of these patients, it was found that those not detected by TEC-Seq analyses remained undetected by ddPCR in the plasma (FIG. 11B).

Figure 12:
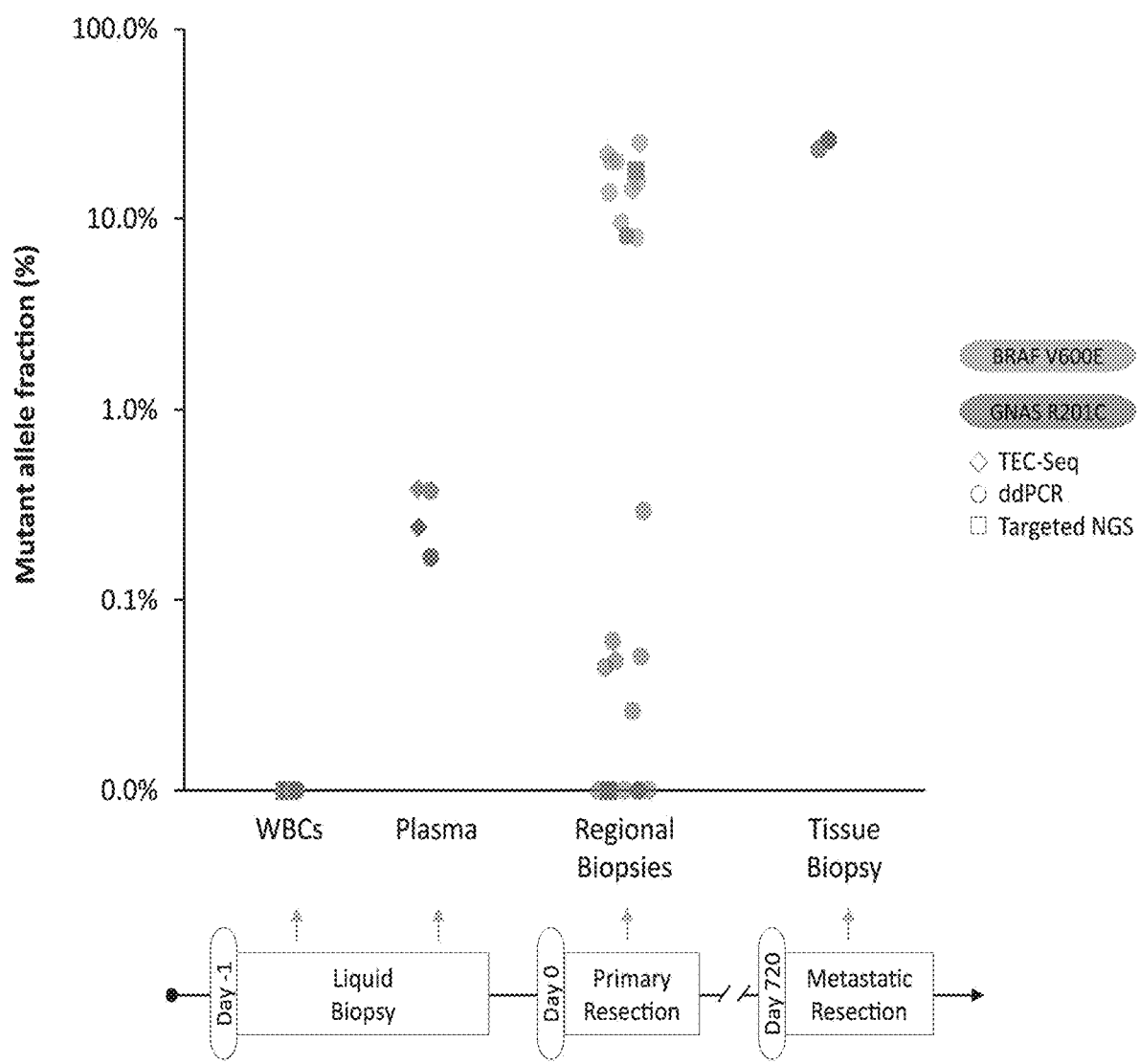
FIG. 12. Circulating tumor DNA and tumor heterogeneity. Analysis of two alterations, BRAF V600E (blue) and GNAS R201C (red), identified in a stage II CRC patient through three independent methods, TEC-Seq (diamonds), ddPCR (circles), and targeted NGS (squares). A liquid biopsy obtained one day prior to primary resection of the tumor yielded white blood cells and plasma for analysis of germline DNA and cell-free DNA, respectively. Both alterations were assessed in the white blood cells by targeted NGS and ddPCR, and in the plasma with TEC-Seq and ddPCR. Tissue from the primary resection was cored to obtain multiple biopsies each analyzed separately by ddPCR for both alterations. Two analyses of one biopsy performed using targeted NGS and ddPCR are shown in darker shades compared to biopsies assessed by ddPCR alone. Tissue from a metastatic lesion was analyzed with ddPCR for both alterations. These analyses indicate that alterations identified in the plasma using TEC-Seq may represent heterogeneous changes that are present in only a portion of the primary tumor and/or occult lesions.

To assess the possibility that tumor heterogeneity may be responsible for the apparent lack of concordance between specific alterations in the plasma and those in the tumor, multiple tumor sites from colorectal cancer patient CGCRC307 were analyzed using ddPCR. Ten different regions of the tumor were characterized, as well as a subsequent metastatic site for a R201C alteration in the GNAS gene that was detected in the plasma but not in the tumor of this patient. While a BRAF V600E alteration was found in all samples analyzed, the GNAS R201C substitution was not detected in the original tumor biopsy but was detected as a subclonal change in only a portion of the primary tumor, suggesting it developed later in tumorigenesis (FIG. 12). The GNAS R201C change identified had been previously reported in CRC (27) and has been shown to promote intestinal tumorigenesis through activation of both Wnt and ERK pathways (28). Consistent with this notion, the GNAS alteration was found to be clonal in the metastatic lesion that was identified two years after the primary tumor in this patient (FIG. 12). These results suggest that plasma alterations not detected in the matched tumor specimens may represent bona fide somatic mutations in circulating tumor DNA derived from heterogeneous primary or occult lesions.

Example 5—Circulating Tumor DNA Levels and Disease Progression

Tumor specific markers can be useful for evaluating disease progression. In CRC, carcinoembryonic antigen (CEA) is commonly used to monitor patients after therapy to determine recurrence or progressive disease (7, 29). Of the 29 CRC patients where CEA values were available, all ten cases with CEA levels>5 ng/ml had detectable circulating tumor DNA levels (Tables S3 and S6). However, of the 19 negative or borderline CEA results, 13 patients had detectable circulating tumor DNA levels, including patients of all stages (Tables S7 and S8). There was no significant correlation between circulating tumor DNA and CEA levels (r=-0.017, P=0.93, Pearson correlation).

Figure 6:
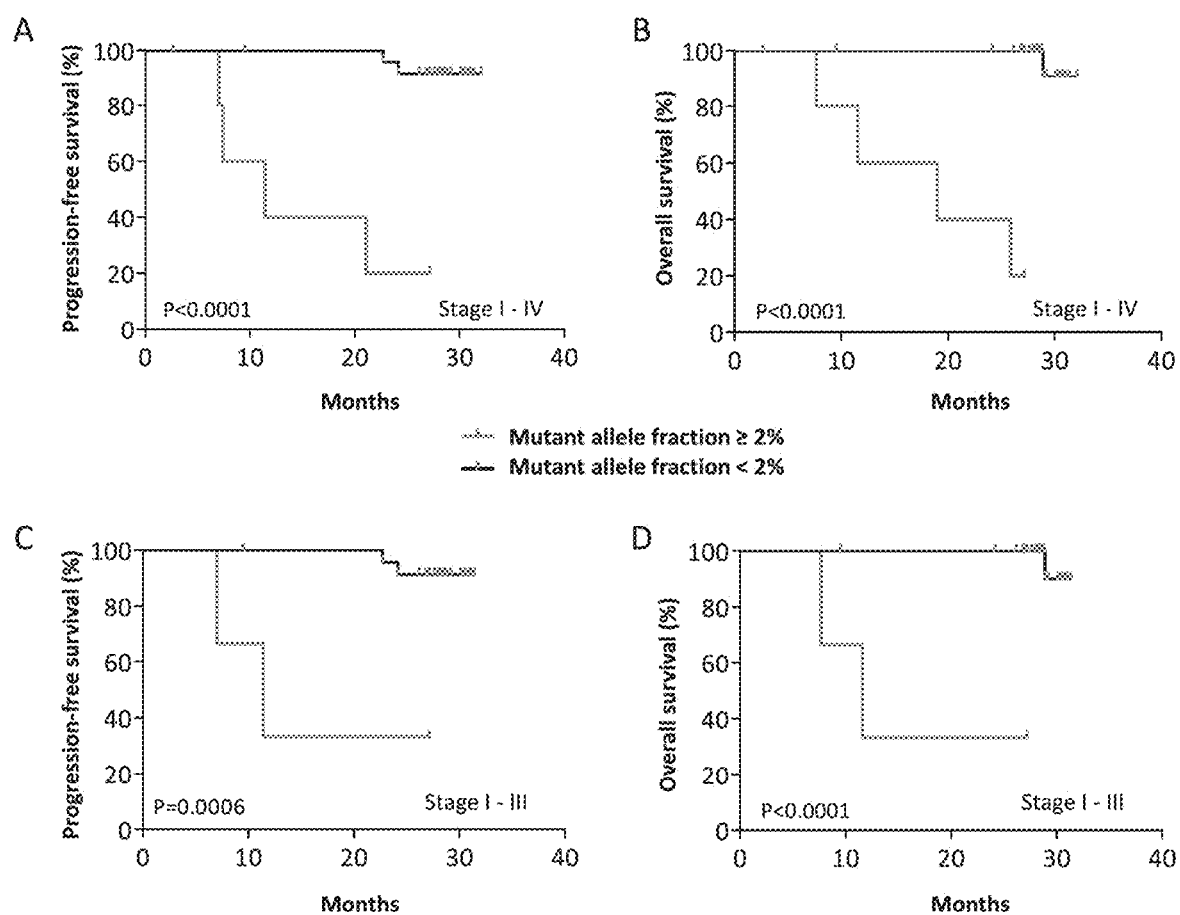
FIG. 6. Pre-operative circulating tumor DNA levels and outcome in CRC patients. Kaplan-Meier curves depict progression-free survival (A, Log-rank test p<0.0001) and overall survival (B, Log-rank test p<0.0001) of 31 CRC patients, stage I-IV, stratified based on a circulating tumor DNA mutant allele fraction threshold of 2%. Kaplan-Meier analyses of the 27 patients with stage I-III disease for progression-free survival (C, Log-rank test p=0.0006) and overall survival (D, Log-rank test p<0.0001) were performed using the same threshold in order to examine the association of circulating tumor DNA with outcome in patients without stage IV disease.
Figure 13:
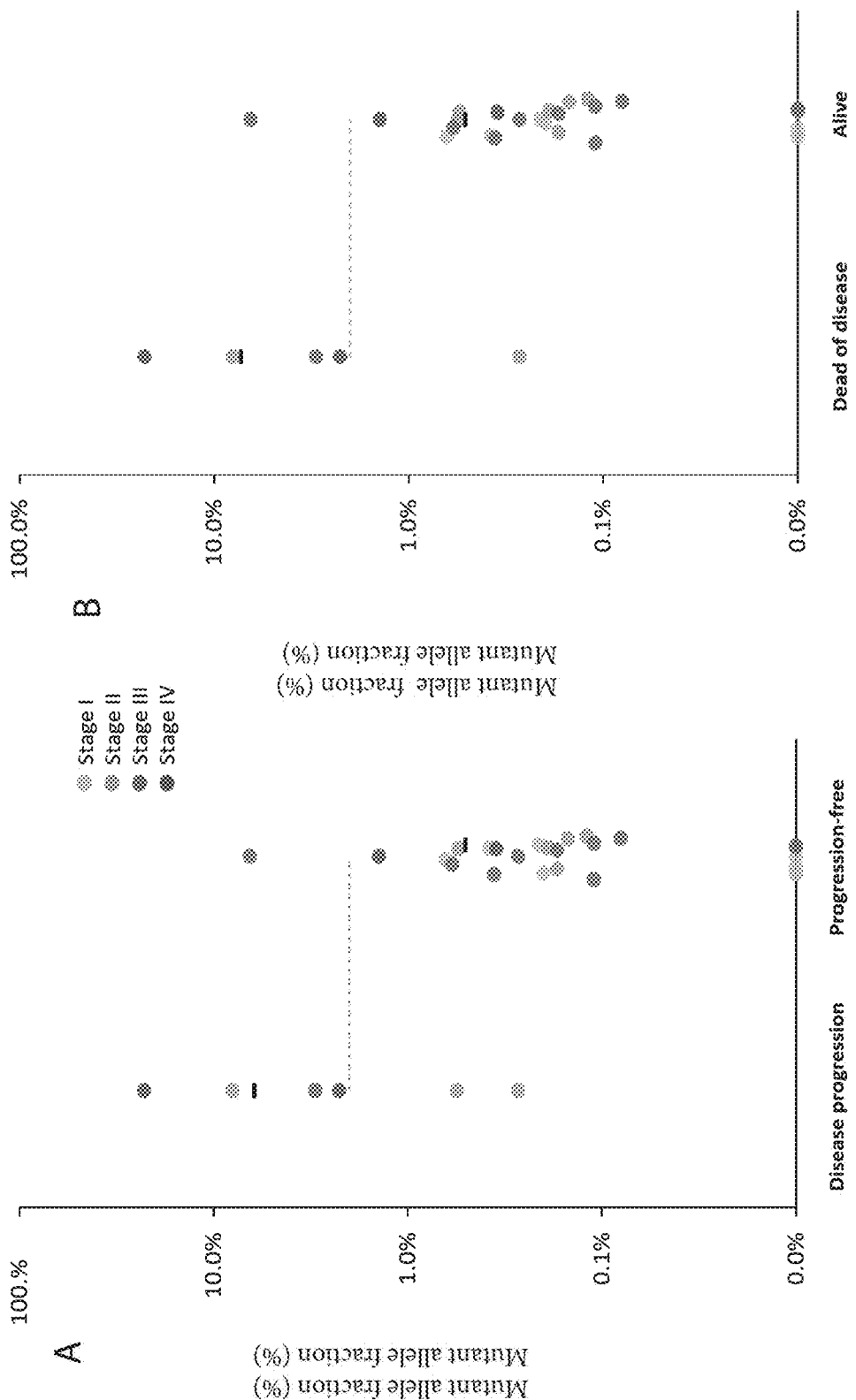
FIG. 13. Pre-operative circulating tumor DNA levels in CRC patients. Mutant allele fractions of 31 CRC patients with stage I-IV disease organized based on progression-free survival status (A, p=0.0026, unpaired t test), and overall survival status (B, p=0.0006, unpaired t test). The dotted line represents a mutant allele fraction threshold of 2%.
Figure 14:
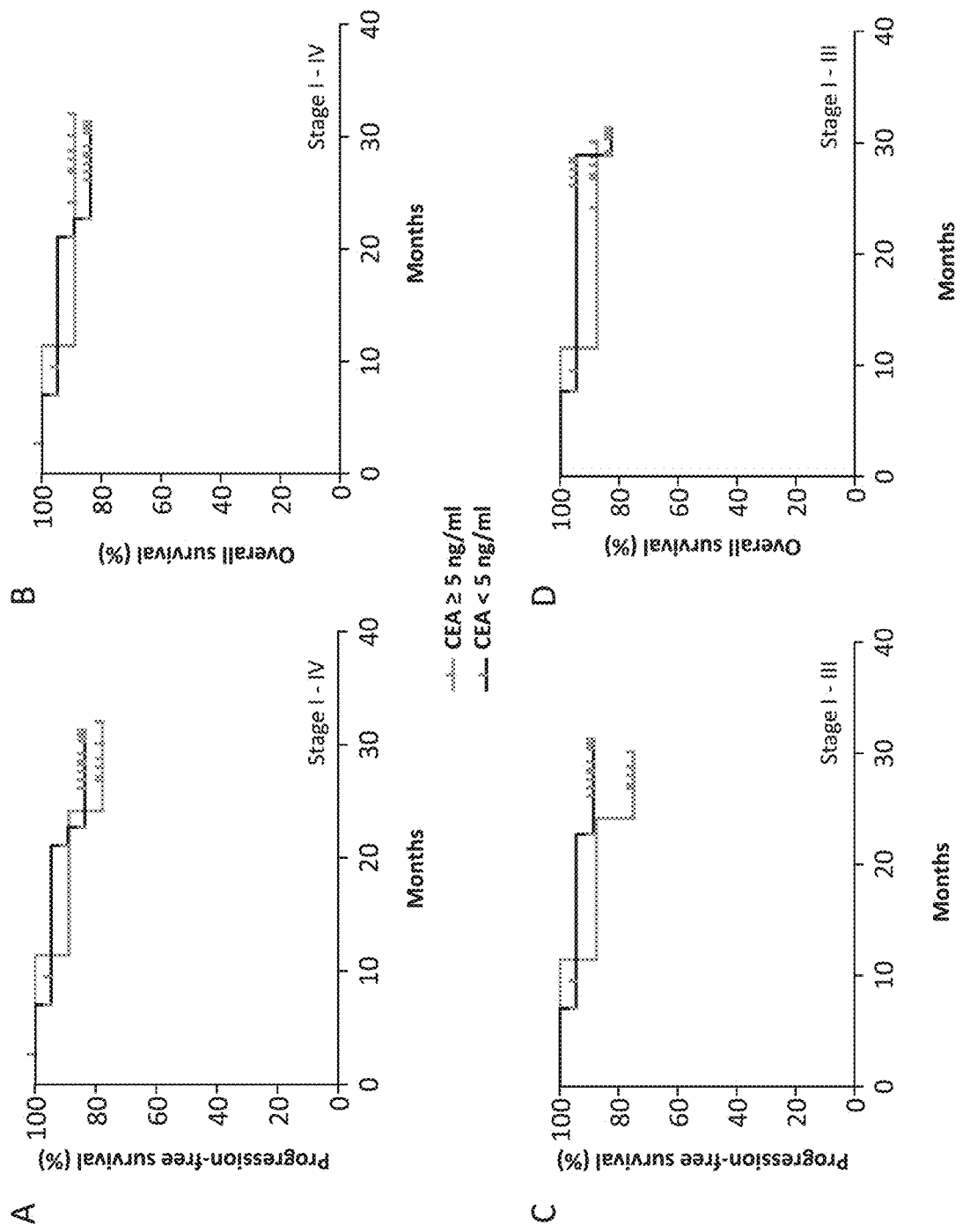
FIG. 14. Pre-operative CEA in CRC patients. Kaplan-Meier curves depict progression-free survival (A, p=0.7533, Log-rank test) and overall survival (B, p=0.7329, Log-rank test) of 31 CRC patients, stage I-IV, stratified based on a CEA threshold of 5 ng/ml. Kaplan-Meier analyses of the 27 patients with stage I-III disease for progression-free survival (C, Log-rank test p=0.4282) and overall survival (D, Log-rank test p=7345) were performed using the same threshold in order to examine the association of CEA with outcome in patients without stage IV disease.

It was next examined whether preoperative circulating tumor DNA analyses may be related to disease recurrence and survival after surgical resection. Analyses were carried out under the hypothesis that high levels of ctDNA would be more likely to be related to large primary lesions that were incompletely resected or occult metastases. A total of 31 CRC patients had potentially curable resections, including eight stage I, nine stage II, ten stage III, and four stage IV patients with liver-only metastases. Evaluation of patient prognosis when the patient had greater than 2% mutant allele fraction versus less than or equal to 2% mutant allele fraction was completed as this level was greater than three median absolute deviations from the median circulating tumor DNA levels. It was found that high levels of circulating tumor DNA (>2% mutant allele fraction) were predictive of poor prognosis (FIG. 13). Patients with elevated circulating tumor DNA levels had a shorter progression-free survival (PFS) and overall survival (OS) compared to patients with low circulating tumor DNA levels (P<0.0001 for PFS and OS, Log-rank test, FIG. 6A-B). The prognostic value for progression-free survival was significant after multivariate analysis, adjusted for stage as a categorical covariate (P<0.01, Cox multivariate test). These same predictions were observed in patients with resectable stage I-III disease (P<0.005 for PFS and OS, Log-rank, test, FIG. 6C-D). It was found that continuous circulating tumor DNA levels were also predictive of outcome (Hazard ratio=1.13, 95% CI=1.03-1.24, P<0.01 for PFS and OS, Cox univariate test) indicating that liquid biopsy analyses offer both a quantitative and qualitative assessment of disease progression. Other thresholds of elevated circulating tumor DNA (including 0.5% and 1.0%) were also evaluated and found to be significantly associated with worse outcome (P<0.01, Log-rank Test). Although previous analyses have found a limited association between preoperative CEA levels and overall survival (7, 29), CEA levels among our patients were not associated with disease outcome (P=0.75 for PFS and P=0.73 for OS, Log-rank test, FIG. 14). These analyses from a heterogeneous cohort of patients indicate that pre-operative circulating tumor DNA levels provide a useful marker of disease outcome in operable CRC.

Example 6—Materials and Methods

Study Design

This study presented a retrospective analysis of cell-free DNA using an ultrasensitive sequencing and analysis platform to detect somatic sequence alterations in early stage cancers. 250 plasma samples from 244 healthy individuals and patients with CRC, lung, ovarian, and breast cancer over a range of stages were analyzed, with most patients exhibiting localized disease. The sensitivity and specificity of the TEC-Seq method to detect circulating tumor DNA in early stage patients without prior knowledge of alterations in their tumors was evaluated. Sequence alterations We detected in hematopoietic expansion genes in healthy individuals, the sensitivity of the approach for detecting tumor-specific alterations in the blood of cancer patients was established, concordance between alterations identified in cell-free DNA and tumor samples from the same patients was evaluated, and it was assessed whether pre-operative circulating tumor DNA can serve as a marker of patient outcome.

Patient and Sample Characteristics

Plasma samples from healthy individuals, as well as plasma and tissue samples from patients with breast, lung, ovarian and colorectal cancers, were obtained from ILSBio/Bioreclamation (Chestertown, MD), Aarhus University, the Academic Medical Center, and UCSD. All samples were obtained under Institutional Review Board (IRB) approved protocols with informed consent for research use at participating institutions.

Plasma samples from healthy individuals were obtained at the time of routine screening, including for colonoscopies or pap smears. Individuals were considered healthy if they had no prior history of cancer and negative screening results. Plasma samples from individuals with CRC, lung, ovarian, and breast cancer were obtained at the time of diagnosis, prior to tumor resection. Serially collected plasma samples from lung cancer patients were collected over a course of treatment during which the patients experienced stable or progressive disease.

Matched FFPE or frozen tumor tissue and buffy coat (as a source of germline DNA) were obtained from patients whenever available. Tumor specimens were obtained from primary resection with the exception of stage IV CRC cases which were obtained from liver-only metastases in these patients. All tumor samples had ≥10% viable tumor cell content by histopathologic assessment. Clinical data for all patients included and sample data for the tissue types assayed in this study are listed in Table S3.

Sample Preparation and Next-Generation Sequencing of Cell-Free DNA

Whole blood was collected in EDTA tubes and processed immediately or within 2 hours after storage at 4° C. to separate plasma and cellular components by centrifugation at 800 g for 10 minutes at 4° C. Plasma was centrifuged a second time at 18,000 g at room temperature to remove any remaining cellular debris and stored at −80° C. until the time of DNA extraction. DNA was isolated from plasma using the Qiagen Circulating Nucleic Acids Kit (Qiagen GmbH, Hilden DE) and eluted in LoBind tubes (Eppendorf AG, Hamburg, DE). Concentration and quality of cell-free DNA was assessed using the Bioanalyzer 2100 (Agilent Technologies, Santa Clara, CA).

TEC-Seq next-generation sequencing cell-free DNA libraries were prepared from 5 to 250 ng of cell-free DNA. Genomic libraries were prepared using the NEBNext DNA Library Prep Kit for Illumina (New England Biolabs, Ipswich, MA) with four main modifications to the manufacturer's guidelines: 1) The library purification steps utilized the on-bead Ampure XP approach to minimize sample loss during elution and tube transfer steps (33), 2) NEBNext end-repair, A-tailing, and adapter ligation enzyme and buffer volumes were adjusted accordingly to accommodate the on-bead Ampure XP purification strategy, 3) a pool of 8 unique Illumina dual index adapters with 8 bp barcodes were used in the ligation reaction instead of the standard Illumina single or dual index adapters with 6 bp or 8 bp barcodes, respectively, and 4) cell-free DNA libraries were amplified with Hotstart Phusion Polymerase. Incorporation of these modifications improved conversion efficiency from 13.4% prior to modifications to 34.1% in validation analyses of 38 cases incorporating these changes. Analysis of plasma samples from healthy individuals and cancer patients revealed a conversion efficiency of 41%, with a significant correlation between input DNA amount and the number of distinct molecules analyzed.

Briefly, cell-free DNA was combined with End-Repair Reaction Buffer (NEB) and End-Repair Enzyme Mix (NEB) and incubated for 30 minutes at 20° C. The end-repair reaction was purified with Agencourt AMPure XP Beads (Beckman Coulter, Ind.). A-tailing was performed by adding 6 µl of dA Tailing Reaction Buffer (NEB) and 3.6 µl of Klenow (NEB) to the end-repaired cell-free DNA and incubating for 30 minutes at 37° C. A-tailed cell-free DNA was purified using Agencourt AMPure XP Buffer (Beckman Coulter, Ind.). Adaptor oligonucleotides containing the TEC-Seq dual index pools and Quick T4 DNA Ligase (NEB) were mixed with A-tailed, on-bead cell-free DNA and incubated for 15 min at 20° C. Ligated cell-free DNA was purified with two rounds of Agencourt AMPure XP Buffer. The cell-free DNA library was amplified using Phusion Hot Start DNA polymerase (Thermo Fisher Scientific, Fair Lawn, N.J.), and PCR primers published for the Nextera DNA library prep kit: 5'-AATGATACGGCGAC-CACCGA (SEQ ID NO: 1) and 5'-CAAGCAGAAGACGG-CATACGA (SEQ ID NO: 2) (Illumina Inc., San Diego, Calif.). For each genomic library, PCR reactions contained 2 µl of cell-free DNA library, 15.5 µl of H2O, 1.25 µl of dimethyl sulfoxide, 5.0 µl of 5× Phusion HF Buffer, 0.5 µl of dNTP mix containing 10 mM of each dNTP (Life Technologies, Gaithersburg, Md.), 0.5 µl of each primer, and 0.25 µl of Hotstart Phusion Polymerase. The following PCR conditions were used: 98° C. for 30 seconds; 12 cycles of 98° C. for 10 seconds, 60° C. for 30 seconds, and 72° C. for 30 seconds; and 72° C. for 5 minutes. Purification of the amplified cell-free DNA library was performed using Agencourt AMPure XP Beads. Concentration and quality of cell-free DNA libraries was assessed using the Bioanalyzer 2100 (Agilent Technologies, Santa Clara, Calif.).

Targeted capture was performed using the Agilent SureSelect reagents and a custom set of hybridization probes targeting 58 genes (Table S1) per the manufacturer's guidelines. The captured library was amplified with HotStart Phusion Polymerase (New England Biolabs). The concentration and quality of captured cell-free DNA libraries was assessed on the Bioanalyzer 2100 using the DNA 1000 Kit (Agilent Technologies, Santa Clara, CA). TEC-seq libraries were sequenced using 100 bp paired end runs on the Illumina HiSeq 2000/2500 (Illumina, San Diego, CA).

Sample Preparation and Next-Generation Sequencing of Tumor-Normal Pairs

Sample preparation, library construction, targeted capture, next-generation sequencing, and bioinformatic analyses of tumor and normal samples were performed as previously described (22, 34). Briefly, DNA was extracted from matched FFPE or frozen tumor tissue and buffy coat samples using the Qiagen DNA FFPE Tissue Kit or Qiagen DNA Blood Mini Kit (Qiagen GmbH, Hilden DE). Genomic DNA from tumor and normal samples was fragmented and used for Illumina TruSeq library construction (Illumina) as previously described (22, 34). Targeted regions of interest were captured using Agilent SureSelect in-solution capture reagents and a custom targeted panel for genes of interest according to the manufacturer's instructions (Agilent, Santa Clara, CA). Paired-end sequencing, resulting in 150 bases from each end of the fragment for targeted libraries, was performed using the Illumina MiSeq (Illumina, San Diego, CA).

Analyses of Next-Generation Sequencing Data from Cell-Free DNA

Primary processing of next-generation sequence data for cell-free DNA samples was performed using Illumina CASAVA software (v1.8), including demultiplexing and masking of dual index adapter sequences. Sequence reads were aligned against the human reference genome (version hg18 or hg19) using Novoalign with additional realignment of select regions using the Needleman-Wunsch method (22).

Next, candidate somatic mutations, consisting of point mutations, small insertions, and deletions were identified using VariantDx (22) across the targeted regions of interest. VariantDx examined sequence alignments of cell-free DNA plasma samples while applying filters to exclude alignment and sequencing artifacts. Specifically, an alignment filter was applied to exclude quality failed reads, unpaired reads, and poorly mapped reads in the plasma. A base quality filter was applied to limit inclusion of bases with reported phred quality score>30.

A mutation identified in cell-free DNA was considered a candidate somatic mutation only when: (i) Three distinct paired reads contained the mutation in the plasma (each redundantly sequenced at least three times) with a distribution of start positions when compared to the reference genome and the number of distinct paired reads containing a particular mutation in the plasma was at least 0.1% of the total distinct read pairs; or (ii) Four distinct paired reads contained the mutation in the plasma and the number of the number of distinct paired reads containing a particular mutation in the plasma was at least 0.05% and less than 0.1%, of the total distinct read pairs; and (iii) the mismatched base was not present in >1% of the reads in a panel of unmatched normal samples as well as not present in a custom database of common germline variants derived from dbSNP and other publicly available databases.

Mutations arising from misplaced genome alignments, including paralogous sequences, were identified and excluded by searching the reference genome. Candidate somatic mutations were further filtered based on gene annotation to identify those occurring in protein coding regions. Functional consequences were predicted using snpEff and a custom database of CCDS, RefSeq and Ensembl annotations using the latest transcript versions available on hg18 and hg19 from UCSC (genome.ucsc.edu). Predictions were ordered to prefer transcripts with canonical start and stop codons and CCDS or Refseq transcripts over Ensembl when available. Finally, mutations were filtered to exclude intronic and silent changes, while retaining mutations resulting in missense mutations, nonsense mutations, frameshifts, or splice site alterations.

Candidate alterations were defined as somatic hot-spots if the nucleotide change and amino acid change were identical to an alteration observed in ≥20 cancer cases reported in the COSMIC database. Alterations that were not hot-spots were retained only if either (i) seven or more distinct paired reads contained the mutation in the plasma and the number of distinct paired reads containing a particular mutation in the plasma was at least 0.1% and less than 0.2%, of the total distinct read pairs, or (ii) six or more distinct paired reads contained the mutation in the plasma and the number of distinct paired reads containing a particular mutation in the plasma was at least 0.2% of the total distinct read pairs. Candidate mutations further limited through identification and removal of common germline variants present in ≥25% of reads or <25% of reads if the variant was recurrent and the majority of alterations at that position had a MAF≥25% (Table S6). Variants known to be at a somatic hot-spot position, or producing a truncating mutation in a tumor suppressor gene were not excluded as germline changes. Because of the high frequency of mutations in specific genes and the possible confounding between somatic and germline changes, we limited analyses in the APC gene to frameshift or nonsense mutations, and in KRAS, HRAS and NRAS to positions to 12, 13, 61, and 146. Finally, we excluded hematopoietic expansion related variants that have been previously described, including those in DNMT3A, IDH1, and IDH2 and specific alterations within ATM (residue 3008), GNAS (residue 202), or JAK2 (residue 617) (Table S1) (24-26).

To compare the TEC-Seq bioinformatic approach to other methods, we used bioinformatic components of CAPP-Seq/iDES combined with the requirement of multiple distinct read families based on endogenous and exogenous barcodes (19, 21) (found at the URL cappseq.stanford.edu/ides). Using this approach, analysis of 15 plasma samples from our cohort of healthy individuals across our entire gene panel identified multiple false positive alterations in all cases, and in the majority of cases after requiring higher numbers of distinct read families (beyond those described references 19 and 21). A similar analysis of 170 cancer cases from our cohort using the CAPP-Seq/iDES bioinformatic pipeline removed 18 somatic alterations, including 9 that had been confirmed in the matched tissues from the same patient or were present at known hot-spot positions. Alternatively, analysis of plasma from all 200 cancer cases analyzed in this study using the 292 hot-spot positions utilized in the CAPP-Seq/iDES approach (19, 21) yielded a reduced fraction of detected cases, including 40%, 55%, 45%, and 17% of lung, colorectal, ovarian and breast cancer, respectively.

Analyses of Next-Generation Sequencing Data from Tumor-Normal Pairs

Primary processing of next-generation sequencing data from tumor-normal pairs and identification of putative somatic mutations was completed using Illumina CASAVA (Consensus Assessment of Sequence and Variation) software V1.8 and VariantDx custom software respectively as previously described (22).

What is claimed is:

1. A method for identifying the presence of circulating tumor DNA in a subject, and treating said subject comprising:
 detecting one or more genetic alterations in cell-free DNA in a biological sample isolated from the subject, wherein the step of detecting is performed when the subject is not known to harbor a cancer cell; and wherein the step of detecting one or more genetic alterations in cell-free DNA includes using a method comprising steps of:
 i) extracting cell-free DNA from blood;
 ii) ligating a low complexity pool of dual index barcode adapters to the cell-free DNA to generate a plurality of barcode adapter-ligated cell-free DNA segments, wherein the barcodes each consist of 6 or 8 base pairs;
 iii) capturing the plurality of barcode adapter-ligated cell-free DNA segments;
 iv) sequencing the plurality of captured barcode adapter-ligated cell-free DNA segments, wherein the captured DNA segments are sequenced at least three times with a distribution of start positions as compared to a reference genome;
 v) aligning the sequenced plurality of captured barcode adapter-ligated cell-free DNA segments to a reference genome;
 vi) identifying sequence alterations using aligned sequences of multiple distinct molecules containing identical redundant changes; and,
 vii) identifying the presence of circulating tumor DNA when at least one of the detected genetic alterations in the cell-free DNA is a cancer cell mutations; and thereafter
 administering a therapeutic agent to the subject.

2. The method of claim 1, wherein the biological sample is selected from the group consisting of blood, plasma, urine, cerebrospinal fluid, saliva, sputum, broncho-alveolar lavage, bile, lymphatic fluid, cyst fluid, stool, ascites, and combinations thereof.

3. The method of claim 1, wherein the presence of circulating tumor DNA indicates the presence of a cancer cell.

4. The method of claim 1, wherein the cancer cell mutation is present in a gene selected from the group consisting of ARID1A, AKT, anaplastic lymphoma kinase (ALK), BRAF, cyclin dependent kinase inhibitor 2 (CDKN2A), discoidin domain receptor tyrosine kinase 2 (DDR2), epidermal growth factor receptor (EGFR), fibroblast growth factor receptor 1 (FGFR1), HER2/ERBB2, kelch like ECH associated protein 1 (KEAP1), KRAS protooncogene (KRAS), MAP kinase/ERK kinase 1 (MEK1), MET proto-oncogene (MET), MAX gene associated (MGA), myelocytomatosis oncogene (MYC), NF1, NRAS, neutrophophic receptor tyrosine kinase 1 (NTRK1), PTEN, PIK3CA, RB1, RNA binding motif protein 10 (RBM10), ret proto-oncogene (RET), Ras like without CAAX 1 (RIT1), Ros proto-oncogene (ROS1), STE domain containing 2 (SETD2), SWI/SNF related matrix associated actin dependent regulator of chromatin, subfamily A, member 4 (SMARCA4), (SOX2), LKB1 (STK11), TP53, U2 small nuclear RNA auxiliary factor 1 (U2AF1), or combinations thereof.

5. The method of claim 1, wherein the step of detecting one or more genetic alterations in cell-free DNA includes further using a method selected from the group consisting of: a targeted capture method, a next-generation sequencing method, and an array-based method, and combinations thereof.

6. A method for identifying the presence of a lung cancer cell in a subject and treating the subject, comprising:
 detecting one or more genetic alterations in cell-free DNA in a biological sample isolated from the subject, wherein the step of detecting is performed when the subject is not known to harbor a lung cancer cell; and wherein the step of detecting one or more genetic alterations in cell-free DNA includes using a method comprising steps of:
 i) extracting cell-free DNA from blood;
 ii) ligating a low complexity pool of dual index barcode adapters to the cell-free DNA to generate a plurality of barcode adapter-ligated cell-free DNA segments, wherein the barcodes each consist of 6 or 8 base pairs;
 iii) capturing the plurality of barcode adapter-ligated cell-free DNA segments;
 iv) sequencing the plurality of captured barcode adapter-ligated cell-free DNA segments, wherein the captured DNA segments are sequenced at least three times with a distribution of start positions as compared to a reference genome;
 v) aligning the sequenced plurality of captured barcode adapter-ligated cell-free DNA segments to a reference genome;
 vi) identifying sequence alterations using aligned sequences of multiple distinct molecules containing identical redundant changes; and
 vii) identifying the presence of circulating tumor DNA when at least one of the detected genetic alterations in the cell-free DNA is a lung cancer cell mutation; and
 viii) identifying the presence of the lung cancer cell when the presence of circulating tumor DNA is identified; and thereafter
 administering a therapeutic agent to the subject.

7. The method of claim 6, wherein the cancer cell mutation is present in a gene selected from the group consisting of ARID1A, AKT, anaplastic lymphoma kinase (ALK), BRAF, cyclin dependent kinase inhibitor 2 (CDKN2A), discoidin domain receptor tyrosine kinase 2 (DDR2), epidermal growth factor receptor (EGFR), fibroblast growth factor receptor 1 (FGFR1), HER2/ERBB2, kelch like ECH associated protein 1 (KEAP1), KRAS protooncogene (KRAS), MAP kinase/ERK kinase 1 (MEK1), MET proto-oncogene (MET), MAX gene associated (MGA), myelocytomatosis oncogene (MYC), NF1, NRAS, neutrophophic receptor tyrosine kinase 1 (NTRK1), PTEN, PIK3CA, RB1, RNA binding motif protein 10 (RBM10), ret proto-oncogene (RET), Ras like without CAAX 1 (RIT1), Ros proto-oncogene (ROS1), STE domain containing 2 (SETD2), SWI/SNF related matrix associated actin dependent regulator of chromatin, subfamily A, member 4 (SMARCA4), (SOX2), LKB1 (STK11), TP53, U2 small nuclear RNA auxiliary factor 1 (U2AF1), or combinations thereof.

8. A method for identifying the presence of circulating tumor DNA in a subject, and treating said subject comprising:
 detecting one or more genetic alterations in cell-free DNA in a biological sample isolated from the subject, wherein the step of detecting is performed when the subject is not known to harbor a cancer cell; and wherein the step of detecting one or more genetic alterations in cell-free DNA includes using a method comprising steps of:
 i) extracting cell-free DNA from blood;
 ii) ligating a low complexity pool of dual index barcode adapters to the cell-free DNA to generate a plurality of barcode adapter-ligated cell-free DNA segments;

iii) capturing the plurality of barcode adapter-ligated cell-free DNA segments;
iv) sequencing the plurality of captured barcode adapter-ligated cell-free DNA segments, wherein the captured DNA segments are sequenced at least three times with a distribution of start positions as compared to a reference genome;
v) aligning the sequenced plurality of captured barcode adapter-ligated cell-free DNA segments to a reference genome;
vi) identifying sequence alterations using aligned sequences of multiple distinct molecules containing identical redundant changes;
vii) identifying the presence of circulating tumor DNA when at least one of the detected genetic alterations in the cell-free DNA is a cancer cell mutation; and
administering a therapeutic agent to the subject.

* * * * *

```
SEQUENCE LISTING

<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: synthetic oligonucleotide

<400> SEQUENCE: 1
aatgatacgg cgaccaccga                                             20

<210> SEQ ID NO 2
<211> LENGTH: 21
<212> TYPE: DNA
<213> ORGANISM: Artificial
<220> FEATURE:
<223> OTHER INFORMATION: synthetic oligonucleotide

<400> SEQUENCE: 2
caagcagaag acggcatacg a                                           21

<210> SEQ ID NO 3
<211> LENGTH: 53
<212> TYPE: DNA
<213> ORGANISM: Artificial
<220> FEATURE:
<223> OTHER INFORMATION: synthetic oligonucleotide

<400> SEQUENCE: 3
actgactgac tgactgactg actgattgcc tgactgacta ctgactgact gac       53

<210> SEQ ID NO 4
<211> LENGTH: 54
<212> TYPE: DNA
<213> ORGANISM: Artificial
<220> FEATURE:
<223> OTHER INFORMATION: synthetic oligonucleotide

<400> SEQUENCE: 4
actgactgac tgactgactg actgactgac tgactgactg actgactgac tgac      54
```